(12) United States Patent
Kageyama

(10) Patent No.: US 8,806,942 B2
(45) Date of Patent: Aug. 19, 2014

(54) EVALUATION METHOD FOR BOTANICAL-INTEGRITY OF VASCULAR PLANT, IRRIGATING METHOD TO VASCULAR PLANT, FILM ELECTRET SENSOR AND FILM ECM ARRAY

(75) Inventor: Kensuke Kageyama, Kita-ku (JP)

(73) Assignee: National University Corporation Saitama University, Saitama-shi (JP)

( * ) Notice: Subject to any disclaimer, the term of this patent is extended or adjusted under 35 U.S.C. 154(b) by 637 days.

(21) Appl. No.: 13/133,078

(22) PCT Filed: Dec. 3, 2009

(86) PCT No.: PCT/JP2009/070288
§ 371 (c)(1),
(2), (4) Date: Aug. 12, 2011

(87) PCT Pub. No.: WO2010/064669
PCT Pub. Date: Jun. 10, 2010

(65) Prior Publication Data
US 2011/0288689 A1 Nov. 24, 2011

(30) Foreign Application Priority Data
Dec. 5, 2008 (JP) ................................ 2008-311569

(51) Int. Cl.
*G01N 29/11* (2006.01)
*A01G 25/16* (2006.01)
(52) U.S. Cl.
USPC .............................. 73/579; 73/599; 700/284
(58) Field of Classification Search
USPC .................... 73/579, 599; 700/284
See application file for complete search history.

(56) References Cited

U.S. PATENT DOCUMENTS

| 5,357,805 | A | 10/1994 | Fujimoto et al. |
| 7,412,880 | B2* | 8/2008 | Barreiro et al. ............ 73/170.07 |
| 7,987,735 | B2* | 8/2011 | Mann et al. ................ 73/862.59 |
| 8,085,602 | B2* | 12/2011 | Yang et al. ............... 365/189.05 |
| 8,085,974 | B2* | 12/2011 | Dvorkin et al. ................ 382/100 |
| 2007/0125155 | A1* | 6/2007 | Barreiro et al. .................. 73/37 |

FOREIGN PATENT DOCUMENTS

| JP | 60 158321 | 8/1985 |
| JP | 5 72071 | 3/1993 |

OTHER PUBLICATIONS

Ikeda, T., "Jumoku Ni Hassel Suru Cavitation No Acoustic Emission-Ho Ni Yoru Kenshutsu", Journal of Japanese Forestry Society, vol. 76, No. 4, pp. 364-366, (1994) (with partial English translation).

(Continued)

*Primary Examiner* — J M Saint Surin
(74) *Attorney, Agent, or Firm* — Oblon, Spivak, McClelland, Maier & Neustadt, L.L.P.

(57) ABSTRACT

A method includes measuring an occurrence frequency of elastic waves generated by cavitations in vascular tissues in vascular plant, before and after a change in water stress to the vascular plant, respectively by an elastic wave reception sensor fixed to an axis of the vascular plant, calculating a change rate of the occurrence frequency, from the occurrence frequency of the elastic wave measured before and after the change, respectively, and determining whether or not an embolism in the vascular tissue arrives at an unrecoverable level of the embolism, from the calculated change rate. And then, one can determine irrigation timing and quantity to the vascular plant, using an index based upon the above-determined result.

19 Claims, 38 Drawing Sheets

(56) References Cited

OTHER PUBLICATIONS

Kageyama, K. et al., "Nondestructive Evaluation of Vascular Tissue in Stem of Miniature Tomato", Proceedings of JSEM : Annual Conference on Experimental Mechanics, vol. 7, pp. 108-109, (Aug. 6-8, 2007) (with English abstract and partial English translation).

International Search Report Issued Mar. 23. 2010 in PCT/JP09/070288 filed Dec. 3, 2009.

Extended European Search Report issued Dec. 10, 2013 in Patent Application No. 09830435.5.

* cited by examiner

FIG. 11
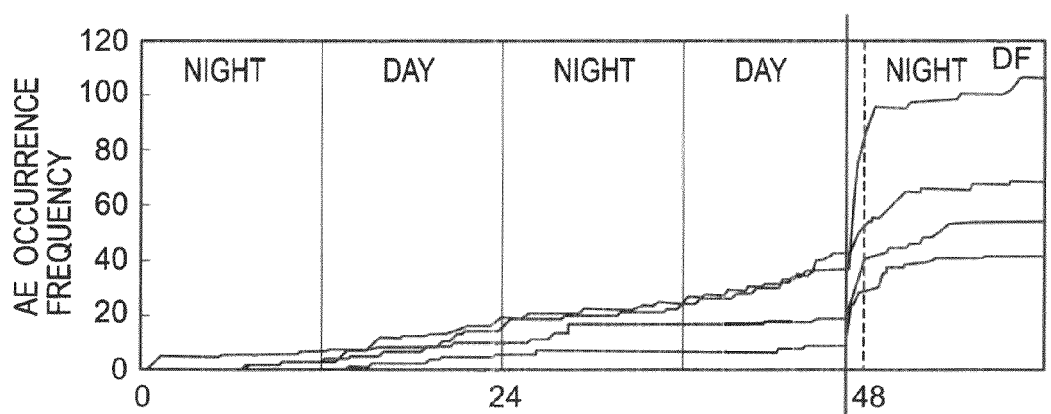
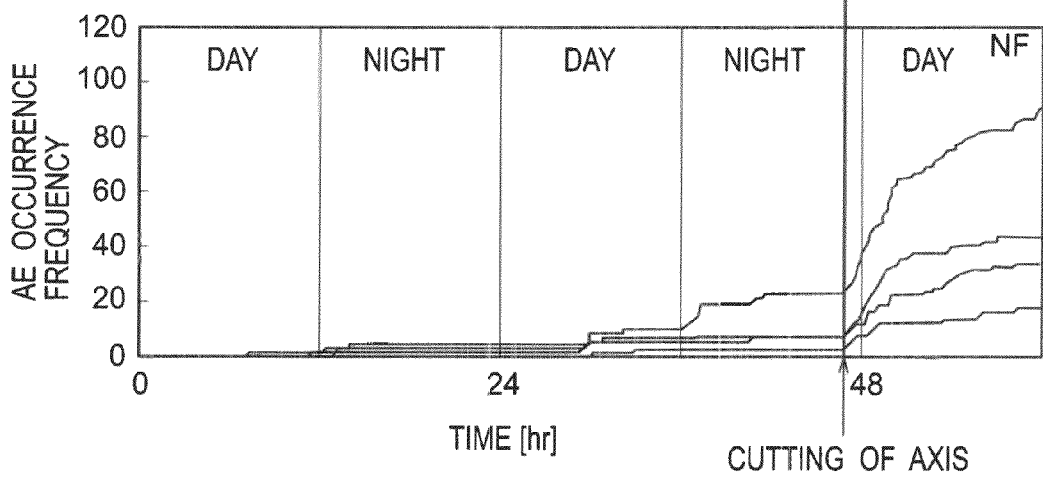

FIG. 12
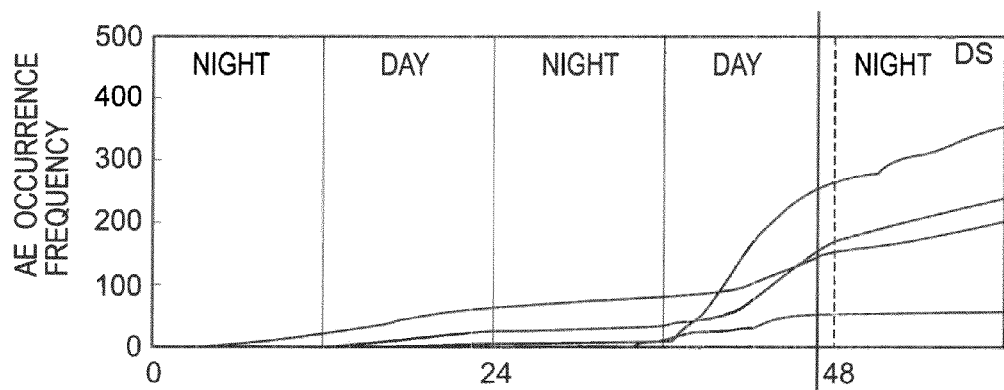
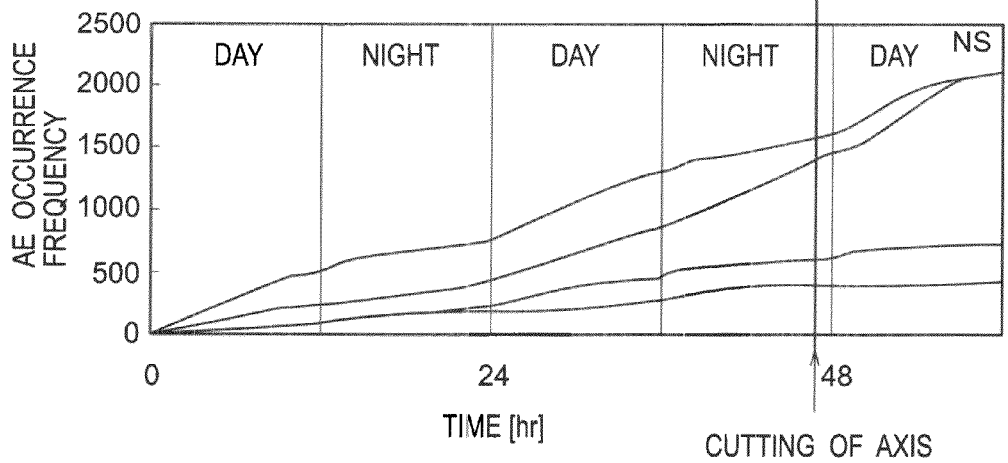

FIG. 22
(a)
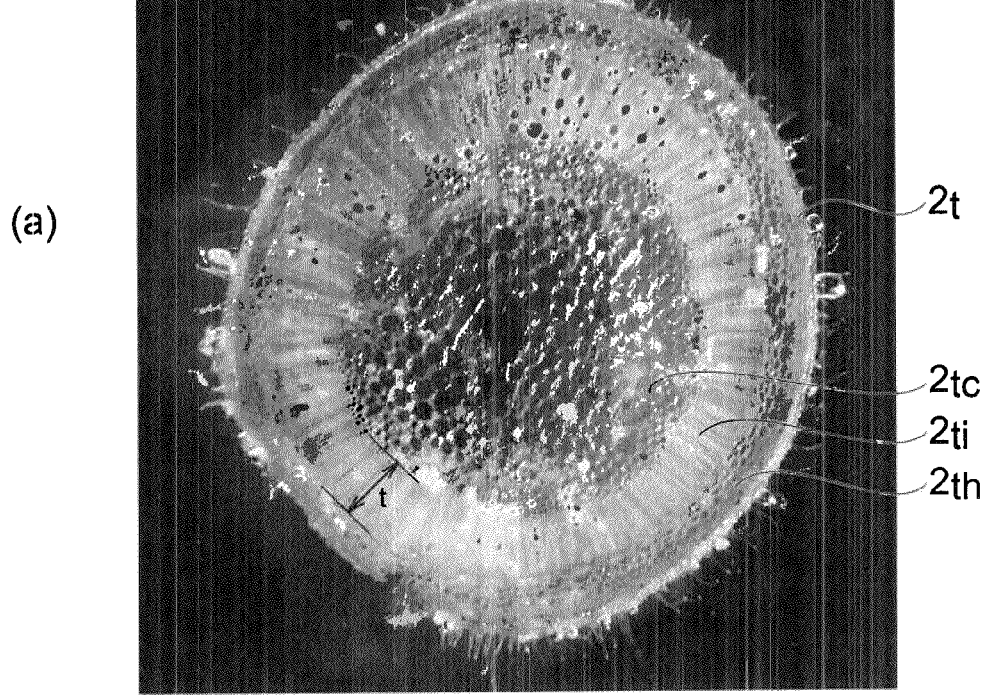
(b)
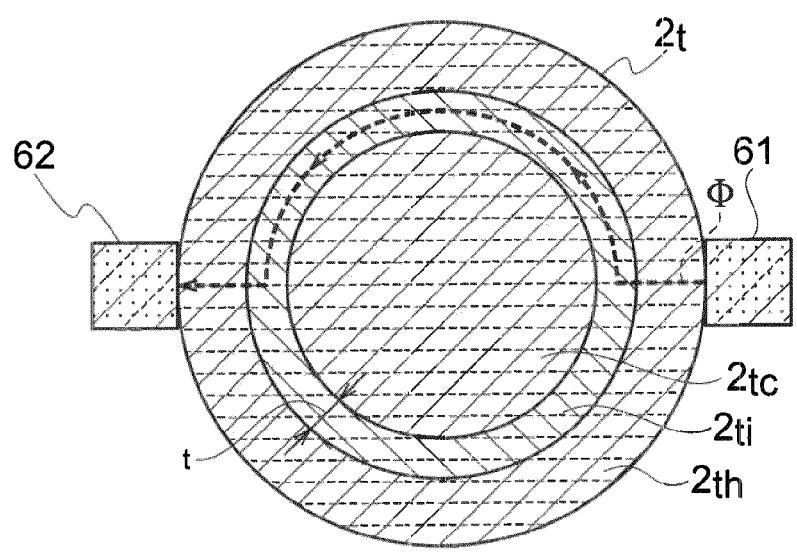

FIG. 24
(a)
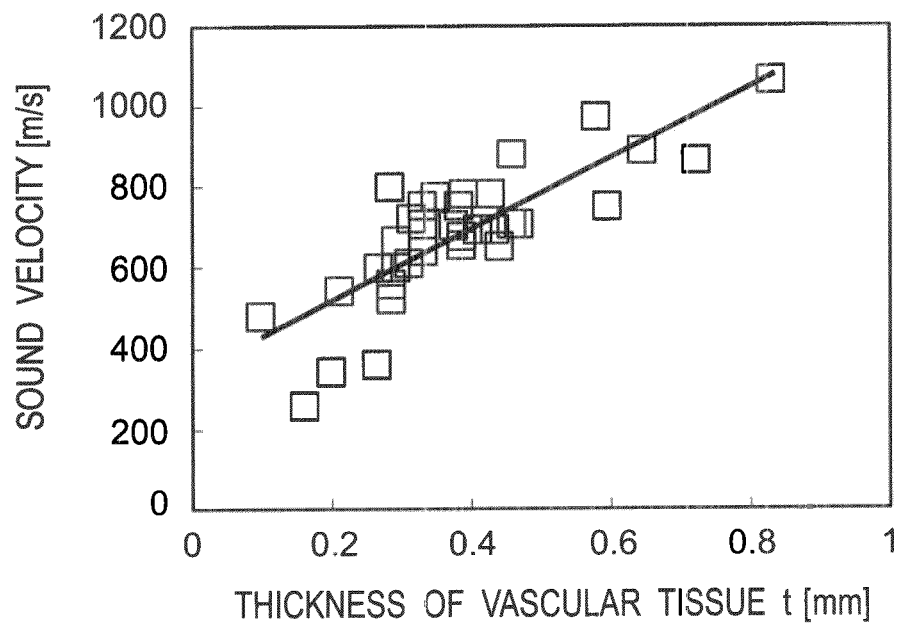
(b)
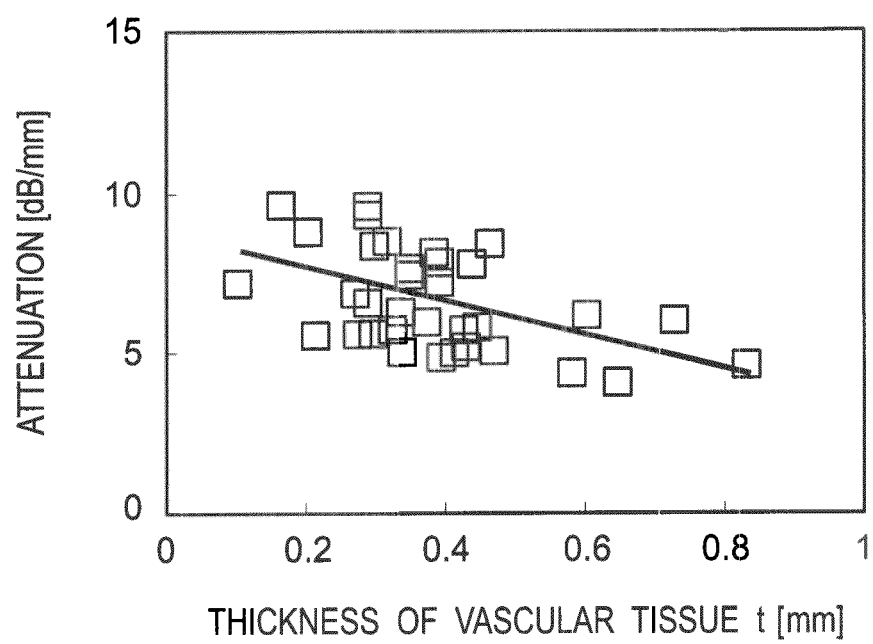

FIG. 25
(a)
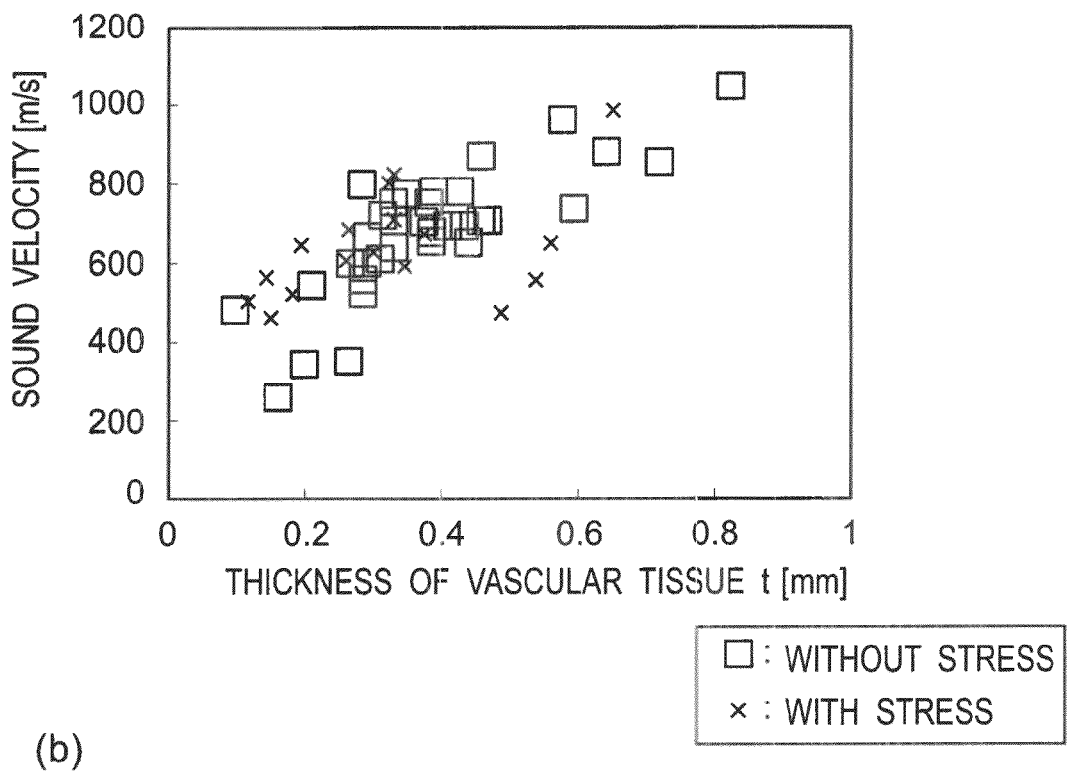
(b)
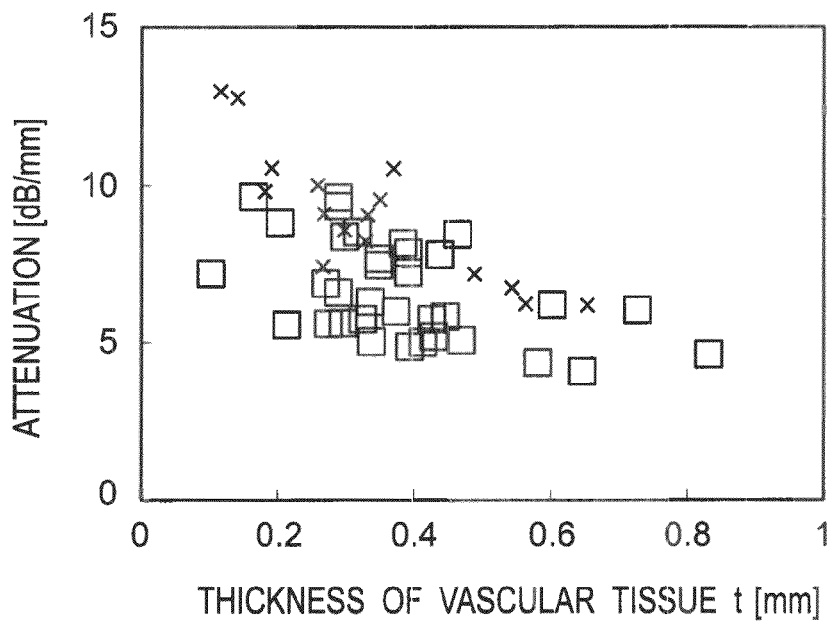

FIG. 28
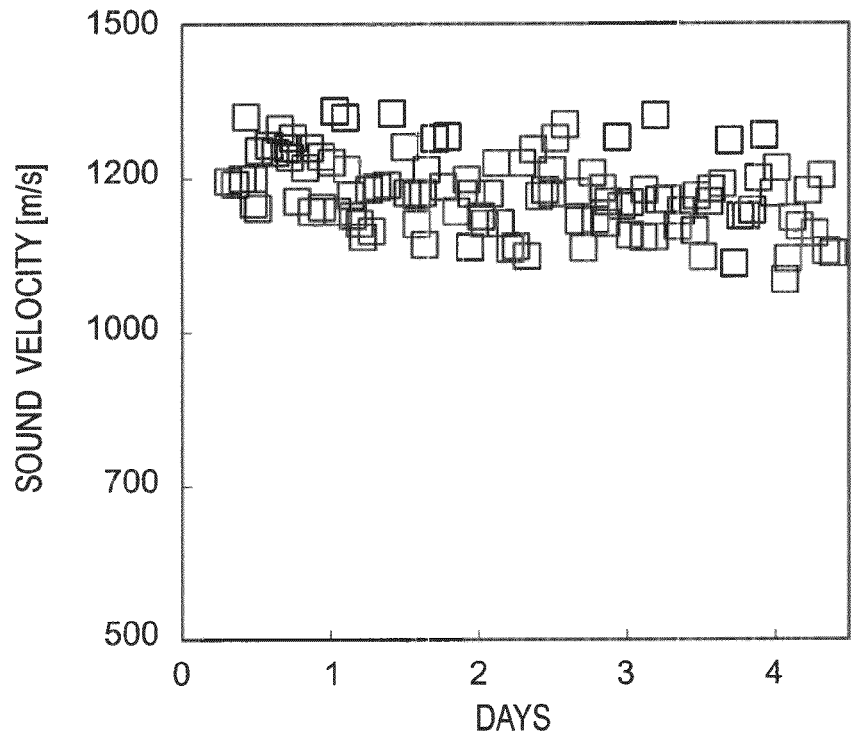
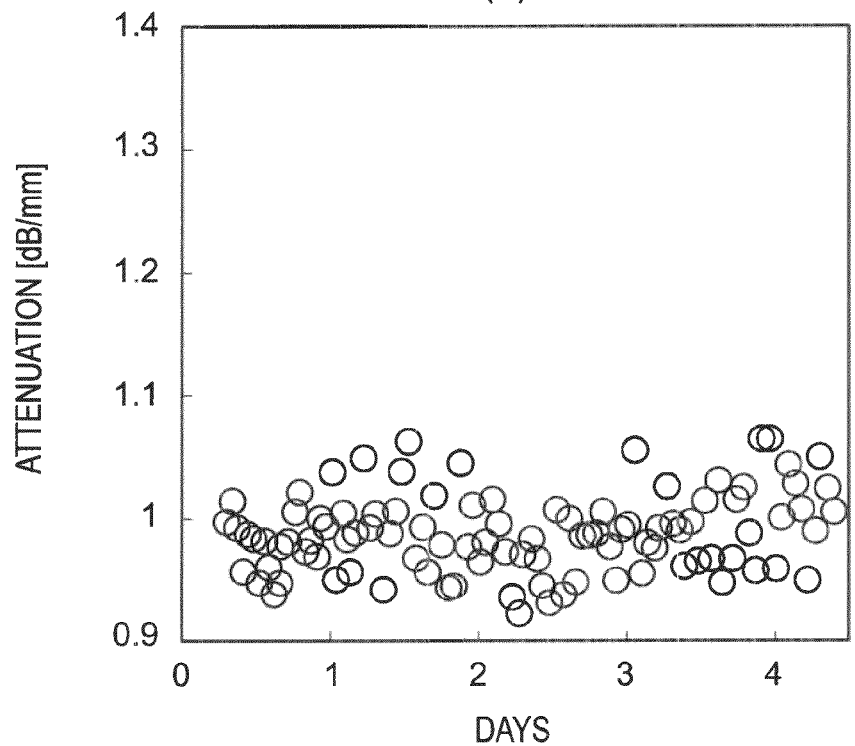

FIG. 29
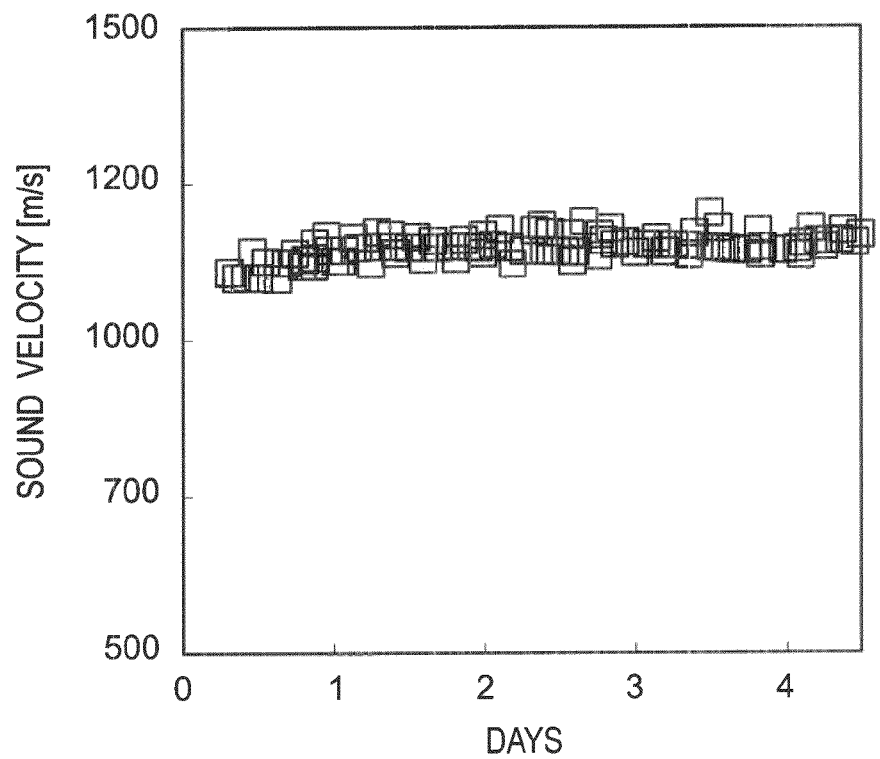
(a)
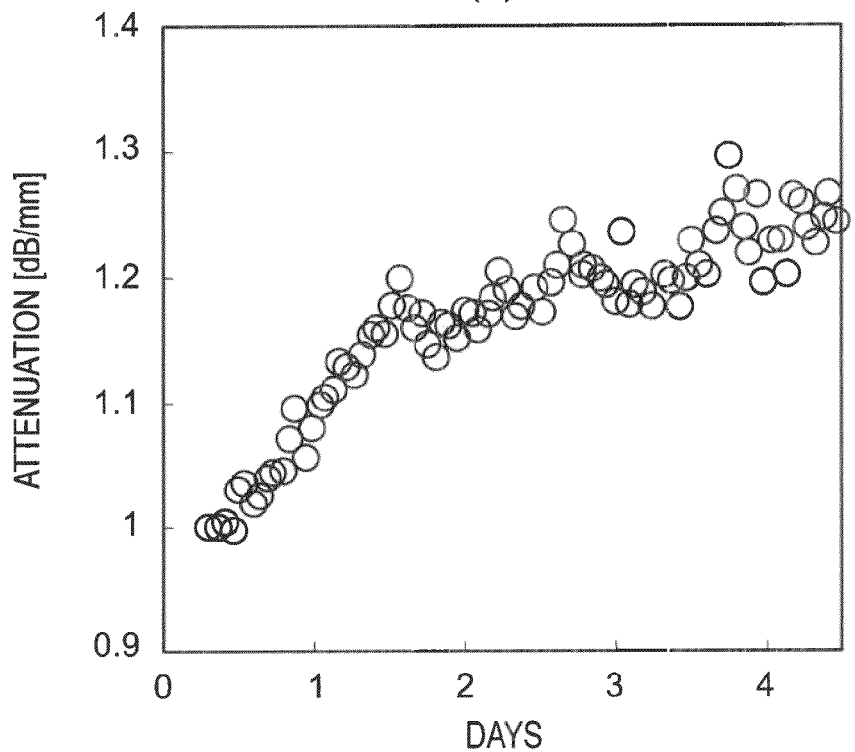
(b)

FIG. 30
(a)
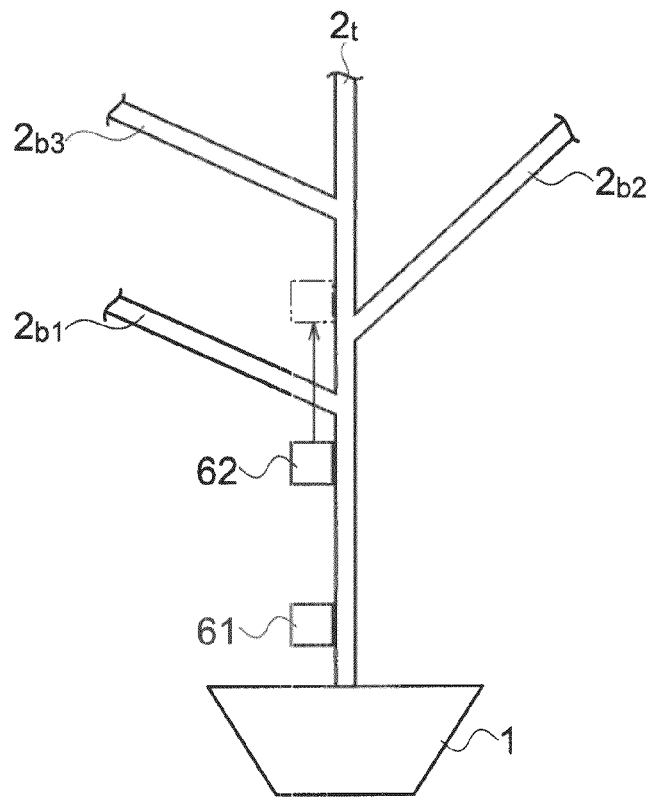
(b)
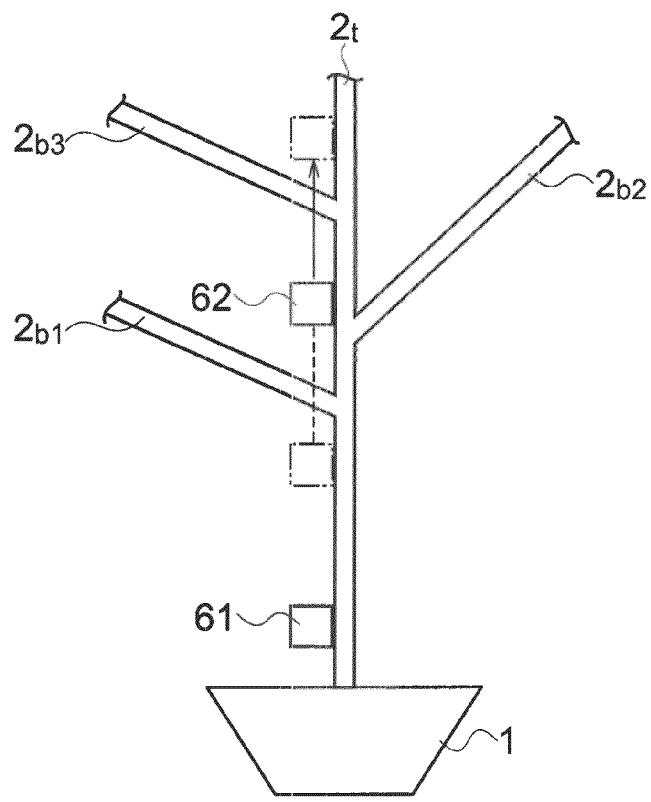

FIG. 36
(a)
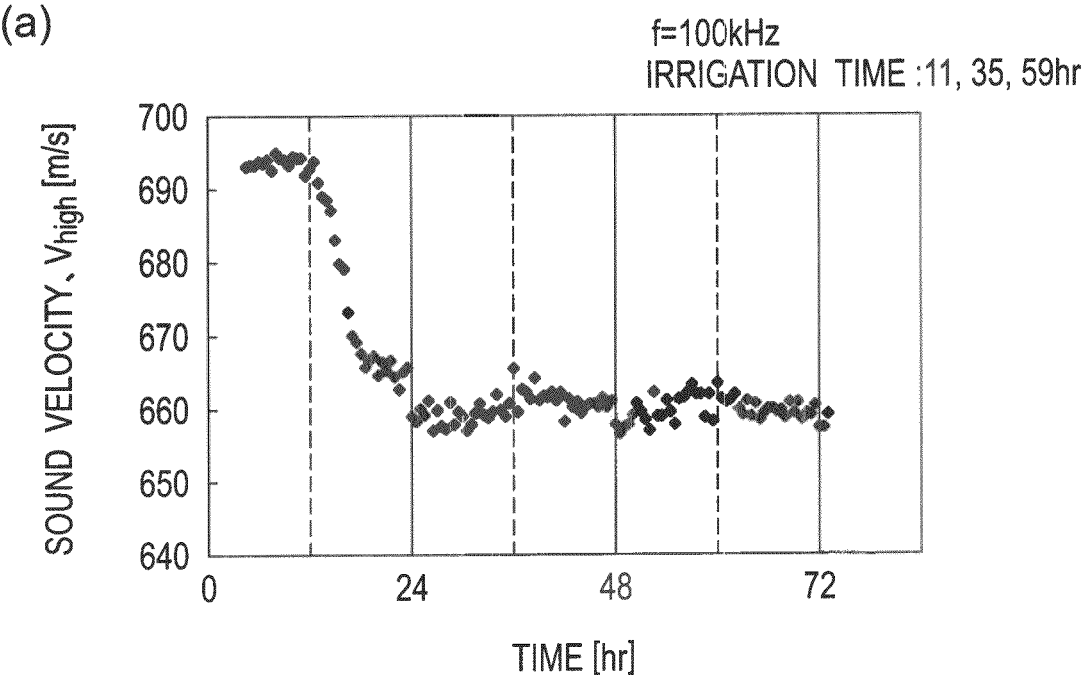
(b)
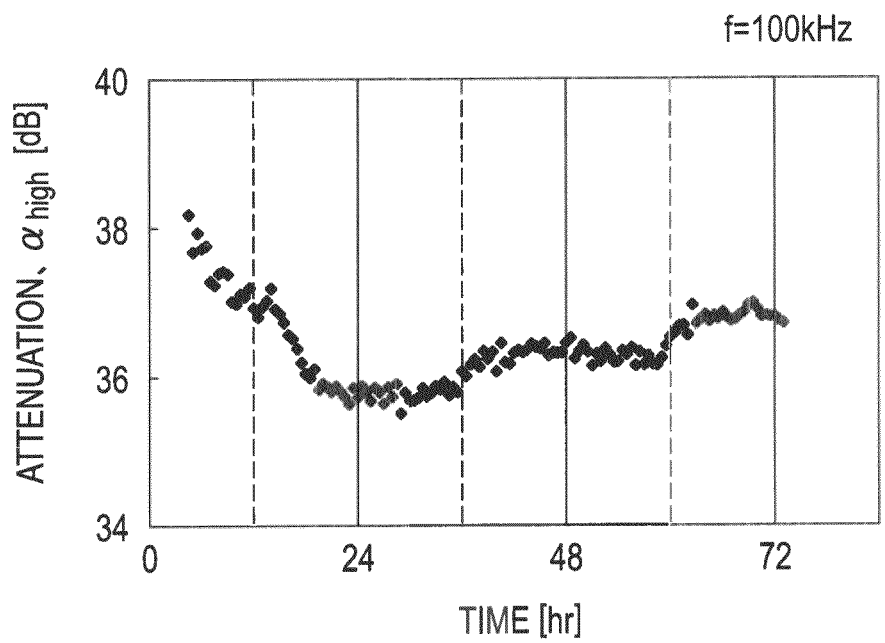

FIG. 40
(a)
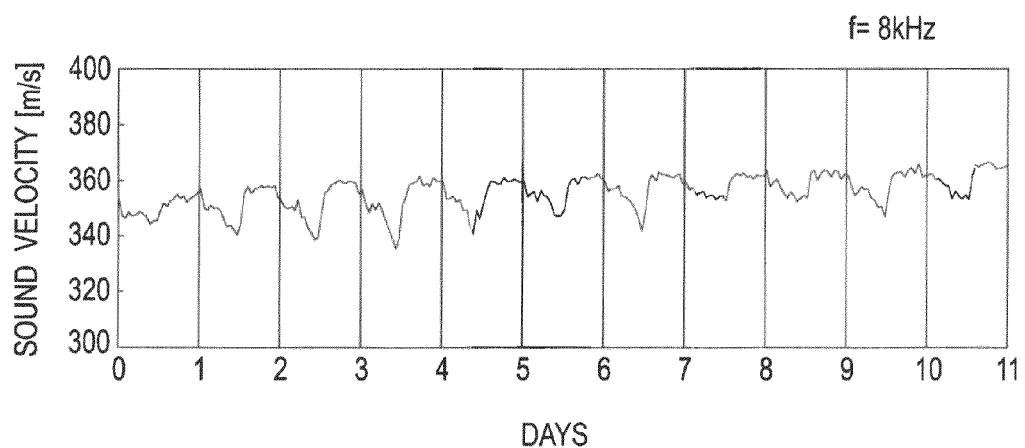
(b)
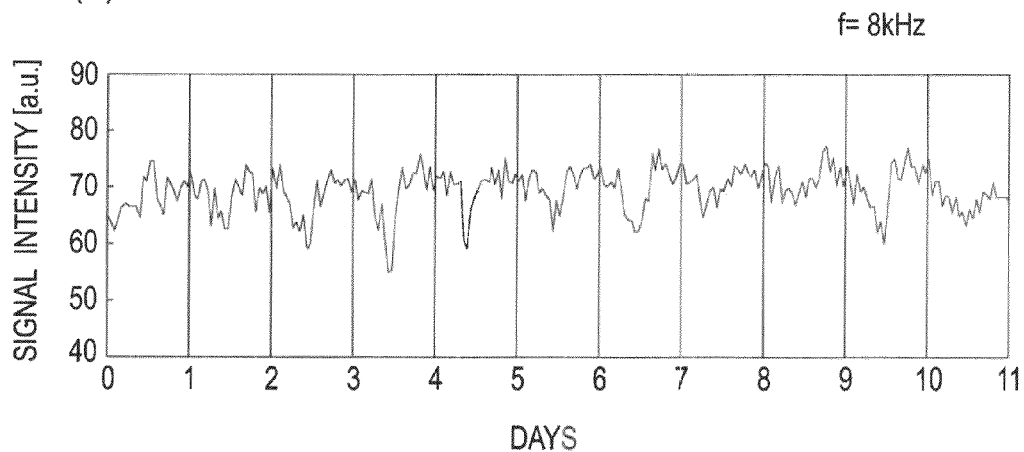

FIG. 41
(a)
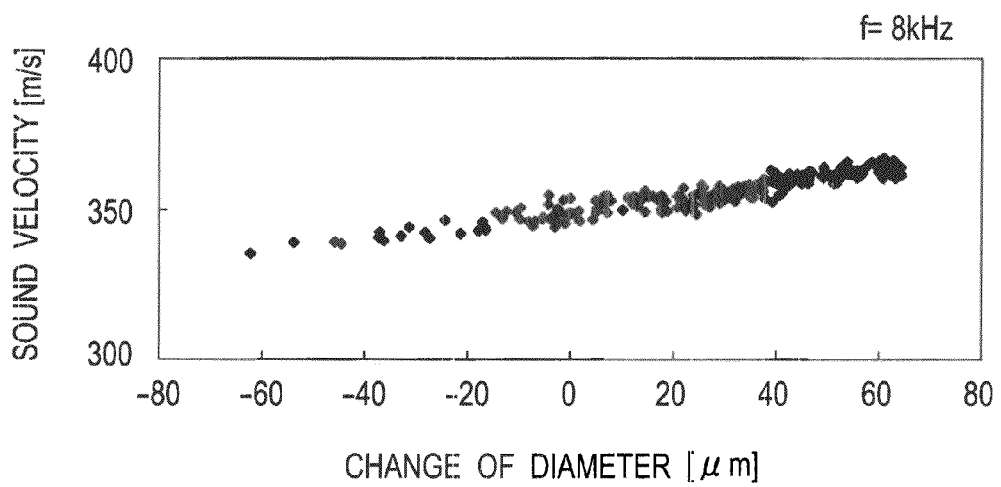
(b)
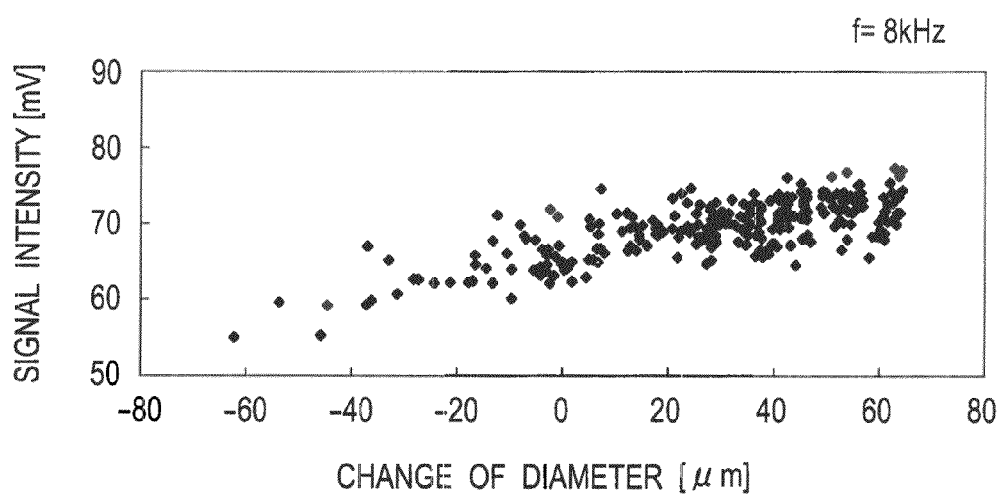

FIG. 43
(a)
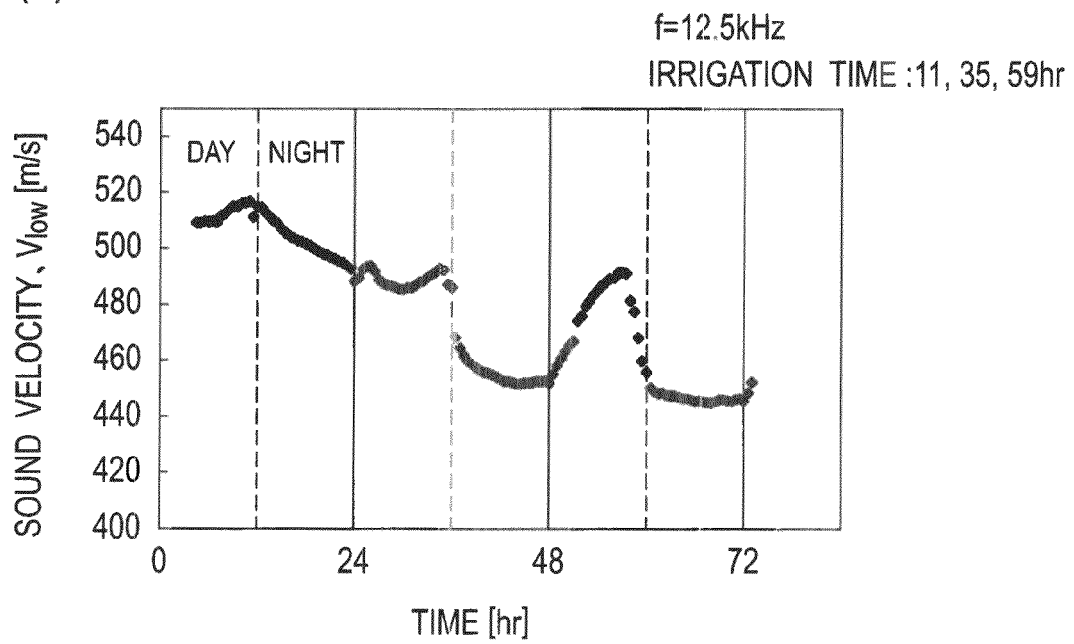
(b)
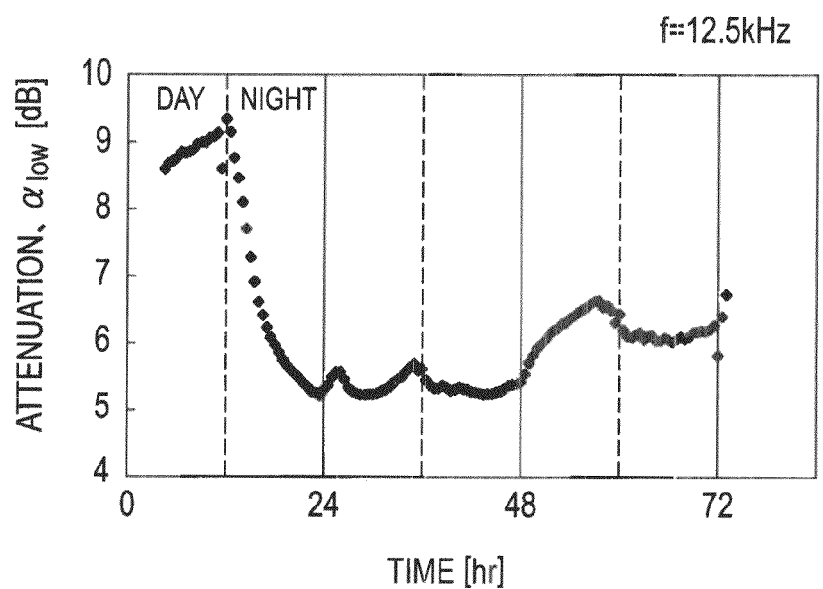

FIG. 44
(a)
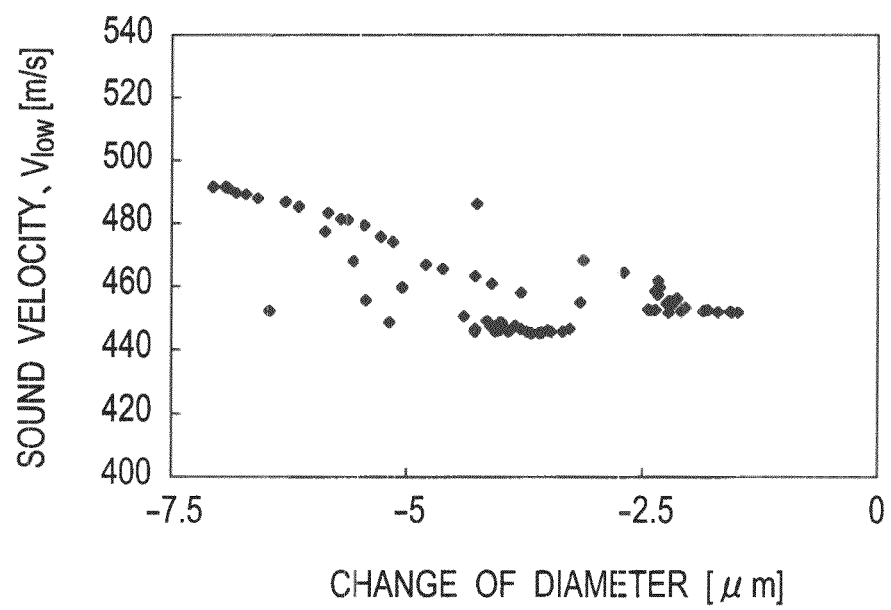
(b)
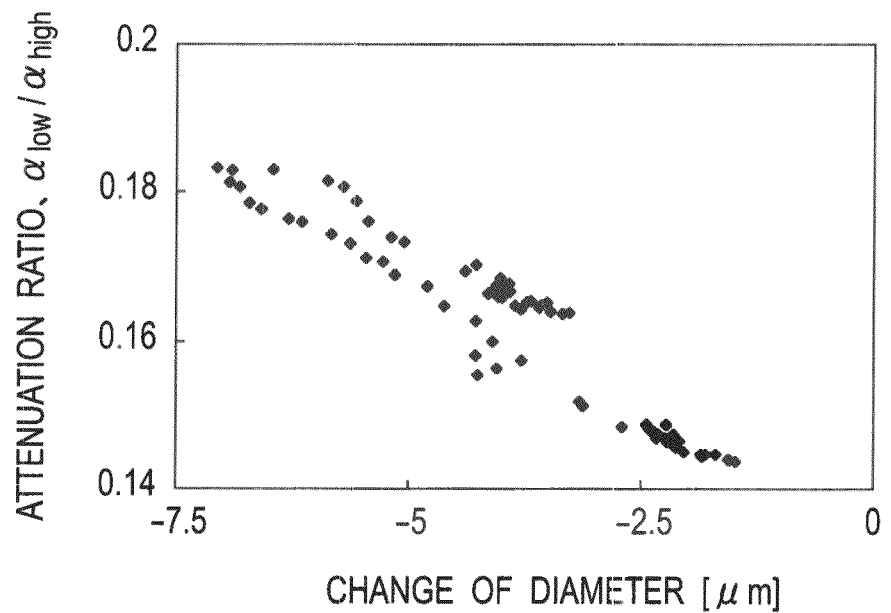

EVALUATION METHOD FOR BOTANICAL-INTEGRITY OF VASCULAR PLANT, IRRIGATING METHOD TO VASCULAR PLANT, FILM ELECTRET SENSOR AND FILM ECM ARRAY

FIELD OF THE INVENTION

The present invention pertains to an evaluation method for botanical-integrity of vascular plants such as crops, garden plants and the like, an irrigating method to the vascular plants based upon the evaluation method for botanical-integrity, and a film electret sensor and a film ECM array which are used in the evaluation method for botanical-integrity and the irrigating method.

DESCRIPTION OF THE RELATED ART

In a root of plants, there are an infinite number of root hairs, which makes it easy to absorb water and mineral nutrient dissolved in water. The absorbed water and mineral nutrient are sent into vessels (transport routes) of the roots, passed through the vessels of a stem and fed into leafs, flowers, fruits and the like. Since there are stomata in the leaf, water is transpired from the stomata. With the transpiration action of the leafs, the roots can further absorb water and mineral nutrient.

This vessel (transport route) of the plant serves as "vascular tissue", and the vascular tissue is implemented by "xylem" and "phloem". The xylem serves as a path for water and mineral nutrient, which is implemented by the vessel and parenchyma. The vessel serves as the tissue in which cells are longitudinally arranged and linked through holes on cell walls and create a canal. The phloem serves as a path for feeding organic nutrients made in leaves to a lower portion, and the phloem is implemented by the phloem and the parenchyma. The vascular tissue is the assembly of columnar tissues that longitudinally run through the stem of a so-called plant. Usually, vascular tissues line up in a constant array inside a stem, branch from the stem, enter into the leaves and the roots and extend up to tips and then finish at the tips. In many plants, those tissues collect in the constant array and form a bundle structure such as an aggregation of pipes and penetrate through the whole of the plant body. There is plurality of foregoing bundles, and when the section of the stem is viewed, the bundles are arranged in the inside of the plant body in the constant array. Each of organs protruding from the stem, such as leafs and the like, includes branches of the vascular tissue in the stem, and in the inside of the organs protruding from the stem, the branches of the vascular tissue further branch so as to serve as roles for feeding substances and mechanically supporting the organ.

There is a range of environmental factors in which the plant can grow under the best condition from a physiological viewpoint, depending on species of plants. Beyond the range of environmental factors, the growth of plants is hindered, the yield of plants is decreased, and the plant is disordered and blighted. A symptomatic state in which with the foregoing unsuitable environmental factor, the plant is physiologically inactive is referred to as "environmental stress", and "water stress", "temperature stress", "salt stress" and the like are listed as the environmental stress. As mentioned above, in the plant having the vascular tissue, the xylem serves as the transport route of water, and with a negative pressure generated by the transpiration in the daytime, water is pulled up to the leafs from the roots. When water stress, the salt stress, the growth difficulty of the root and the like disturbs the supply of water, the negative pressure of the xylem is increased, and the state in which the negative pressure is increased is referred to as "the state in which water stress is increased". When the situation of "increased water stress" continues, micro bubbles of air are finally injected into the xylem element, and the bubbles are released. The release of bubbles is referred to as "cavitation (cavity formation)", and a situation in which the cavitation causes the xylem element to be filled with air is "embolism" (refer to a non-patent document 1). The continuation of the embolism results in the increase in water flow resistance, and water supply performance is further decreased. Thus, the xylem element in the embolism state is recovered because water is again filled. The situation when water is filled again is referred to as "refilling".

In a normal state, a transpiration velocity and a water absorption velocity are equal, and water absorption velocity is proportional to a difference between a potential of soil water and a water potential of the leafs. When the transpiration velocity is increased and water potential is decreased, the difference between the potentials is increased, which makes water absorption velocity higher. The refilling is carried out even in the daytime in which the transpiration quantity is great, and the refilling causes water supply performance of the xylem to be kept. However, when water is not supplied to the soil, and the soil is dried, or when the drop in a ground temperature causes the roots to be cooled, and then, water absorption performance is decreased, or alternatively, when a high temperature low humidity or a strong wind causes the transpiration velocity to be made higher, the situation in which the transpiration velocity exceeds water absorption velocity, namely, water stress is occurred. When water stress is occurred, the stomata are closed, and a photosynthesis velocity and a leaf surface enlargement velocity are also made lower. Moreover, as water stress is increased and the number of the xylem elements, in which the cavitation is occurred, is increased, number of the xylem elements with permanent embolism state, in which the refillings cannot be carried out, is increased. In such situation, water supply performance is greatly decreased. Thus, the plant is curled up and begins to be wilted and blighted.

The precipitation or the amount of rainfall that has influence on the growth-condition of the plant changes depending on a weather, a season and a location. Under an environment such that the soil is sandy and the spread into underground is extremely fast, or the upward transpiration is vigorous, water necessary for the plant is not always included in the soil. Although natural plants have evolved to have a function adapted to the environment of a territory, because the cultivation of crops cannot be left to natural rainwater, depending on each environment of crops, any method is required to carry out the proper irrigation to the soil of crops.

Conventionally, the observation of the embolism state of the xylem element of the plant is carried out by cutting away an axis of the plant and quickly freezing the axis, and directly observing the cross-section of the axis through the use of a scanning electron microscope (SEM). Also, the detection of the embolism is carried out by observing water inside the axis of the plant, through the use of a nuclear magnetic resonance (NMR).

Also, as one of indexes of water stress, water potential is listed. A water potential $\phi_w$ of each element in the axis of the vascular plant is represented by the following Eq. (1), by using a spread potential $\phi_s$ and a pressure potential $\phi_p$, when a gravitation potential is ignored.

$$\phi_w = \phi_s + \phi_p \qquad (1)$$

Because most of the component of liquids in the xylem element is water, the spread potential $\phi_s$ can be ignored, and water potential $\phi_w$ in the xylem coincides with the pressure potential $\phi_p$. Water is pulled up through the xylem. Thus, when water is transpired from the leaf, the negative pressure is generated on the cell wall inside the leaf by surface tension. For this reason, water inside the xylem receives the negative pressure, and the negative pressure coincides with water potential $\phi_w$. The "water stress" is typically defined as the index that indicates the shortage quantity of water. In the plant, the shortage of water leads to the drop in water potential $\phi_w$ of the xylem. However, the drop in water potential $\phi_w$ implies the drop in the pressure potential $\phi_p$ (the increase in the value of the negative pressure of water inside the xylem). Hence, water potential virtually implies the value of the negative pressure of water in the xylem.

Water potential is mainly measured by a pressure chamber method. The pressure chamber method cuts away the leaf in a petiole (leaf stalk) portion, closes the leaf inside a chamber in a situation in which the cutoff plane of the petiole (leaf stalk) is exposed to the exterior, applies a pressure to the chamber, and measures the pressure at which water is sent from the xylem, and then calculates water potential.

PRIOR ART DOCUMENT

[Non-Patent Document 1]
A. M. Lewis and other two persons, "Collapse of water-stress emboli in the tracheids of Thuja occidentalis L.", Plant Physiol., 1994, Vol. 106, p 1639-1646

SUMMARY OF THE INVENTION

Subject to be Solved by the Invention

The SEM cross-section observation based on the quick freezing is the method of freezing water state inside the axis and directly observing the cross-section of the axis through the use of the SEM, and the SEM cross-section observation requires liquid nitrogen and an expensive apparatus that can carry out the SEM observation in the quickly frozen state. Thus, the cross-section of the axis cannot be directly measured by SEM in outdoors. On the other hand, the NMR is the technique that visualizes the structure inside the axis, by using the fact that a nuclear magnetic resonance effect is changed by water inside the axis, however the NMR apparatus is very expensive. In particular, although the NMR apparatus that can carry out the measurement in the outdoors is under development, the measurement in the outdoors takes a time to install and set the NMR apparatus. Moreover, the resolution is only an order of sub millimeters. Hence, the detection is impossible unless the embolism is densely generated. For this reason, in the case of the plant that is weak against water stress, it is difficult to detect the embolism.

Also, water potential measurement based on the pressure chamber method is required to cut off the leaf. Thus, the number of the measurements is limited, which disables the consecutive measurement. Also, a pressure bomb for pressuring is required. Thus, at the time of the outdoor measurement, the number of the measurements is further limited.

In view of the above-mentioned problems, an object of the present invention is to provide the evaluation method for botanical-integrity of the vascular plant, which measures the risk level of the embolism, the relative concentration of the embolism, water potential, the turgor pressure of the cell and the like, in outdoors, without using the expensive apparatus, and consequently evaluates the degree of botanical-integrity in vascular plant, and further provide the irrigating method that can determine an irrigation timing and an irrigation quantity to the vascular plant, with the evaluation method for botanical-integrity as the base, and the film electret sensor and the film ECM array that are used in the evaluation method for botanical-integrity and the irrigating method.

In order to achieve the above-mentioned object, a first aspect of the present invention inheres in a method for evaluating degree of botanical-integrity in vascular plant, including (a) measuring an occurrence frequency of elastic waves generated by cavitations in vascular tissues in vascular plant, before and after a change in water stress to the vascular plant, respectively by an elastic wave reception sensor fixed to an axis of the vascular plant, (b) calculating a change rate of the occurrence frequency, from the occurrence frequency of the elastic wave measured before and after the change, respectively, and (c) determining whether or not an embolism in the vascular tissue arrives at an unrecoverable level of the embolism, from the calculated change rate, and then, botanical-integrity of the vascular plant is evaluated, on the basis of the level of the embolism.

A second aspect of the present invention inheres in a method for evaluating degree of botanical-integrity in vascular plant, including (a) generating a burst acoustic wave of a wavelength longer than a diameter of an axis of vascular plant assigned as a measuring target, by an acoustic vibrator fixed to the axis, (b) measuring a guide wave generated by the burst acoustic wave and propagated through a whole of the axis, by an elastic wave reception sensor fixed to the axis, (c) determining a measured sound velocity and a measured sound velocity attenuation rate of the guide wave, from the measurement, and (d) comparing a reference sound velocity and a reference attenuation rate of a guide wave propagated through an entire axis of a reference vascular plant in a healthy botanical state with the measured sound velocity and the measured attenuation rate, respectively, the reference vascular plant is equal in species to the measuring target, the reference sound velocity and the reference attenuation rate is pre-examined with the reference vascular plant, and then, a water state of the measuring target is evaluated.

A third aspect of the present invention inheres in a method for irrigating vascular plant, including (a) measuring an occurrence frequency of elastic waves generated by cavitations in vascular tissues in vascular plant, before and after a change in water stress to the vascular plant, respectively, by an elastic wave reception sensor fixed to an axis of the vascular plant, (b) calculating a change rate of the occurrence frequency, from the occurrence frequency of the elastic wave measured before and after the change, respectively, (c) determining whether or not an embolism of the vascular tissue arrives at an unrecoverable level, from the calculated change rate, and (d) determining an irrigation timing and an irrigation quantity to the vascular plant, using the determined result as an index.

A fourth aspect of the present invention inheres in a method for irrigating vascular plant, including (a) attaching an acoustic vibrator and an acoustic receiver to an axis of vascular plant having an annular vascular tissue, and measuring an attenuation rate of an acoustic wave propagated through the vascular tissue and then determining an measured attenuation rate, (b) dividing the measured attenuation rate by a value of a reference attenuation rate so as to calculate an attenuation rate ratio, the reference attenuation rate is determined by an attenuation rate of the acoustic wave propagated through the vascular tissue measured in a case that a sufficient irrigation is carried out to the vascular plant in advance, and (c) determining an irrigation timing and an irrigation quantity to the vascular plant, with the calculated attenuation rate ratio as an index.

A fifth aspect of the present invention inheres in a film electret sensor configured to flexibly fixed, conforming to a shape of an axis of vascular plant, and to measure an occurrence frequency of elastic waves generated by cavitations in vascular tissues in the vascular plant, before and after a change in water stress being applied to the vascular plant, respectively. Namely, the film electret sensor pertaining to the fifth aspect of the present invention, the film electret sensor encompasses (a) a vibration film protection film implemented by a flexible resin layer in contact with the axis of the vascular plant, (b) a vibration electrode film in contact with the vibration film protection film, (c) an electret-film opposite to the vibration electrode film in which an element space is established between the electret film and the vibration electrode film, (d) a back electrode film in contact with a bottom surface of the electret film, (e) a gap insulation layer being inserted so as to vertically separate the element space, providing a plurality of micro gaps, each having an interval between 10 nm and 40 μm, in the inside of the element space, and (f) an amplifier electrically connected between the vibration electrode film and the back electrode film. And, in the film electret sensor pertaining to the fifth aspect of the present invention, an effective surface roughness of each of surfaces defining the plurality of micro gaps is less than or equal to $1/10$ of a gap width of the element space respectively.

A sixth aspect of the present invention inheres in a film ECM array encompassing a plurality of elements, the film ECM array is configured to flexibly fixed conforming to a shape of an axis of vascular plant, and to measure an occurrence frequency of elastic waves generated by cavitations in vascular tissues in the vascular plant, before and after a change in water stress being applied to the vascular plant. Namely, each of elements implementing the film ECM array pertaining to the sixth aspect of the present invention, encompasses (a) a vibration film protection film implemented by a flexible resin layer in contact with the axis of the vascular plant, (b) a vibration electrode film in contact with the vibration film protection film, (c) an electret film opposite to the vibration electrode film in which an element space is established between the electret film and the vibration electrode film, (d) a back electrode film in contact with a bottom surface of the electret film, and (e) a gap insulation layer being inserted so as to vertically separate the element space, providing a plurality of micro gaps, each having an interval between 10 nm and 40 μm, in the inside of the element space. And, in the film ECM array pertaining to the sixth aspect of the present invention, the plurality of the elements are connected to each other so that the vibration electrode films of the respective elements and the back electrode films of the respective elements exhibit a common electrodes, respectively, the plurality of the elements are arrayed on a common flexible base, and the back electrode films are connected to a common amplifier so as to form an array implemented by a plurality of elastic wave reception sensors. Furthermore, in the film ECM array pertaining to the sixth aspect of the present invention, in each of the elements, an effective surface roughness of each of surfaces defining the plurality of micro gaps, respectively, is less than or equal to $1/10$ of a gap width of the element space.

A seventh aspect of the present invention inheres in a film ECM array configured to be fixed to and wound around an axis of vascular plant having an annular vascular tissue, conforming to a shape of the axis, integrating an acoustic vibrator and an acoustic receiver in the film ECM array, the acoustic vibrator and the acoustic receiver being configured to measure an attenuation rate of an acoustic wave propagated through the vascular tissue. That is, the film ECM array pertaining to the seventh aspect of the present invention encompasses (a) a flexible base having a plurality of penetration holes, configured to be wound around the axis of the vascular plant, (b) a common electret film in contact with a top surface of the flexible base, (c) a plurality of back electrode films provided in the plurality of penetration holes, each of the back electrode films being arrayed independently so as to contact with a part of a bottom surface of the electret film, (d) a plurality of amplifiers provided in the plurality of penetration holes, each of the amplifiers being arrayed independently so as to connect to the back electrode films, (e) a plurality of vibration electrode films opposite to each of the electret films, so as to establish a plurality of independent element spaces, above each of the penetration holes, respectively, and (e) a plurality of gap insulation layers, each of the gap insulation layers is inserted to vertically separate the respective element spaces so as to provide a plurality of micro gaps, each of the micro gaps having an interval between 10 nm and 40 μm. And, in the film ECM array pertaining to the seventh aspect of the present invention, in each of the element spaces serve as the acoustic vibrator and the acoustic receiver, and an effective surface roughness of each of surfaces defining the plurality of micro gaps, respectively, is less than or equal to $1/10$ of a gap width of the element space.

Effectiveness of the Present Invention

According to the present invention, it is possible to provide the evaluation method of degree of botanical-integrity in vascular plant, which evaluates the degree of botanical-integrity in vascular plant, by measuring the risk level of the embolism, the relative embolism density, water potential, the turgor pressure of the cell and the like, in outdoors without using an expensive apparatus, and further provide the irrigating method that can determine the irrigation timing and the irrigation quantity to the vascular plant, with the evaluation method for evaluating degree of botanical-integrity as the base, and the film electret sensor and the film ECM array that are used in the evaluation method for evaluating degree of botanical-integrity and the irrigating method.

BRIEF DESCRIPTION OF THE DRAWINGS

FIG. 11 are views illustrating the change in an AE occurrence frequency after the disconnection of the axis, for a case (FIG. 11(a)) that water stress in the daytime is small and a case (FIG. 11(b)) that water stress in the nighttime is small.

FIG. 12 are views illustrating the change in the AE occurrence frequency after the disconnection of the axis, for a case (FIG. 12(a)) that water stress in the daytime is great and a case (FIG. 12(b)) that water stress in the nighttime is great.

FIG. 14(a) is a sectional view taken from an XIV-XIV direction on a lateral side view in FIG. 14(b).

FIG. 22(a) is a sectional view illustrating the axis of a miniature tomato as one example of the vascular plant, and FIG. 22(b) is a schematic cross-sectional view illustrating a manner in which in the evaluation system of the botanical-integrity in vascular plant and the irrigating system according to a seventh embodiment, when an acoustic wave of a wavelength sufficiently longer than a thickness of the vascular tissue is entered from a surface of a main axis, a guide wave φ is generated in the vascular tissue and annularly propagated through the vascular tissue.

FIG. 24(a) is a view illustrating a relationship between the thickness of the vascular tissue and a sound velocity, and FIG. 24(b) is a view illustrating a relationship between the thickness of the vascular tissue and an attenuation rate.

FIG. 25(a) is a view illustrating a fact that as for the relationship between the thickness of the vascular tissue and the sound velocity, a significant difference is not observed between the cases of the presence and absence of water stress, and FIG. 25(b) is a view illustrating a fact that the attenuation rate is high in the case with water stress, as compared with the case without water stress.

FIG. 28 is a view illustrating a fact in which a change is not substantially observed in the variation per day of the sound velocity and attenuation rate of the guide wave that is propagated through the vascular tissue, in the case without water stress, in the evaluation system of the botanical-integrity in vascular plant and the irrigating system according to the seventh embodiment.

FIG. 29(a) is a view illustrating a fact in which in the case with water stress, the sound velocity of the guide wave propagated through the vascular tissue is not changed even if there is the drop in the soil water caused by the variation per day, and FIG. 29(b) is a view illustrating a fact in which in the case with water stress, the attenuation rate of the guide wave propagated through the vascular tissue is increased by the variation per day.

FIG. 30 is a schematic view describing a fact in which in the seventh embodiment of the present invention, in order to measure the sound velocity and attenuation rate of the guide wave propagated through the vascular tissue, a placement position of a single acoustic receiver is changed to detect the guide waves at a plurality of points.

FIG. 36(a) is a view illustrating the variation per day in the sound velocity of the acoustic wave (guide wave) propagated through the vascular tissue of a strawberry tree, in a process for recovering water stress from a state in which the severe water stress is given, in order to describe the evaluating method of water state of the plant according to the seventh embodiment of the present invention, and FIG. 36(b) is a view illustrating the variation per day in the attenuation rate of the acoustic wave propagated through the vascular tissue of the strawberry tree.

FIG. 40(a) is a view illustrating the variation per day in the sound velocity of the acoustic wave (guide wave) propagated through the whole of the axis of the miniature tomato, in the evaluating method of water state of the plant, according to the ninth embodiment, and FIG. 40(b) is a view illustrating the variation per day in the signal magnitude of the acoustic wave.

FIG. 41(a) is a view describing a relationship between the change in the axis diameter of the miniature tomato and the change in the sound velocity of the acoustic wave (guide wave) propagated through the whole of the axis, in the evaluating method of water state of the plant according to the ninth embodiment, and FIG. 41(b) is a view describing a relationship between the change in the axis diameter of the miniature tomato and the change in the signal magnitude of the acoustic wave (guide wave) propagated through the whole of the axis.

FIG. 43(a) is a view illustrating the variation per day in the sound velocity of the acoustic wave (guide wave) propagated through the whole of the axis of the strawberry tree, in the process for recovering water stress from the state in which the sever water stress is given, in order to describe the evaluating method of water state of the plant according to the ninth embodiment of the present invention, and FIG. 43(b) is a view illustrating the variation per day in the attenuation rate of the acoustic wave.

FIG. 44(a) is a view describing a relationship between the change in the axis diameter of the strawberry tree and the change in the sound velocity of the acoustic wave (guide wave) propagated through the whole of the axis, in the evaluating method of water state of the plant according to the ninth embodiment, and FIG. 44(b) is a view describing a relationship between the change in the axis diameter of the strawberry tree and the change in the attenuation rate of the acoustic wave (guide wave) propagated through the whole of the axis.

DETAILED DESCRIPTION OF THE EMBODIMENTS

Figure 1:
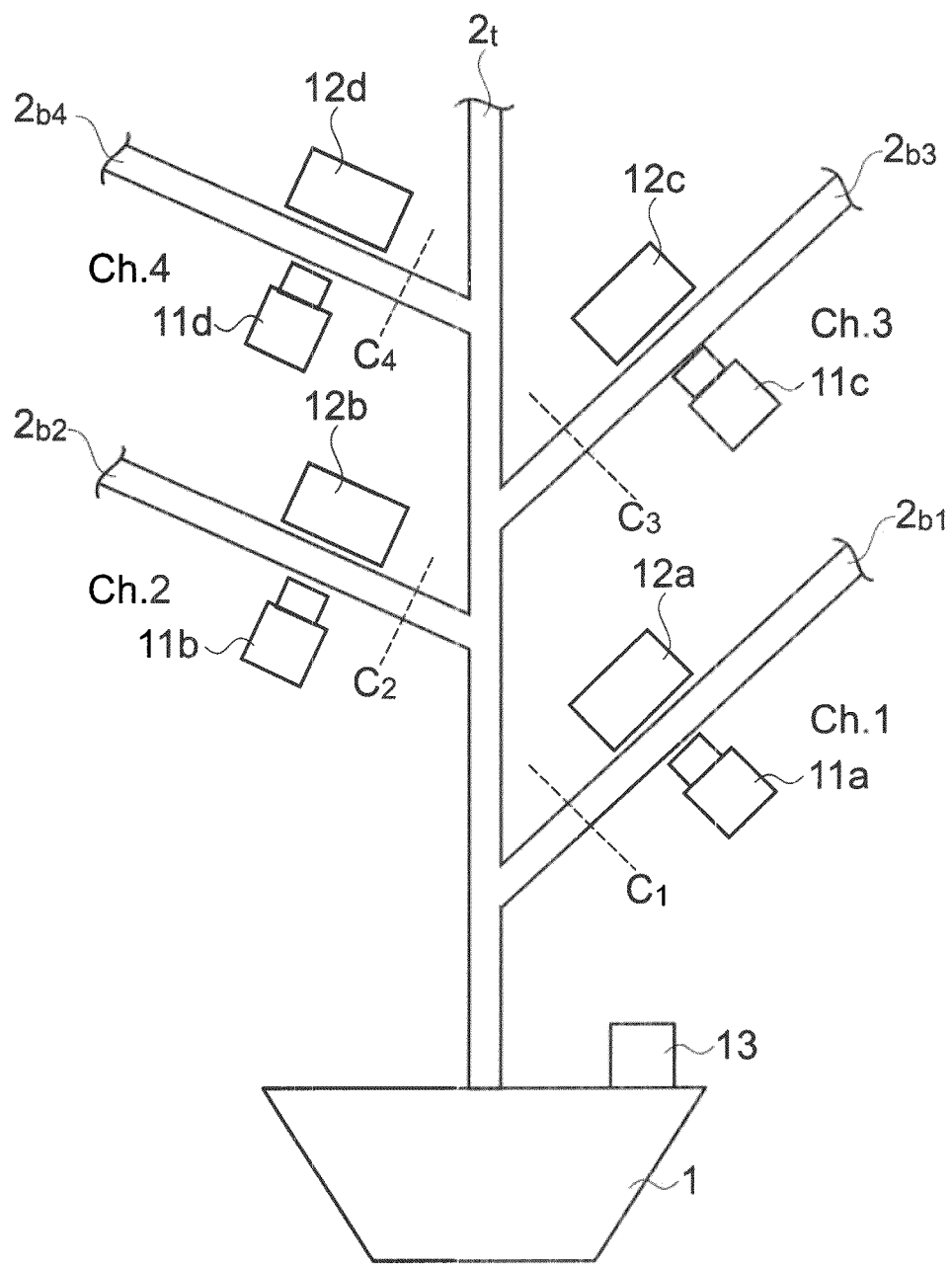
FIG. 1 is a schematic view describing a rough configuration of an evaluation system of the botanical-integrity in vascular plant and an irrigating system, according to a first embodiment of the present invention.

The first to eleventh embodiments of the present invention will be described below with reference to the drawings. In the following notifications on the drawings, the same or similar reference numerals are assigned to the same or similar parts and elements. However, the drawings are only diagrammatic. Then, attention should be paid to the fact that the relations between thicknesses and planer dimensions, the ratios between thicknesses of respective layers, and the like differ from the actual values. Also, the thicknesses, dimensions and the like of the respective layers, which are exemplified and described in the first to eleventh embodiments, should not be limitedly construed, and the specific thicknesses and dimensions should be determined by considering the following explanations. In particular, attention should be paid to the fact that the thicknesses, dimensions and the like can be determined to various values, on the basis of design schemes, requested properties and detailed requested particulars. Also, naturally, the portion in which the relations and ratios between the mutual dimensions are different is included even between the mutual drawings.

Also, the first to eleventh embodiments, which will be described below, only exemplify the apparatuses and methods to specify the technical idea of the present invention. As for the technical idea of the present invention, the material qualities, shapes, structures, arrangements and the like of the configuration parts are not limited to the followings. Various changes can be added to the technical idea of the present invention, within the technical scopes prescribed by Claims.

First Embodiment

Native plants are taxonomically classified into the vascular plant and the nonvascular plant, such as fungi, algae, mosses and the like. The vascular plant is characterized by having the vascular tissue serving as the vessel through which water flows, and includes the pteridophyte, such as Pteridophyta, Licopodiophyta, Equisetum, Psilotophyta and the like, and the Gymnospermae and the Angiosperm. Most of grasses and trees are classified into the vascular plant. The vascular tissue is implemented by walls that have many dents, or serves as a channel which is surrounded with the wall plane of the same kind and in which water is sent and received between the cells.

As illustrated in FIG. 1, each of the evaluation system of the botanical-integrity for vascular plant according to the first embodiment of the present invention and the irrigating system based on this botanical-integrity evaluation system targets the vascular plant of a single axis branch, which has a main axis (stalk) $2_t$ that uprightly stands on a ground from the soil stored in a flower pot 1 and a plurality of side axes (branches) $2_{b1}, 2_{b2}, 2_{b3}, 2_{b4}$, - - - branched from the main axis $2_t$. Although the illustration is omitted in FIG. 1, as can be also understood from FIGS. 16 to 17 that will be described later and the like, in this Specification, those including the petiole (leaf stalk), the vein and the like in addition to the main axis $2_t$ and the side axes $2_{b1}, 2_{b2}, 2_{b3}, 2_{b4}$, - - - are defined as "axis". A soil water sensor 13 is placed on the surface of the soil placed in the flower pot 1.

In the irrigating system according to the first embodiment, an elastic wave reception sensor 11a is placed through a rubber sheet 12a on the side axis $2_{b1}$, an elastic wave reception sensor 11b is placed through a rubber sheet 12b on the side axis $2_{b2}$, an elastic wave reception sensor 11c is placed though a rubber sheet 12c on the side axis $2_{b3}$, and an elastic wave reception sensor 11d is placed through a rubber sheet 12d on the side axis $2_{b4}$. An acoustic emission (AE) implies a phenomenon in which sound generated when a solid is deformed or broken is emitted as an elastic wave. In the irrigating system according to the first embodiment, as illustrated in FIG. 7(b), the elastic waves generated when the micro bubbles of the air are injected into the vessel (or tracheid) 201 are detected by the elastic wave reception sensors 11a, 11b, 11c, 11d, - - - . The placed positions of the elastic wave reception sensors 11a, 11b, 11c, 11d, - - - may be not only on the side axes $2_{b1}, 2_{b2}, 2_{b3}, 2_{b4}$, - - - but also on the main axes $2_t$ and the petiole (leaf stalk)s. In the case of the petiole (leaf stalk), the elastic wave (AE) is easily attenuated, as compared with the side axes $2_{b1}, 2_{b2}, 2_{b3}, 2_{b4}$, - - - , and the main axis $2_t$. Thus, although the measurement sensibility is dropped, the damage to the plant is small.

Figure 7:
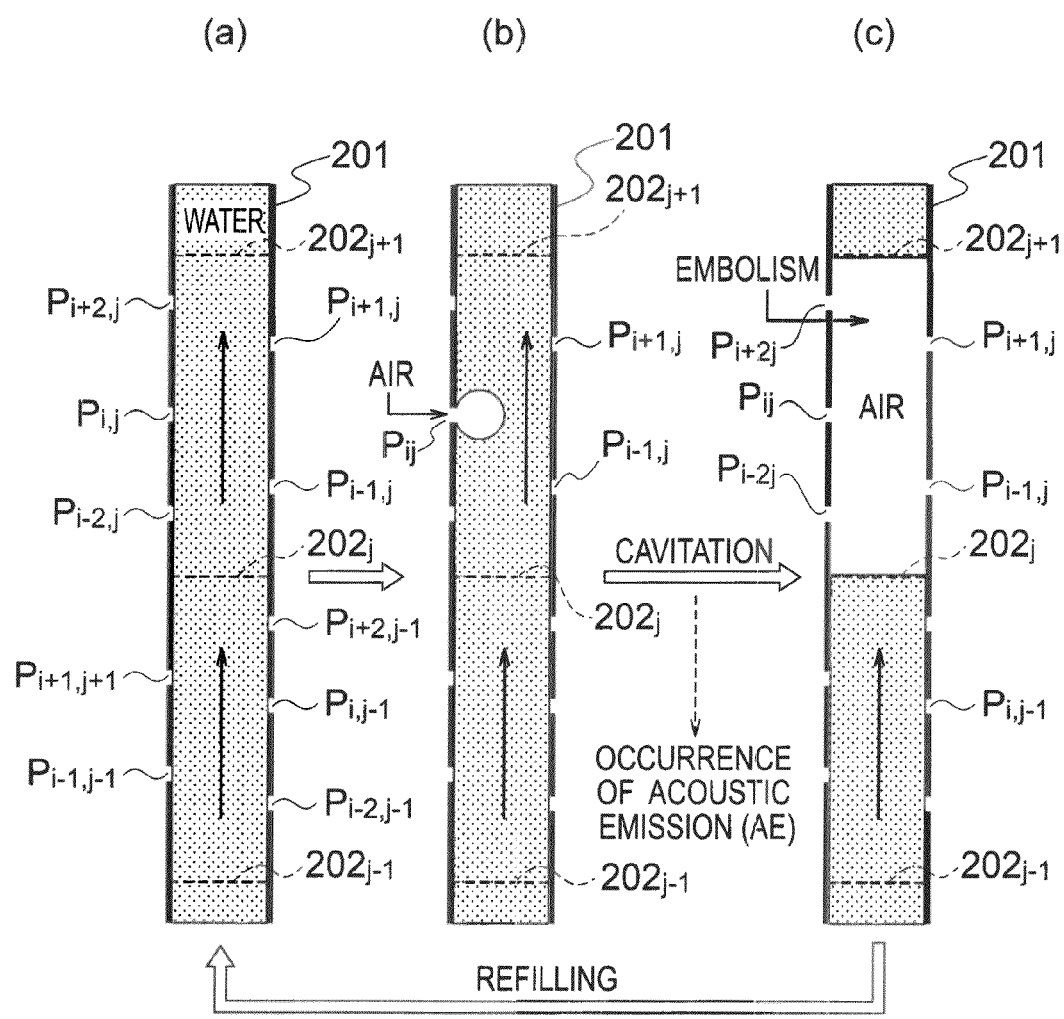
FIG. 7 is a schematic view describing a manner in which, when micro bubbles of air are injected into a vessel, cavitation is occurred, thereby emitting an AE wave, and an embolism.

As already mentioned in the introduction paragraph, the vascular tissue has: the "xylem" that serves as the path of water and mineral nutrients absorbed up from the root; and the "phloem" that serves as the path of the organic nutrients photosynthesized in the leaf. The xylem is implemented by assembly such that a plurality of vessels (or tracheids) 201 illustrated in FIG. 7 are collected and xylem fibers, xylem tissues and the like are further included. The phloem is implemented by assembly such that a plurality of phloem tubes are collected and phloem fibers, phloem parenchyma are further included. That is, the portion in which the many vessels are collected is the xylem. In the axis such as the stem of the vascular plant and the like, the xylems are arranged in the shape of a ring.

FIG. 7 schematically illustrates one of the plurality of vessels implementing the xylem of the vascular tissue. As illustrated in FIG. 7(a), the vessel 201 serves as the transport route of water, and with the negative pressure generated by the transpiration in the daytime, water is pulled to the leafs from the roots. The vessel 201 is made of lignified dead cells and forms the main portion of the xylem in the vascular tissue and further serves as the mechanical tissue for supporting the plant body. In the vessel 201, the cylindrical or polygonal elongated cells are linked longitudinally in one line through cell walls $202_{j-1}, 202_j, 202_{j+1}$, - - - , as illustrated in FIG. 7(a). However, the protoplasm inside the cell walls $202_{j-1}, 202_j, 202_{j+1}$, - - - serving as the up-to-bottom partitions and the cells are dissipated, and holes are opened, which substantially exhibits the long tube. The cell walls forming the vessel 201 are lignified such that lignin is accumulated to increase the thickness, in order to enable water solution to easily pass and make the strength high. The thickened portion remains on its film wall, and the regular patterns such as annulus, spiral, pit, net and the like appears. As illustrated in FIG. 7(a), micro pits $P_{i-1,j-1}, P_{i,j-1}, P_{i+1,j-1}$, - - - , $P_{i-1,j}, P_{i,j}, P_{i+1,j}$, - - - each having a diameter of about 2 μm are opened on wall pit films of the vessel 201. When any cause such as the dryness of the soil or the like disturbs the supply of water, the negative pressure inside the vessel 201 is increased. Finally, as illustrated in FIG. 7(b), the micro bubbles of the air are passed through the micro pits $P_{ij}$ of the wall pit films of the vessels and tracheids, which are already hollowed and adjacent to each other, and then, the micro bubbles of the air are injected into the vessels 201, and the bubbles are released, thereby generating the cavitation. When the cavitation is occurred and water column is interrupted, a part of the energy corresponding to the tension force applied to water column is emitted as the elastic wave (AE). Thus, the elastic wave reception sensors 11a, 11b, 11c, 11d, - - - detect the elastic wave (AE). As illustrated in FIG. 7(c), with the cavitation, the inside of the vessel 201 is filled with the air and becomes in the embolism state. With the continuation of the embolism illustrated in FIG. 7(c), water flow resistance is increased, and water supply performance is further decreased. Thus, as illustrated in FIG. 7(a), the vessel 201 in the embolism state is again filled with water and recovered and refilled. The refilling is carried out even in the daytime in which the transpiration quantity is great. Consequently, water supply performance of the xylem is kept. However, when water stress is further increased so as to increase the number of the vessels 201, in which the cavitation is occurred, the number of vessels 201 lying in the permanent embolism state, ascribable to the prohibited refilling to the vessels 201, will increase in the xylem. With the increase of the number of vessels 201 lying in the permanent embolism state, because water supply performance is greatly dropped, the plant begins to be wilted.

As the elastic wave reception sensors 11a, 11b, 11c, 11d, - - - , an acoustic emission (AE) sensor is preferable. For the AE sensor serving as the detection device, typically, piezoelectric ceramics and piezoelectric polymers, which are made of piezoelectric materials such as lead zirconium titanate (PZT), lead niobate ($PbNb_2O_6$), lithium niobate (LN: $LiNbO_3$) and the like can be used. However, as the AE sensor, the lead niobate, the lithium niobate and the like are limited to the special use application such as a high temperature environment and the like because their sensibilities are very low as compared with the PZT. When the cavitation is occurred in either one of the vessels 201, among the plurality of vessels implementing the xylem in the vascular tissue, water column is interrupted as illustrated in FIGS. 7(b) and 7(c), and an AE wave is emitted. Then, the AE wave is transmitted to the PZTs provided in the inside of the elastic wave reception sensors $11a, 11b, 11c, 11d$, - - -, and the AE wave is converted into an electric signal by the piezoelectric effect of the PZT. As the elastic wave reception sensors $11a, 11b, 11c, 11d$, - - -, acceleration sensors that uses piezoelectric ceramics and piezoelectric polymers, microphones based on electret condensers, pressure sensors, strain gauges and the like may be used instead of the sensor (AE sensor) configured to detect AEs, using piezoelectric ceramics and piezoelectric polymers. In the AE sensor, a longitudinal effect of the piezoelectric effect, in which the direction of an electric field and the direction of a stress are in parallel, is mainly used. Because the acceleration sensor has a weight element, the acceleration sensor operated only in a frequency region of an acceleration region less than or equal to the resonant frequency of the weight element. However, since the AE sensor does not have the weight element used in the acceleration sensor, the resonant frequency becomes high. The AE sensor is roughly classified into a resonant type (narrow band type) that has a high sensibility at a particular frequency, and a wide band type that has a constant sensibility in a wide frequency range. The resonant type AE sensor establishes the high sensibility by using a mechanical resonance in the detection device. For commercial type, the sensors that typically have the resonant frequency between 60 kHz and 1 MHz are available. However, when the AE sensor of lower resonant frequency characteristics is required, the structure of the piezoelectric type acceleration sensor can be used. The wide band type AE sensor is structured to suppress the resonance by sticking a damper material on the detection device (PZT).

As illustrated in FIGS. 7(b) and 7(c), the frequency of the emitted AE wave, ascribable to the occurrence of the cavitation, is between 1 kHz and 1 MHz, and the finer frequency range depends on the sensors. For example, although the wide band type AE sensor that uses piezoelectric ceramics can measure all frequencies, an ultrasonic region between 20 kHz and 1 MHz is desirable. The acceleration sensor using the weight element can detect the AE wave between 1 kHz and 30 kHz, and the strain gauge can detect the AE wave between 1 kHz and 10 kHz.

Figure 2:
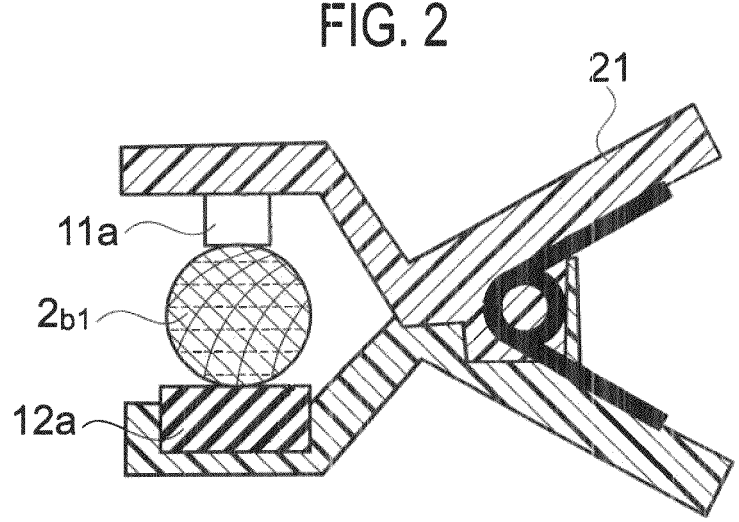
FIG. 2 is a schematic view exemplificatively describing an attaching method of an elastic wave receiving sensor (AE sensor) to subject axis to be measure, in the evaluation system of the botanical-integrity in vascular plant and the irrigating system, according to the first embodiment.
Figure 3:
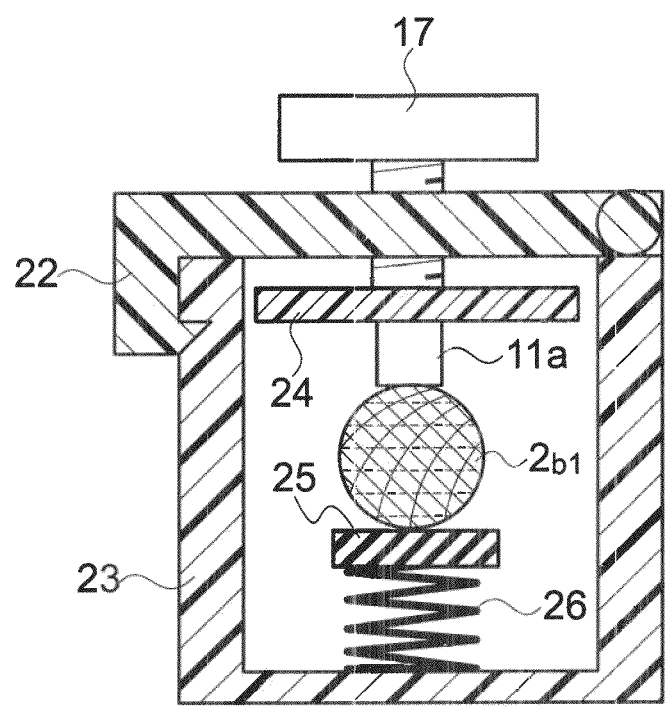
FIG. 3 is a schematic view exemplificatively describing another attaching method of the elastic wave receiving sensor (AE sensor) to the axis, in the evaluation system of the botanical-integrity in vascular plant and the irrigating system, according to the first embodiment.

The scheme of placing the elastic wave reception sensors $11a, 11b, 11c$ and $11d$ to the axis may be carried out by using the architecture of placing the elastic wave reception sensor $11a$ to the side axis $2_{b1}$, for example, as exemplified in FIGS. 2 and 3. In FIG. 2, the elastic wave reception sensor $11a$ is arranged on the side axis $2_{b1}$, and the rubber sheet $12a$ is arranged under the side axis $2_{b1}$. Then, a clip $21$ is used to push the elastic wave reception sensor $11a$ against the side axis $2_{b1}$, and the rubber sheet $12a$ is pushed against the side axis $2_{b1}$. On the other hand, the structure illustrated in FIG. 3 encompasses a main body $23$ having U-shaped cross-section, a spring $26$ provided at the bottom of the main body $23$, a cover $22$ being attached to the top of the main body $23$ in a rotatable configuration, the cover $22$ has a hook engaged with a groove near the other top of the main body $23$, a fixing tool having a screw $17$ provided through the cover $22$, and a rotation buffer $24$ placed at a tip of the screw $17$, the screw $17$ can push down the rotation buffer $24$ by rotating the screw $17$ with respect to the cover $22$. The rotation buffer $24$ is so attached at the tip of the screw $17$ that the rotation buffer $24$ becomes free against the rotation of the screw $17$, because the rotation buffer $24$ has a rectangular flat pattern that can suppress the rotation of rotation buffer $24$, by bringing the rotation buffer $24$ into contact with the inner wall of the main body $23$, thereby serving as a buffer for the rotation of the screw $17$. A rubber sheet $25$ is arranged on the spring $26$, the side axis $2_{b1}$ is arranged on the rubber sheet $25$, the elastic wave reception sensor $11a$ is arranged on the side axis $2_{b1}$, and the hook of the cover $22$ is engaged with the groove of the main body $23$. After that, the screw $17$ is rotated with respect to the cover $22$, and the rotation buffer $24$ is pushed down. Consequently, the elastic wave reception sensor $11a$ can be pushed against the side axis $2_{b1}$, and the rubber sheet $25$ can be pushed against the side axis $2_{b1}$.

Figure 4:
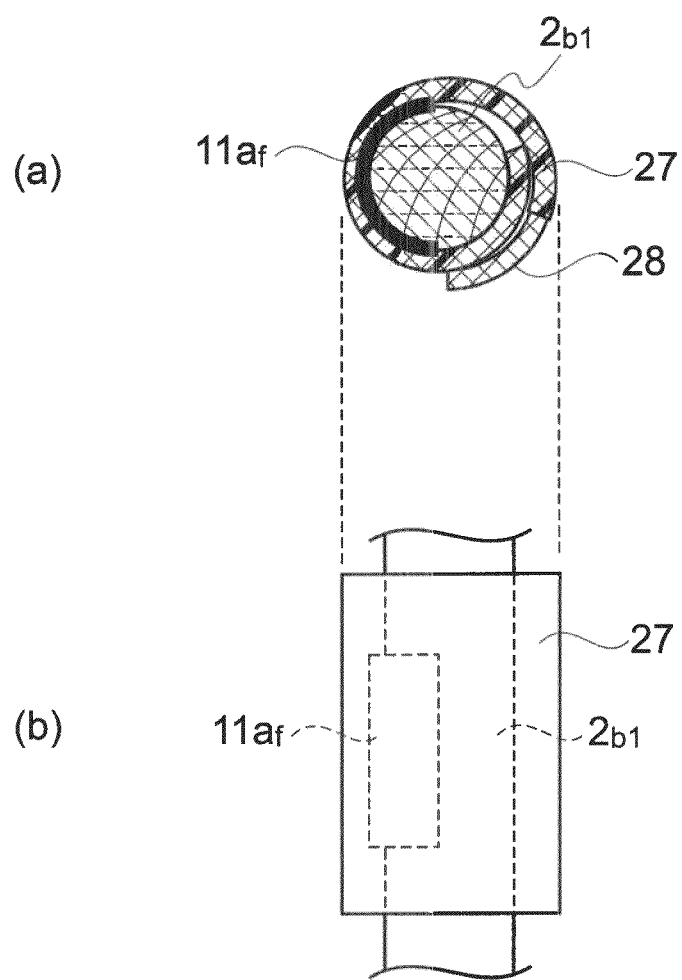
FIG. 4 is a schematic view exemplificatively describing still another attaching method of the elastic wave receiving sensor (AE sensor) to the axis, in the evaluation system of the botanical-integrity in vascular plant and the irrigating system, according to the first embodiment.

As illustrated in FIG. 4 other than those exemplified in FIGS. 2 and 3, the film electret sensor ($11_{af}$, 27, 28) may be wound around the side axis $2_{b1}$, and they may be fixed with an adhesion tape $28$ such as a sheet zip fastener, which is placed at the tip of a flexible base $27$. Moreover, the elastic wave reception sensors $11a, 11b, 11c$ and $11d$ may be adhered to the side axes $2_{b1}, 2_{b2}, 2_{b3}$ and $2_{b4}$, respectively. In order to keep the reception sensibilities of the elastic wave reception sensors $11a, 11b, 11c$ and $11d$ constant, during the measurement, the elastic wave reception sensors $11a, 11b, 11c$ and $11d$ are required to be pushed against (or adhered to) the side axes $2_{b1}, 2_{b2}, 2_{b3}$ and $2_{b4}$, respectively, at a constant pressure. When the elastic wave reception sensors $11a, 11b, 11c$ and $11d$ are pushed against the side axes $2_{b1}, 2_{b2}, 2_{b3}$ and $2_{b4}$, respectively, the pressure is in a range between 10 kPa and 5 MPa and desired to be in a range between 100 kPa and 500 kPa. Also, although the illustration is omitted, when the grease is coated as contact medium between the elastic wave reception sensors $11a, 11b, 11c$ and $11d$ and the side axes $2_{b1}, 2_{b2}, 2_{b3}$ and $2_{b4}$, the measurement sensibilities of the elastic wave $2$ reception sensors $11a, 11b, 11c$ and $11d$ can be improved.

Figure 5:
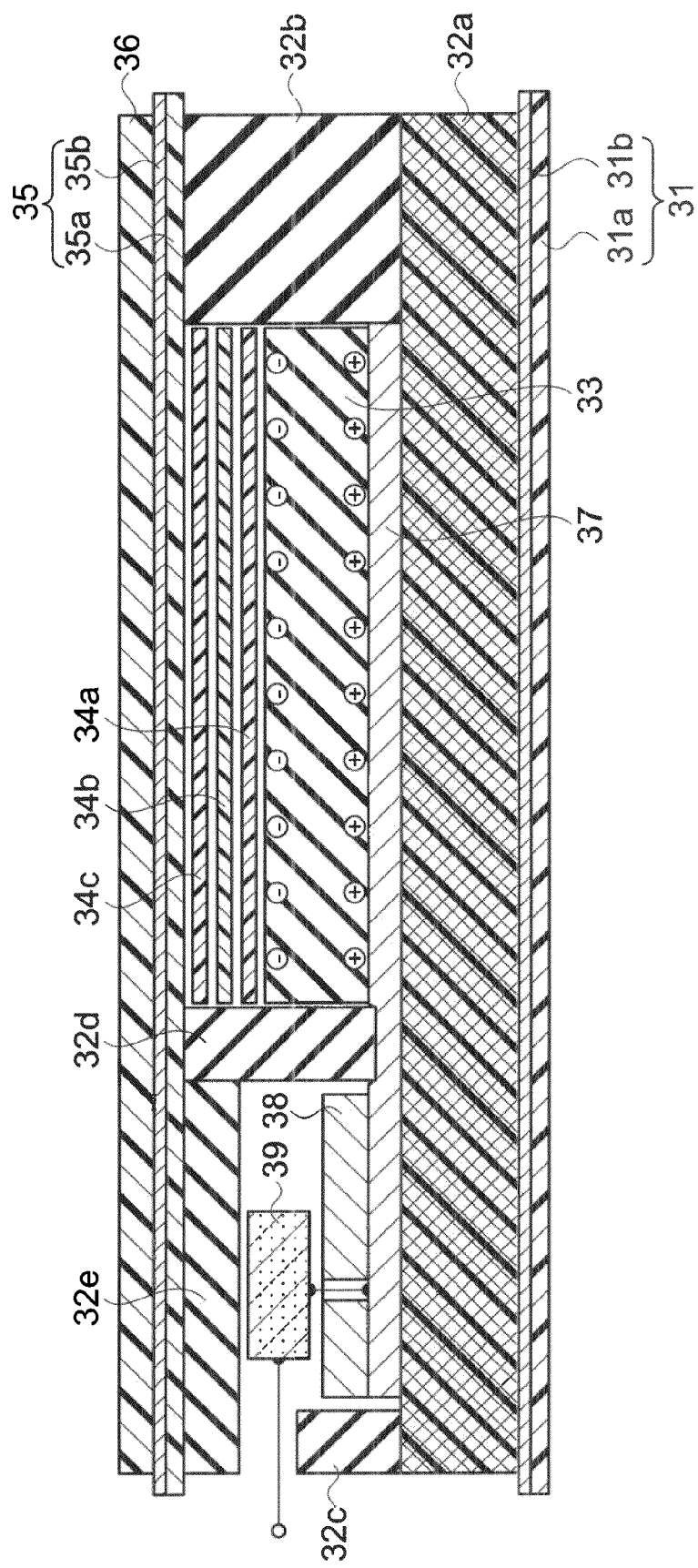
FIG. 5 is a schematic cross-sectional view describing a rough configuration of a film electret sensor, which is preferable for the attaching method in FIG. 4, in the evaluation system of the botanical-integrity in vascular plant and the irrigating system, according to the first embodiment of the present invention.

In the film electret sensor ($11_{af}$, 27, 28), the sensor unit $11_{af}$ is stuck on the flexible base $27$ made of polymer film, and the adhesion tape $28$, which can be adhered to the overlapped portion of the flexible base $27$ when the film electret sensor ($11_{af}$, 27, 28) is fixed to the side axis $2_{b1}$, is connected at the tip of the flexible base $27$. To adhere the adhesion tape $28$ on the overlapped portion of the flexible base $27$, a hooked surface having the many hooks is provided on the surface of the flexible base $27$, and a loop surface in which many circular ring-shaped fibers, referred to as loops, are weaved is provided on the surface of the adhesion tape $28$. Then, the hooked surface and the loop surface are coupled and the hooks are penetrated into the loop layer, and the adhesion tape $28$ and the flexible base $27$ may be fixed to each other. As illustrated in FIG. 5, the sensor unit $11_{af}$ of the film electret sensor includes: a vibration electrode film $35b$; an electret film $33$ opposite to the vibration electrode film $35b$ providing an element space between the vibration electrode film $35b$ and the electret film $33$; a back electrode film $37$ in contact with the bottom surface of the electret film $33$; gap insulation films $34a$, $34b$ and $34c$ which are inserted and laminated in the inside of the element space so as to vertically separate the inside of the element space, providing a plurality of micro gaps between gap insulation films $34a$, $34b$ and $34c$, each interval of micro gaps having a length between 10 nm and 40 μm; and an amplifier (semiconductor chip) $39$ electrically connected between the vibration electrode film $35b$ and the back electrode film $37$. A vibration film $35$ has a flat vibration surface in a state when load is not applied to the vibration film $35$.

In the sensor unit $11_{af}$ of the film electret sensor, an effective surface roughness of each of the surfaces that define the plurality of micro gaps, respectively, is 1/10 or less of a gap width $W_g$ of the element space. Here, the gap width $W_g$ of the element space is defined in a geometrical configuration, which corresponds to a case in which a vibration electrode insulation film 35a and the plurality of gap insulation films 34a, 34b, 34c, - - - are all omitted, in FIG. 5, in the case of the conventional electret microphone, and the gap width $W_g$ corresponds to a distance between the electret film 33 and the vibration electrode film 35b. Thus, in the sensor unit $11_{af}$ of the film electret sensor, the gap width $W_g$ of the element space is defined by the laminated structure implemented by a gap insulation film 34a of a first layer, a gap insulation film 34b of a second layer and a gap insulation film 34c of a third layer are formed just above the vibration surface of the vibration film 35. The polymer film is a film defined by a first main surface that is flat and opposite to the vibration electrode film 35b, establishing the element space between the vibration electrode film 35b and the polymer film, and a second main surface parallel and opposite to the first main surface. However, the polarization directions in the polymer film are made uniform.

The thicknesses of the vibration film 35, the gap insulation film 34a of the first layer, the gap insulation film 34b of the second layer and the gap insulation film 34c of the third layer may be selected correspondingly to a diameter of the axis (for example, the side axis $2_{b1}$) around which the film electret sensor is wound. Then, the thicknesses may be set to 0.1 to 60 μm and preferably set to about 0.1 to 40 μm. When the diameter of the axis is slim, the thicknesses may be set to about 0.1 to 12 μm. Also, the thickness of the polymer film may be selected correspondingly to the diameter of the axis around which the film electret sensor is wound. Then, in the case of the electret manufactured by corona discharge, the thickness may be set to about 1 to 50 μm and preferably set to about 1 to 25 μm and further preferably set to about 1 to 12 μm. Also, in the case of the electret of a ferroelectric substance, the thickness is preferably set to about 1 μm to 60 μm.

Figure 6:
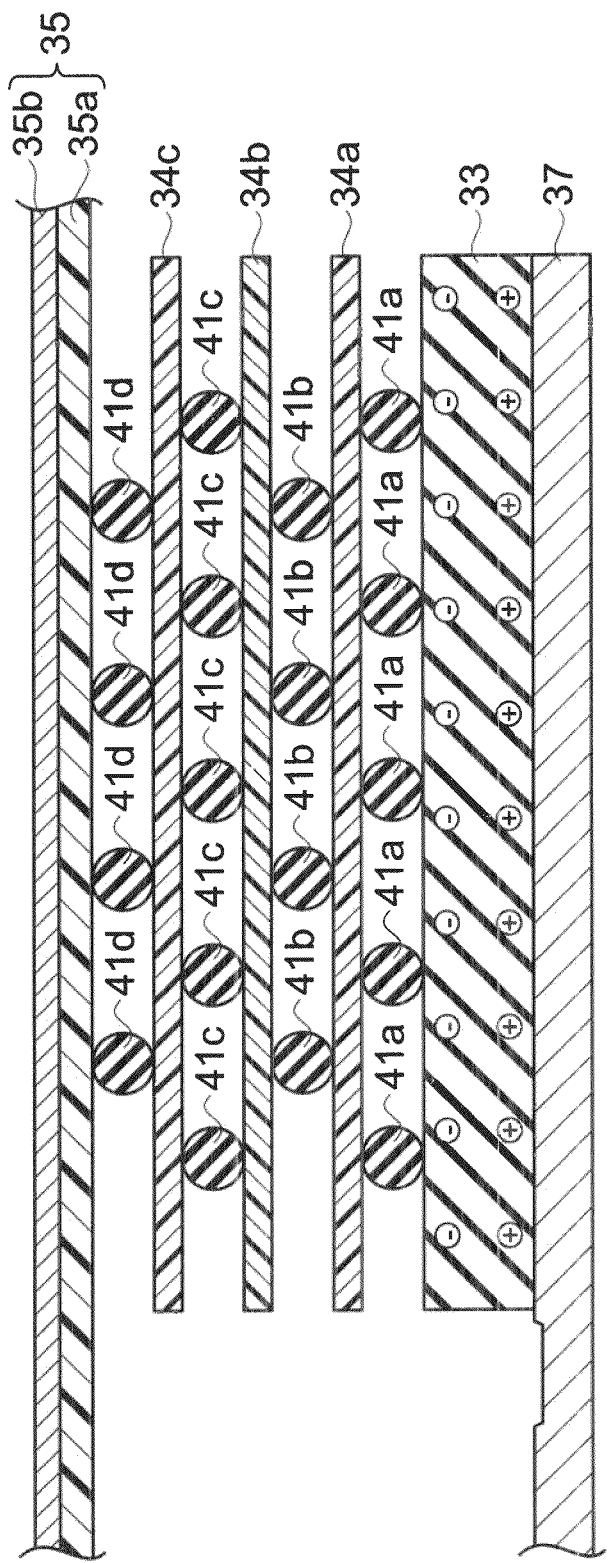
FIG. 6 is a schematic cross-sectional view describing a detailed structure of a micro gap in the film electret sensor illustrated in FIG. 5.

As illustrated in FIG. 6, a first spacer 41a formed of particles of insulators, each particle having a diameter between 10 nm and 40 μm, is inserted between the gap insulation film 34a of the first layer and the polymer film, a second spacer 41b formed of particles of insulator, each particle having the diameter between 10 nm and 40 μm, is inserted between the gap insulation film 34a of the first layer and the gap insulation film 34b of the second layer, a third gap insulation film 34c formed of particles of insulator, each particle having the diameter between 10 nm and 40 μm, is inserted between the gap insulation film 34b of the second layer and the gap insulation film 34c of the third layer, and a fourth spacer 41d formed of particles of insulator, each particle having the diameter between 10 nm and 40 μm, is inserted between the vibration electrode film 35b and the gap insulation film 34c of the third layer. Consequently, the interval of the gap defined between the vibration electrode film 35b and the polymer film is controlled. In this way, the plurality of gap insulation films 34a, 34b, 34c, - - - are laminated and inserted through the spacers 41a, 41b, 41c, 41d, - - - which are formed of particles of insulator, each particle having the diameter between 10 nm and 40 μm, between the vibration electrode insulation film 35a and the polymer film. Consequently, the "micro gaps" are defined, respectively, between the vibration electrode insulation film 35a and the gap insulation film 34c of the third layer, between the gap insulation film 34c of the third layer and the gap insulation film 34b of the second layer, between the gap insulation film 34b of the second layer and the gap insulation film 34a of the first layer, and between the gap insulation film 34a of the first layer and the polymer film, the micro gaps are microscopic air gaps configured to control the respective intervals. The back electrode film 37 and the polymer film may be metallurgically joined, or may be adhered with adhesive agent and the like, or may be merely brought into contact with each other by a mechanical pressure. When the particle diameter of each of the particles serving as the spacers 41a, 41b, 41c, 41d, - - - is set to 60 μm or less, an effective surface roughness $Ra_{eff}$ of the surface that defines each of the micro gaps can be set to 1/10 or less of the gap width in the element space, which is defined to establish the micro gap between the bottom surface of the vibration electrode film 35b and the top surface of the polymer film (the effective surface roughness $Ra_{eff}$ includes the bending under loading condition). However, in order to create the sensor unit $11_{af}$ of the film electret sensor that is flexible and high in shape free degree, the configuration that the particle diameter of each of the particles serving as the spacers 41a, 41b, 41c, 41d, - - - is set between 10 nm and 10 μm is preferable, because the entire thickness can be made more thinner. Moreover, as a matter of course, in the range between 10 nm and 5 μm, the particle diameter closer to 10 nm is desirable.

As illustrated in FIG. 5, the vibration film 35 includes the vibration electrode film 35b formed of conductor and the vibration electrode insulation film 35a on the bottom surface of the vibration electrode film 35b. The thicknesses of the vibration electrode film 35b and the back electrode film 37 may be selected correspondingly to the diameter of the axis around which the film electret sensor is wound. Then, the thicknesses of the vibration electrode film 35b and the back electrode film 37 may be set between about 10 nm and 60 μm, preferably between about 10 nm and 20 μm, and further preferable between about 10 nm and 1 μm.

A vibration film protection film 36 formed of insulation layer is provided on the top surface of the vibration film 35. Because the vibration film protection film 36 services as a matching layer for increasing the adhesion to the vascular plant and the matching property of an acoustic impedance, a soft resin layer is desirable for the vibration film protection film 36. The thickness of the vibration film protection film 36 may be changed and employed in a range between about 10 and 100 μm, depending on the property of the vibration film protection film 36. In the configuration illustrated in FIG. 5, for example, a silicon resin film having a thickness between 50 μm and 100 μm can be used for the vibration film protection film 36.

As illustrated in FIG. 6, since the plurality of gap insulation films 34a, 34b, 34c, - - - are stacked to increase the number of the micro gap layers, not only the damping characteristics but also the reception sensibility is improved. Because the amplitude of the vibration electrode film 35b becomes equal to the sum of the deformations in all of the micro gap layers, unless the acoustic wave (ultrasonic wave) propagated through the gap portion is perfectly attenuated, the reception sensibility improves as the number of the micro gap layers becomes larger. Since the plurality of gap insulation films 34a, 34b, 34c, - - - are stacked, the deformation quantity is increased so as to cover the attenuation of the acoustic wave, the layer of a high elastic modulus such as fluorine resin and the like can be used for each of the plurality of gap insulation films 34a, 34b, 34c, - - - . As the fluorine resin, tetrafluoroethylene-perfluoroalkylvinylether copolymer is typical. However, in addition to the fluorine resin, PET resin (3 GPa), PPS resin (4 GPa), polyimide resin (3 to 7 GPa) and the like can be used. However, attention should be paid to a fact that in order to increase the number of the laminations of the plurality of gap insulation films 34a, 34b, 34c, - - -, when the width of the entire gap is made wider, the increased width leads to the drop in the electric field strength in the gap.

The polymer film is the layer, which is electrified and develops the electric field to the exterior. For example, the polymer film is manufactured such that the polymer film is electrified by the corona discharge, or the ferroelectric material is heated to remove the surface charges. Although the illustration is omitted, an electret insulation film may be formed on the top surface of the polymer film, and the first spacer 41a may be arranged on the electret insulation film. As illustrated in FIG. 5, the plurality of gap insulation films 34a, 34b, 34c, - - - and the polymer film are encapsulated in the inside of box-shaped insulation containers (32b, 32d), and the vibration film 35 serves as the cover unit of those insulation containers (32b, 32d), and the back electrode film 37 serves as the bottom plate of those insulation containers (32b, 32d). Moreover, a structure in which the plurality of gap insulation films 34a, 34b, 34c, - - - and the polymer film are housed in the inside of the insulation containers (32b, 32d) is placed in the inside of the insulation containers (32a, 32b and 32c) in which a spacer film 32a made of insulation materials serves as a bottom plate. The vibration film 35 serves as the cover unit of those insulation containers (32a, 32b and 32c). A shield conductor protection film 31a is formed on the bottom portion of a shield conductor film 31b. The shield conductor protection film 31a and the shield conductor film 31b implement a shield plate 31. The thicknesses of the spacer film 32a and the shield conductor protection film 31a can be set to a value between about 5 and 80 μm and can be preferably set to a value between about 50 and 60 μm.

For example, when the polymer film and the gap insulation films 34a, 34b and 34c and the vibration electrode insulation film 35a are PFA films, the respective thicknesses can be set to about 10 μm. When the vibration electrode film 35b and the back electrode film 37 are Al films, their thicknesses can be set to about 10 μm. When the spacer film 32a and the shield conductor protection film 31a are silicon resin films, the respective thicknesses of the spacer film 32a and the shield conductor protection film 31a can be set to about 60 μm. In FIG. 5, the thicknesses of the side wall films 32b, 32d servicing as the side plates of the box-shaped insulation containers (32a, 32b, 32d and 32e) may be designed by considering the thickness of the polymer film, the number of the gap insulation films 34a, 34b, 34c, - - - and the respective thicknesses. However, the thickness of approximately 60 μm is preferable, in order to make the insulation containers (32a, 32b, 32d and 32e) flexible.

At the time of no load condition, the first main surface of the polymer film is parallel and opposite to the vibration surface of the vibration film 35. Here, the amplifying means includes: a semiconductor chip 39 in which amplifiers (FETs) connected to the back electrode film 37 are integrated; and an external circuit (whose illustration is omitted) connected 2 to the semiconductor chip 39. FIG. 5 illustrates the sensor unit $11_{af}$ of the film electret sensor. In the sensor unit $11_{af}$ of the film electret sensor, the external circuit includes: a direct current power source E in which one terminal is grounded; a buffer resistor R connected between the direct current power source E and the semiconductor chip 39; and a coupling capacitor C in which one electrode is connected to a connection node between the buffer resistor R and the semiconductor chip 39 and the other electrode serves as an output terminal. An outer circuit (whose illustration is omitted) is connected to the output terminal of the coupling capacitor C serving as an output terminal of the semiconductor chip 39. Then, the outer circuit carries out the signaling processes necessary for a communication apparatus and a recording apparatus which are connected to a microphone. In the semiconductor chip 39 in the sensor unit $11_{af}$ in the film electret sensor, a potential between the back electrode film 37 and the vibration film 35 is amplified by the semiconductor chip 39, and the charges introduced to the polymer film in association with the deformation of the vibration surface of the vibration film 35 are measured.

The "gap width $W_g$ of the macroscopic element space" is defined between the vibration electrode film 35b and the polymer film. The $W_g$ is in a range between 0.1 and 1000 μm. Each of the micro gaps, which are microscopic air gaps, is defined between the vibration electrode insulation film 35a and the gap insulation film 34c of the third layer (between the vibration electrode film 35b and the gap insulation film 34c of the third layer, when the vibration electrode insulation film 35a is omitted), between the gap insulation film 34c of the third layer and the gap insulation film 34b of the second layer, between the gap insulation film 34b of the second layer and the gap insulation film 34a of the first layer, and between the gap insulation film 34a of the first layer and the electret insulation film (between the gap insulation film 34a of the first layer and the polymer film, when the electret insulation film is omitted) is the gap in which the gap width is between 10 nm and 40 μm and a dielectric breakdown strength of the air in the gap is between 5 and 200 MV/cm, which are improved as compared with those of the macroscopic gap. In the case of the gap width $W_g$ of the macroscopic element space, the dielectric breakdown strength of the air is about 3 MV/m. However, the dielectric breakdown strength can be further improved by injecting insulation gas, such as fluorine-based gas and the like, other than the air, into the gap width $W_g$ of the macroscopic element space, or making the macroscopic element space vacuum.

The vibration electrode film 35b is pulled and bent by the electrostatic force of the polymer film, and the bending of the vibration electrode film 35b decreases the dielectric breakdown strength of the micro gap. In order to obtain the high dielectric breakdown strength as mentioned above, the effective surface roughness $Ra_{eff}$ of the surface that defines the micro gap must be less than or equal to ⅒ of the gap width in the element space.

For the vibration film 35, any material may be used, when the bending of the vibration electrode insulation film 35a or vibration electrode film 35b is less than or equal to ⅒ of the gap width $W_g$ of the element space, the vibration electrode film 35b is superior in conductivity, and the vibration electrode insulation film 35a is excellent in electric insulation. Although the vibration film 35 is required to be high in rigidity, the vibration film 35 is preferred to be light in weight in order to be able to follow a high frequency. To operate at a high frequency, a material having a high value of a specific rigidity (=(elastic modulus/density)) is preferred to be used in one of the vibration electrode film 35b of the vibration film 35, the vibration electrode insulation film 35a on the bottom surface of the vibration electrode film 35b, and the matching layer (whose illustration is omitted in FIG. 5) on the top surface of the vibration electrode film 35b. For this reason, in view of the materials implementing the vibration film 35, aluminum (Al) and its alloy, or magnesium (Mg) and its alloy can be used as the vibration electrode film 35b, and FEP layer can be used as the vibration electrode insulation film 35a, which is stuck on the vibration electrode film 35b. Or, PET, PEN, epoxy resin, phenol resin and the like can be used as material for the vibration electrode insulation film 35a, and aluminum film can be used as the vibration electrode film 35b, the aluminum film is deposited on the vibration electrode insulation film 35a. Or, alumina, silicon nitride, silicon carbide ceramics and the like can be used as material for the vibration electrode insulation film 35a, and on the vibration electrode insulation film 35a, an aluminum film may be deposited or a silver film may be baked so as to implement the vibration electrode film 35b. In addition, FEP resin used in the insulation layer of a conventional electret microphone, the silicon substrate having a silica layer and the like can be used as material for the vibration electrode 2 insulation film 35a, however, because the thickness of the vibration electrode insulation film 35a is required to be increased such that the bending is less than or equal to 1/10 of the gap width in the element space, the configuration of the vibration electrode insulation film 35a differs from the designing idea of the conventional electret microphone. Also, the other resins that are superior in insulation (silicon-based resin, fluorine-based resin, polyethylene-based resin, polyester, polypropylene, polycarbonate, polystyrene, urethane, ABS, flexible polyvinyl chloride and the like) or the like can be used as material for the vibration electrode insulation film 35a. Then, the vibration electrode film 35b is attached on the vibration electrode insulation film 35a, by adhesion, deposition or baking, and the vibration film 35 may be assembled. In the assembling scheme of the vibration film 35, the thickness of the vibration electrode film 35b or vibration electrode insulation film 35a shall be increased to reserve the rigidity necessary for the vibration film 35.

For the spacers 41a, 41b, 41c, 41d, it is necessary to use the materials that are superior in electric insulation. Specifically, the ceramics such as silica, alumina, silicon nitride, silicon carbide and the like, and the resin such as silicon-based resin, fluorine-based resin, polyethylene-based resin (including PET and the like), polyester, polypropylene, polycarbonate, polystyrene, urethane, ABS, flexible vinyl chloride and the like can be used. Also, for the spacers 41a, 41b, 41c, 41d, - - -, the materials whose elastic modulus is 2 GPa or less is used. However, in a configuration such that the vibration electrode insulation film 35a is disposed on the side of the vibration film 35, and the elastic modulus of the vibration electrode insulation film 35a is 2 GPa or less, there is no limit on the elastic moduli of the spacers 41a, 41b, 41c, 41d, - - -. As the material which has the excellent electric insulation and has the elastic modulus of 2 GPa or less, specifically, the reins such as silicon-based resin, fluorine-based resin, polyethylene-based resin, polyester, polypropylene, polycarbonate, polystyrene, urethane, ABS, flexible vinyl chloride and the like can be used.

With regard to the spacers 41a, 41b, 41c, 41d, - - -, it is allowable to form micro protrusions each having a height between 10 nm and 40 μm on the top surface of the gap insulation film 34c of the third layer, as well as the particles each having the particle diameter between 10 nm and 40 μm, as illustrated in FIG. 6. The micro protrusions can be formed on the top surface of the gap insulation film 34c of the third layer, by using a method such as pulse laser irradiation, lithography, etching, press and the like. Or, the micro protrusions each having the height between 10 nm and 40 μm may be formed on the bottom surface of the vibration electrode insulation film 35a or on the bottom surface of the vibration electrode film 35b when the vibration electrode insulation film 35a is omitted. Similarly, instead of the spacer 41d formed of particles of insulator, each having the particle diameter between 10 nm and 40 μm, the micro protrusions, each having the height between 10 nm and 40 μm, may be formed on the bottom surface of the gap insulation film 34c of the third layer. Moreover, instead of the spacers 41b, 41c formed of particles of insulator, each having the particle diameter between 10 nm and 40 μm, the micro protrusions, each having the height between 10 nm and 40 μm, may be formed on at least one of the bottom surface and the top surface of the gap insulation film 34b of the second layer, and instead of the spacers 41a, 41b formed of particles of insulator, each having the particle diameter between 10 nm and 40 μm, the micro protrusions, each having the height between 10 nm and 40 μm, may be formed on at least one of the bottom surface and the top surface of the gap insulation film 34a of the first layer. Moreover, the micro protrusions, each having the height between 10 nm and 40 μm, may be formed on the top surface of the electret insulation film when the electret insulation film is disposed on the top surface of the polymer film, or the micro protrusions may be formed on the top surface of the polymer film when the electret insulation film is omitted. In order to create the sensor unit $11_{af}$ of the film electret sensor which is flexible and high in shape free degree, the height of the micro protrusion set between 10 nm and 10 μm is preferable, because the entire thickness can be made thinner, and more preferably, the height closer to 10 nm in the range between 10 nm and 5 μm is preferable.

The particles and the protrusions serve as supporters, respectively, between the vibration electrode insulation film 35a and the gap insulation film 34c of the third layer (between the vibration electrode film 35b and the gap insulation film 34c of the third layer, when the vibration electrode insulation film 35a is omitted), between the gap insulation film 34c of the third layer and the gap insulation film 34b of the second layer, between the gap insulation film 34b of the second layer and the gap insulation film 34a of the first layer, and between the gap insulation film 34a of the first layer and the electret insulation film (between the gap insulation film 34a of the first layer and the polymer film, when the electret insulation film is omitted). Consequently, the micro gaps are formed. As far as the micro gaps can be formed, the shapes of the spacers 41a, 41b, 41c, 41d, - - - may be arbitrary. However, the curvature of the contact point of the protrusion is desired to be larger. Also, when the layer having the surface roughness in which the maximum height ($R_{max}$) is between 10 nm and 40 μm is laminated, the micro gap can be formed without using the spacers 41a, 41b, 41c, 41d, - - -.

The vibration electrode insulation film 35a, the gap insulation film 34a of the first layer, the gap insulation film 34b of the second layer, the gap 3 insulation film 34c of the third layer and the electret insulation film whose illustration is omitted are the layers of the insulators in which as mentioned above, the protrusions between 10 nm and 40 μm are formed or the particles each having the particle diameter between 10 nm and 40 μm are deposited on the surfaces. FIGS. 5 and 6 exemplify the case in which the three insulation layers implemented by the gap insulation film 34a of the first layer, the gap insulation film 34b of the second layer and the gap insulation film 34c of the third layer are stacked. However, as necessary, the more multi insulation films can be added to increase the number of the micro gap layers. Or, only on the surface of the partial insulation layers, the protrusions are formed or the particles are deposited, and the remainders are closely adhered or dried and brought into contact, and the surface roughness can be used to form the micro gap. When the gap width is within 1000 μm, as the lamination number of the insulation films is greater, the acoustic damping characteristics is improved. Also, as the insulation layer becomes made thicker, the gap width becomes made wider so as to protect the drop in the dielectric breakdown strength of the micro gap that is caused by the bending of the vibration electrode film 35b, however, the increase in the gap width leads to the drop in the electric field strength in the gap. For this reason, the optimal number of the laminations is determined on the basis of the thickness of the insulation layer, the structure of the micro gap and the like.

The polymer film must have a surface potential that enables the electric field between 5 and 200 MV/m to be generated in the gap. As the typical example of the polymer film, an insulation layer that is electrified by the corona discharge and a ferroelectric layer that is electrified by heating can be used. As the insulation layer that is electrified by the corona discharge, it is possible to exemplify the polymer film that is formed by electrifying the fluorine-based resin or silica surface through the use of the corona discharge. As the ferroelectric layer, a single crystal or polycrystal of the ferroelectric material, or the crystalline polymer can be used. As the ferroelectric material, perovskite type compound, tungsten bronze structure compound, bismuth-based layered structure compound, wurtzite structure crystal, zinc oxide, berg crystal, Rochelle salt and the like can be used. For example, a polymer film that is formed by heating the ferroelectric material, such as PZT, $LiNbO_3$, PVDF and the like, in which the polarization direction is oriented in one direction, and transiently reducing the polarization through the use of pyroelectric effect, and removing the surface charges, and again cooling to a room temperature can be used.

For example, the thickness of the polymer film can be selected between about 10 and 50 μm in the case of the PTFE film that is electrified by the corona discharge, and the thickness can be selected between about 0.5 and 2 mm in the case that PZT is used as the ferroelectric material. For example, each of the thicknesses of the back electrode film 37 and the vibration film 35 can be selected between about 1 and 60 μm in the case of the Al deposition PET film. However, the specific thicknesses and radiuses of the vibration film 35, the polymer film and the back electrode film 37 may be determined on the basis of the design policy and the requested performance and specification.

The semiconductor chip 39 is placed (mounted) on a circuit substrate 38, in the vicinity of the left end of the back electrode film 37. Through holes (vias) are made in the circuit substrate 38. Then, through the through holes (vias), the semiconductor chip 39 is electrically connected to the back electrode film 37, through solder fused in the vicinity of the left end of the back electrode film 37. Although the illustration is omitted, a ground wiring, being departed from the semiconductor chip 39, is connected to the shield conductor film 31$b$ of the shield plate 31 by soldering.

Penetration holes (whose illustrations are omitted) that penetrate through the back electrode film 37, the plurality of gap insulation films 34$a$, 34$b$, 34$c$, - - - and the polymer film are made respectively in the back electrode film 37, the plurality of gap insulation films 34$a$, 34$b$, 34$c$, - - - and the polymer film. The penetration holes are sealed by using the solder and the like so that (as necessary), the gas (insulation gas) whose insulation property is high can be encapsulated into the gap space between the polymer film and the vibration film 35. As the insulation gas, nitrogen, sulfur hexafluoride and the like can be used. In addition to the insulation gas, if the insulation fluid such as silicon oil and the like is filled in the gap space, which is formed by the plurality of gap insulation films 34$a$, 34$b$, 34$c$, - - - , between the polymer film and the vibration film 35, the dielectric breakdown strength can be increased so as to make difficult the occurrence of the discharging. As a result, it is possible to decrease the quantity of the charges on the surface of the polymer film, which are adsorbed by the discharging, and the sensibility improves. It is possible to improve the sensibility, even if evacuating the gap space between the polymer film and the vibration film 35, instead of filling the insulation gas and the insulation fluid.

The film electret sensor exemplified in FIGS. 5 and 6 can effectively receive the elastic wave (AE) emitted from the medium of the low acoustic impedance, such as the vascular plant, because the acoustic impedances of a pressure reception surface (silicon resin surface) and the gap portion are low. Since the sensor that uses piezoelectric ceramics is high in acoustic impedance, the sensor using piezoelectric ceramics can receive only a part of the acoustic energy generated between the sensor and the vascular plant. When piezoelectric polymers are used for the sensor, the reception efficiency is slightly improved. However, in the film electret sensor exemplified in FIGS. 5 and 6, the contact rigidity of the micro gap unit is low, which leads to the lower acoustic impedance. Thus, the reception efficiency of the elastic wave (AE) emitted from the vascular plant is high. Also, the film electret sensor of the present invention can receive all of the waves of the frequency between 1 kHz and 1 MHz of the elastic wave (AE) at a flat reception sensitivity, and the film electret sensor can easily change the frequency in accordance with the characteristics of the vascular plant.

Actually, although the cross-cross-sectional shape of the axis of the vascular plant is not smooth cylinder as exemplified in FIGS. 2 to 4, and the actual cross-cross-sectional shape of the axis has ups and downs, the flexibility of the film electret sensor can be utilized to improve adhesion degree to the actual axis having non-cylindrical cross-cross-sectional shape.

<Definition of Change Rate in Occurrence Frequency of Elastic Wave>

As illustrated in FIG. 1, in a side axis $2_{b1}$, by cutting (disconnecting) 2 the side axis $2_{b1}$ at a position $C_1$ allocated at closer portion to the root than the position of the elastic wave reception sensor 11$a$, water stress is rapidly varied, in a side axis $2_{b2}$, by cutting (disconnecting) the side axis $2_{b2}$ at a position $C_2$ allocated at closer portion to the root than the position of the elastic wave reception sensor 11$b$, water stress is rapidly varied, in a side axis $2_{b3}$, by cutting (disconnecting) the side axis $2_{b3}$ at a position $C_3$ allocated at closer portion to the root than the position of the elastic wave reception sensor 11$c$, water stress is rapidly varied, and in a side axis $2_{b4}$, by cutting (disconnecting) the side axis $2_{b4}$ at a position $C_4$ allocated at closer portion to the root than the position of the elastic wave reception sensor 11$d$, water stress is rapidly varied. Then, ratio of the AE occurrence frequencies between before and after the variations of water stresses are examined, respectively (FIG. 1 exemplifies the four elastic wave reception sensors 11$a$, 11$b$, 11$c$ and 11$d$. Typically, at least one elastic wave reception sensor (AE sensor) is attached to the axis that includes the main axis, the side axis, the petiole (leaf stalk) and the vein. Then, water stress may be rapidly varied by cutting (disconnecting) the axis at a position allocated at closer portion to the root than the position where at least one elastic wave reception sensor (AE sensor) is disposed.)

Figure 8:
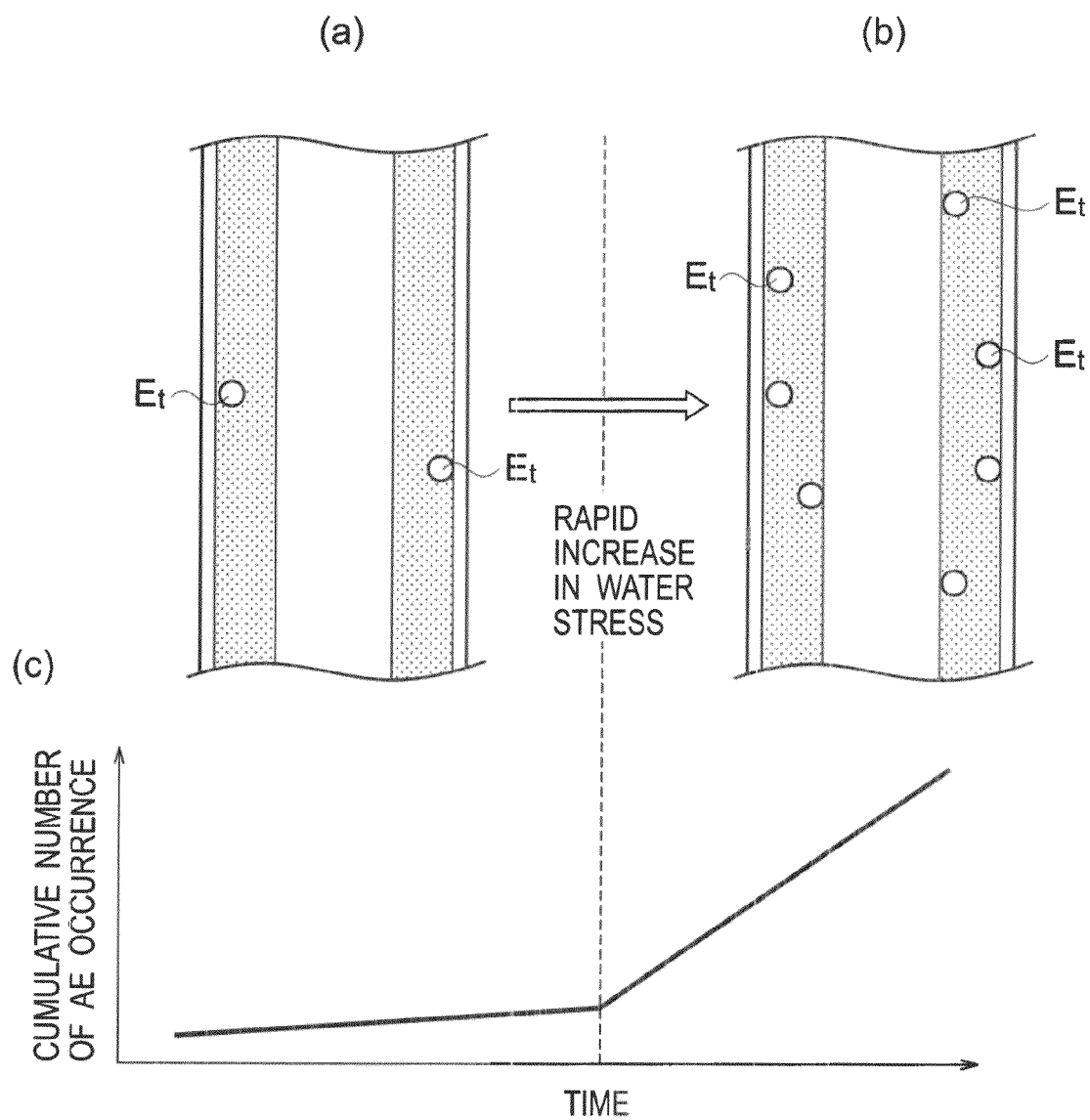
FIG. 8 is a schematic view describing a state in which, although the rapid increase in water stress causes the increase in an cumulative number of AE occurrence, refilling is also increased, thereby recovering the temporary embolism, correspondingly to the increase in water stress, in the vascular plant.
Figure 9:
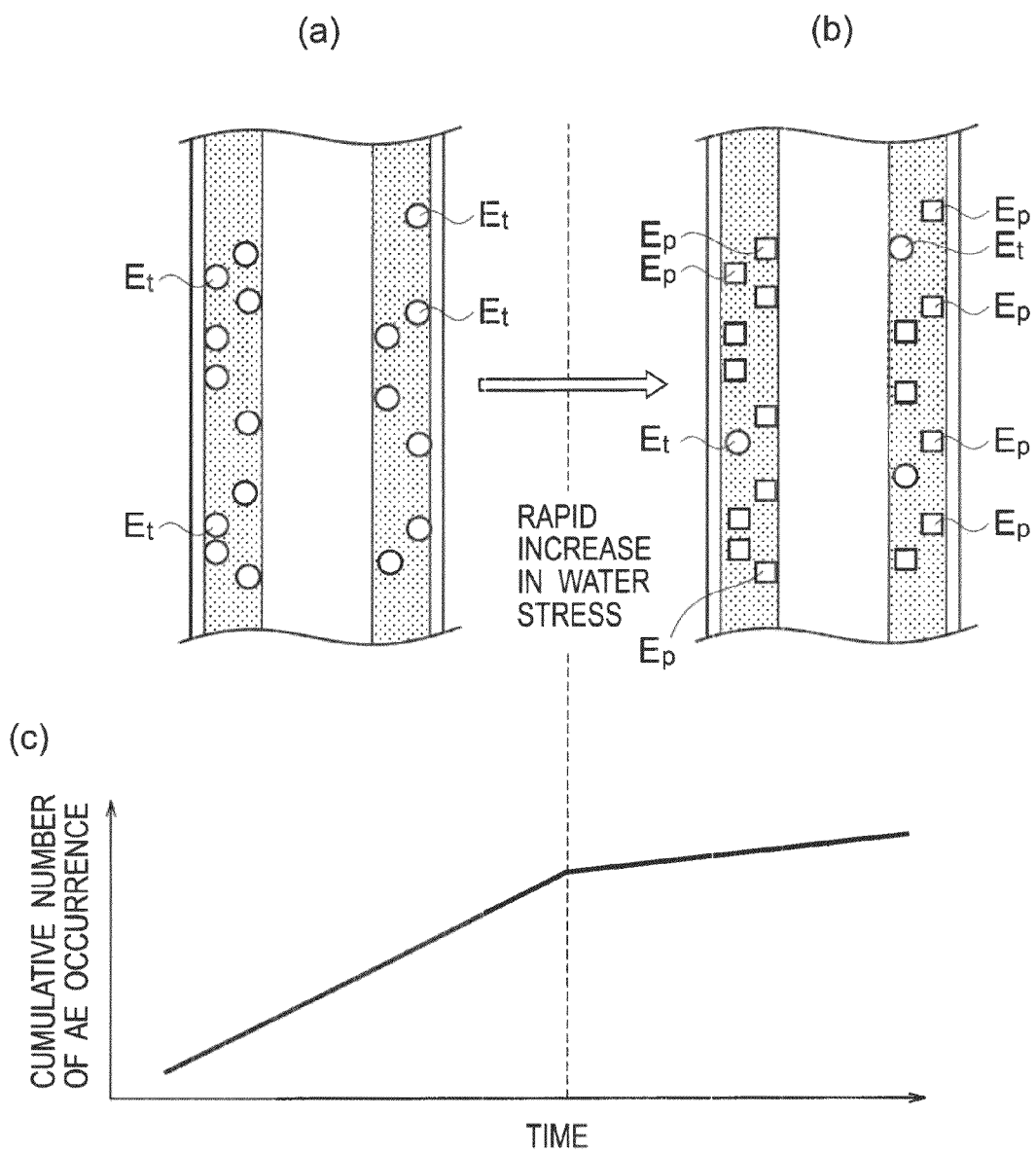
FIG. 9 is a schematic view illustrating a case that an increase rate of the cumulative number of AE accumulation occurrence is decreased in association with the sharp increase in water stress and also describing a situation in which the embolism cannot be recovered.

In the irrigating system according to the first embodiment, as illustrated in FIGS. 8 and 9, the risk level at which the embolism disturbs the growth is evaluated from the cumulative number of AE occurrence. In a state when embolism density is low, as illustrated in FIG. 8, a rapid increase in water stress results in the increase in the cumulative number of AE occurrence. As mentioned above, the location at which the many vessels are congregated is referred to as the xylem, and in the axis such as the stem of the vascular plant and the like, the xylems align in a ring-like shape. The open circles (○) in FIG. 8($a$) schematically illustrates a state in which a temporary embolism $E_t$ is generated in a part of the many vessels implementing the xylem in the vascular tissue. Also, the open circles (○) in FIG. 8($b$) illustrates a state in which the number of the temporary 29 embolisms $E_t$ generated in any of the many vessels implementing the xylem in the vascular tissue is increased by the rapid increase of water stress. In the state illustrated in FIG. 8, since the refilling is also increased in response to the increase in the cavitation, the temporary embolism $E_t$ is also recovered correspondingly to the increase in water stress, in the plant. Hence, the risk at which the temporary embolism $E_t$ disturbs the growth is low.

However, in a case as illustrated in FIG. 9, although water stress is rapidly increased, the increase rate of the cumulative number of AE occurrence decreases, since the embolism density is set to be already high, even if water stress is rapidly increased, the embolism cannot be recovered any more, and water supply performance of the xylem is consequently decreased. The open circles (○) in FIG. 9(a) schematically indicates a state in which the many temporary embolisms $E_t$ are generated in the many vessels implementing the xylem in the vascular tissue. Also, open squares (□) in FIG. 9(b) indicates a state in which in addition to the temporary embolism $E_t$ indicated by the open circles, the rapid increase in water stress induces a stationary (unrecoverable) embolism $E_p$ in the many vessels implementing the xylem in the vascular tissue. That is, the stationary embolism $E_p$ indicated by the open squares in FIG. 9(b) severely disturbs the growth of the vascular plant.

Figure 10:
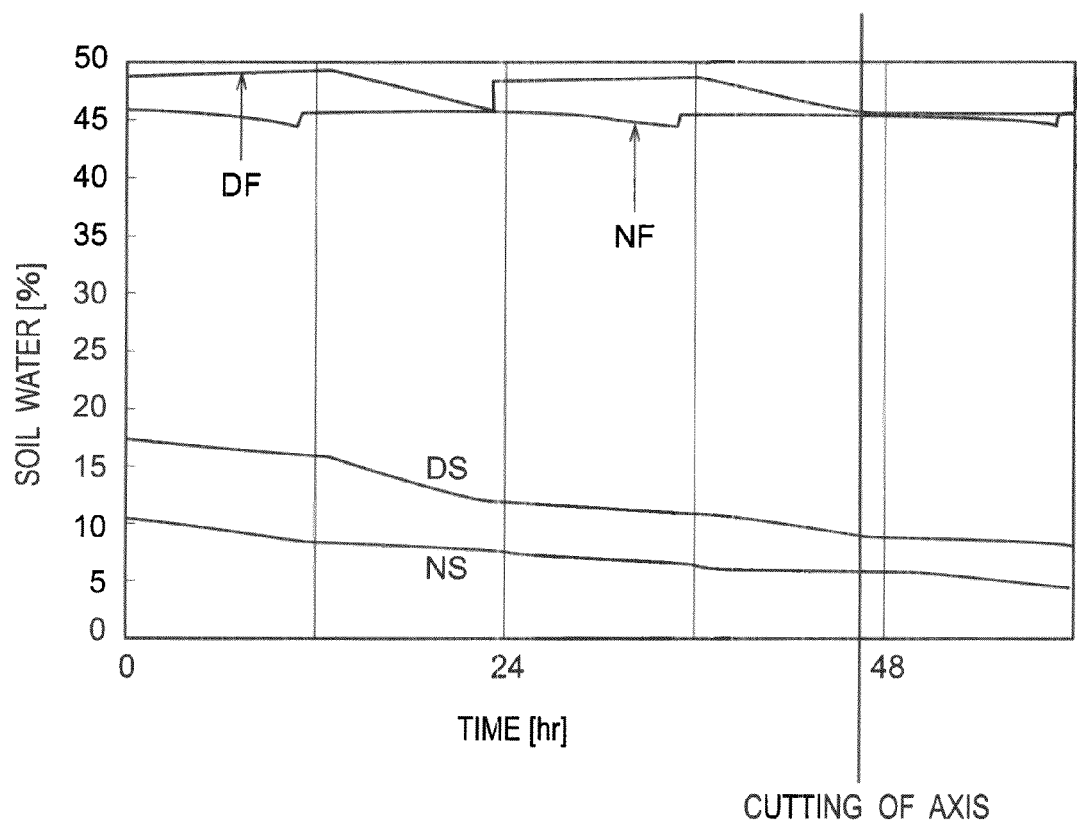
FIG. 10 is a view illustrating the change in the measured soil water with time, for a case that water stress is small (DF, NF) and a case that, until the vascular plant begins to be wilted, water stress is increased (DS, NS).

The specific measurement examples are illustrated in FIGS. 10 to 13. FIGS. 10 to 13 illustrate the measurement results of the elastic wave (AE), which are measured in a topology as illustrated in FIG. 1, that is, the elastic wave reception sensors 11a, 11b, 11c and 11d are attached respectively to the four side axes $2_{b1}$, $2_{b2}$, $2_{b3}$ and $2_{b4}$ of the miniature tomato, which is one example of the vascular plant, and the side axes $2_{b1}$, $2_{b2}$, $2_{b3}$ and $2_{b4}$ are cut (disconnected) at positions allocated at closer portions to the root than the positions of the respective elastic wave reception sensors 11a, 11b, 11c and 11d, and water stresses at positions disposed near to the elastic wave reception sensors 11a, 11b, 11c and 11d are rapidly increased. In the measurement, since the temperature, the solar radiation, the fertilization, the soil and the like are controlled to be the same conditions, water stress greatly receives the influence of the soil water. Then, as illustrated in FIG. 10, a case, in which the soil water is about 40% and substantially constant and water stress is small (DF, NF), and another case, in which the soil is gradually dried and water stress is increased (DS, NS) until the miniature tomato begins to be wilted, are measured. In FIG. 10, DF indicates a case that water stress in the daytime is small (free) as illustrated in FIG. 11(a). Also, NF indicates a case that water stress in the nighttime is small as illustrated in FIG. 11(b). Moreover, DS in FIG. 10 indicates a case that water stress in the daytime is great (severe) as illustrated in FIG. 12(a), and NS indicates a case that water stress in the nighttime is great as illustrated in FIG. 12(b), respectively.

In the case that water stress is small (DF, NF), the AE occurrence frequency is greatly increased after the axis is cut, as illustrated in FIG. 11. In short, FIG. 11 indicates that, since the embolism density is low, even if the increase in water stress after the cut causes the increase in the embolism, a function for recovering the embolism is operated. On the other hand, in the case that water stress is great (DS, NS), as illustrated in FIG. 12, after the cut, the change in the inclination of a curve that indicates the change in AE occurrence frequency is zero, or the inclination of the change in AE occurrence frequency is decreased, and the AE occurrence frequency is not changed or the change in AE occurrence frequency is decreased (attention should be paid to the fact that the scale of the longitudinal axis is different between FIGS. 11 and 12). In short, as illustrated in FIG. 12, in a state in which the embolism density is high, when the cut of the axis results in the increase in the embolism, the increased embolism cannot be recovered any more, and the permanent embolism is increased.

In order to numerically express the recoverable condition of the embolism, with $AE_{low}$ defined as the AE occurrence frequency of the vascular plant when water stress is low, and $AE_{high}$ defined as the AE occurrence frequency of the vascular plant when water stress is high, the change rate of the occurrence frequency of the elastic wave (the rate of change of AE occurrence frequency $R_{AE}$) is defined by:

$$R_{AE}=(AE_{high}-AE_{low})/(AE_{low}+AE_{high}) \quad (2)$$

The rate of change of AE occurrence frequency $R_{AE}$ defined by Eq. (2) implies the change rate of the embolism occurrence (cavitation) frequency of the vascular plant that is caused by water stress variation, however, the rate of change of AE occurrence frequency $R_{AE}$ has a negative correlation with the embolism density of the vascular plant.

Figure 13:
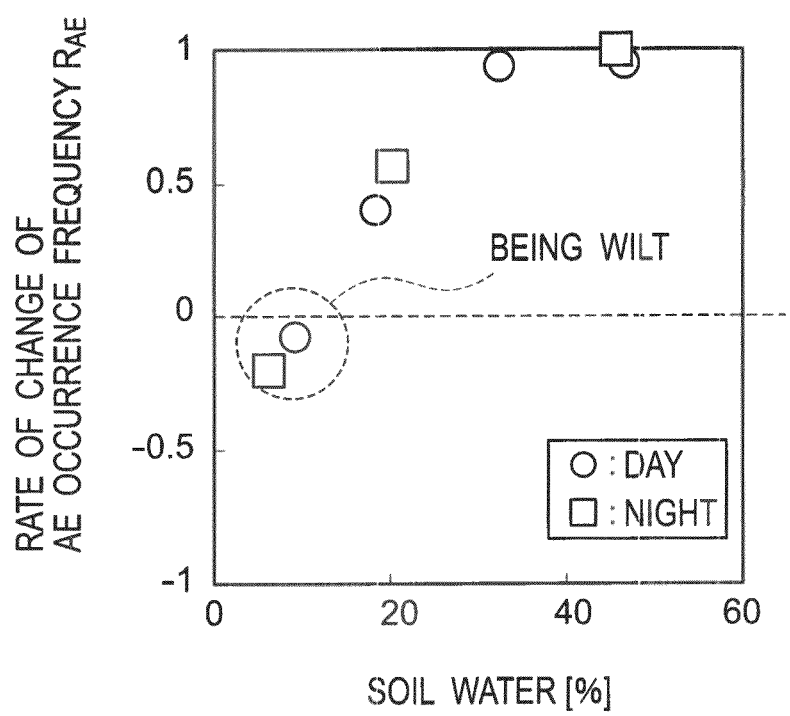
FIG. 13 is a view that illustrates a mutual relationship between the soil water and an AE occurrence frequency change rate RAE of the vascular plant and describes that, when the AE occurrence frequency change rate RAE becomes 0 or less, the unrecoverable embolism is generated, and the vascular plant begins to be wilted.

As illustrated in FIG. 13, the embolism density when the rate of change of AE occurrence frequency $R_{AE}$=0 corresponds to the "critical embolism density" of the vascular plant, and indicates that the embolism arrives at a state in which the cells of the vascular plant cannot be recovered. In the experiments illustrated in FIGS. 10 to 12, the AE occurrence frequency $AE_{low}$ indicating water stress is low corresponds to an AE occurrence frequency $AE_{before}$, which is defined as the rate of change of AE occurrence frequency measured from one hour before the cut of the vascular plant until the time when the vascular plant is cut, and the AE occurrence frequency $AE_{high}$ indicating water stress is high corresponds to an AE occurrence frequency $AE_{after}$, which is defined as the rate of change of AE occurrence frequency measured from the time when the vascular plant is cut to the time after one hour has passed from the cut of the vascular plant. Here, as an index of the embolism density of the vascular plant in a state before the cut, an embolism density ratio $D_{AE}$ can be defined by:

$$D_{AE}=AE_{before}/(AE_{before}+AE_{after}) \quad (3)$$

As illustrated in FIG. 13, in the experiments illustrated in FIGS. 10 to 12, a correlation is observed between the soil water and the rate of change of AE occurrence frequency $R_{AE}$ of the vascular plant. In the experiments illustrated in FIGS. 10 to 12, the correlation such that the soil water is a dominant factor which has the greatest influence on the embolism density of the vascular plant is observed, and the soil water controls the other factors. For this reason, when the soil water is decreased, the embolism density of the vascular plant is increased, and in association with the decrease of the soil water, the rate of change of AE occurrence frequency $R_{AE}$ is also decreased. Then, when the rate of change of AE occurrence frequency $R_{AE}$ becomes 0 or less, the unrecoverable embolism after the rapid increase of water stress is occurred. Then, as surrounded with a circle of a dashed line in FIG. 13, the vascular plant begins to be wilted. Thus, the embolism density when the rate of change of AE occurrence frequency $R_{AE}$=0 corresponds to the critical embolism density at embolism density ratio $D_{AE}$=50%. Thus, we understand that water management shall be controlled such that irrigating operation of the vascular plants must be executed so that the embolism density ratios can achieve the value of or lower than at least 50%.

<Evaluation Method for Degree of Botanical-Integrity and Irrigating Method>

In the light of above discussion, an evaluation method of degree of botanical-integrity in vascular plant according to the first embodiment of the present invention and an irrigating method based upon the evaluation method may be carried out in accordance with the following procedure.

(a) As illustrated in FIG. 1, one or more of the elastic wave reception sensors 11a, 11b, 11c and 11d are fixed to the side axes $2_{b1}$, $2_{b2}$, $2_{b3}$ and $2_{b4}$ of the vascular plant, and in a period between one minute and one hour (a period between 10 minutes and 30 minutes is desirable), the detection of the elastic wave (AE) generated by the cavitation is carried out by the elastic wave reception sensors 11a, 11b, 11c and 11d. The detection number measured at this state is defined as $AE_{low}$.

(b) As illustrated in FIG. 1, the portions $C_1$, $C_2$, $C_3$ and $C_4$ allocated closer to the roots than the elastic wave reception sensors 11a, 11b, 11c and 11d of the side axes $2_{b1}$, $2_{b2}$, $2_{b3}$ and $2_{b4}$ to which the elastic wave reception sensors 11a, 11b, 11c and 11d are attached are cut (disconnected), and in the period between one minute and one hour, the detections of the elastic waves (AE) generated by the cavitation are carried out by the elastic wave reception sensors 11a, 11b, 11c and 11d, respectively. The detection number measured at this state is defined as $AE_{high}$.

(c) The rate of change of AE occurrence frequency $R_{AE}$ is calculated from Eq. (2).

(d) Whether or not the calculated rate of change of AE occurrence frequency $R_{AE}$ is 0 or less is judged and determined. If the rate of change of AE occurrence frequency $R_{AE}$ is 0 or less, it is determined that the growth-condition has arrived at the level at which the embolism cannot be recovered (the critical embolism density), and then, the botanical-integrity is evaluated. With the rate of change of AE occurrence frequency $R_{AE}$ as the index, the irrigating timing and irrigating quantity to the vascular plant are determined. For example, when water is tried to be saved to the minimum, the measurement is carried out in the nighttime. Then, when the rate of change of AE occurrence frequency $R_{AE}$ becomes 0 or less, the irrigating operation is carried out. When water-saving is carried out while the growth of the vascular plant is kept, the measurement is carried out in a time band in which water stress is the greatest in the daytime. Then, when the rate of change of AE occurrence frequency $R_{AE}$ becomes 0 or less, the irrigating operation is carried out. Also, when specified measuring methods such as the cutting of axis and the like are always same and the values of the rate of change of AE occurrence frequencies $R_{AE}$ are same, the embolism densities at the time of the specified measurement are same, and therefore, when the result of the specified measurement is used to irrigate the vascular plant with the value of the rate of change of AE occurrence frequency $R_{AE}$ as the criterion, the irrigating operation can be carried out such that the embolism density does not become a specified value or less.

In this way, by the irrigating method according to the first embodiment of the present invention, the rate of change of AE occurrence frequency $R_{AE}$ before and after the cutting of the axis of the vascular plant is measured, and we can determine the risk level of the embolism of the axis of the vascular plant. On the basis of the rate of change of AE occurrence frequency $R_{AE}$, the minimum irrigation quantity required to grow the vascular plant can be determined, which leads to save the irrigation quantity of the vascular plant and improve the quality of the fruit.

The required measurement time for the elastic wave reception sensors 11a, 11b, 11c and 11d, which are used in the evaluation method of degree of botanical-integrity in vascular plant according to the first embodiment of the present invention and the irrigating method based upon the evaluation method, depend on the sensibilities of the elastic wave reception sensors 11a, 11b, 11c and 11d and the transpiration quantity of the plant. The measurement time is required to be a period longer than the enough period such that a total vale of the sum of $AE_{low}$ and $AE_{high}$ can reach at lease one or more is always assured. Under a condition that the water stress is constant, as the measurement time is longer, the measurement precision of the rate of change of AE occurrence frequency $R_{AE}$ is improved. However, when the measurement is carried out for the excessively long time, with the change in the transpiration quantity, the solar radiation quantity, the temperature or the like, water stress is changed, which has influence on the precision. For example, when the axis of the tomato, as one example of the vascular plant, is measured, for the methodology of cutting the axis, the axes in the states before and after the cutting shall be measured, respectively, in a period between about 10 and 30 minutes.

As illustrated in FIG. 1, it is possible to carry out the measurement in a shorter time, by placing the plurality of elastic wave reception sensors 11a, 11b, 11c and 11d, and cutting the plurality of positions $C_1$, $C_2$, $C_3$ and $C_4$, and then carrying out the measurement. However, the damage to the vascular plant becomes severe. When the damage to the vascular plant is considered, a work of "pruning (training)" for adjusting the shape by cutting the strings and the branches so as to be suitable for the vascular plant to be grown and a work of "topping" for removing the excessive buds may be used to cut the axis. In the works of the pruning and the topping, an issue of the number of the main branches to be extended, an issue as to whether or not the collaterals (side branches) are extended, an issue as to whether or not the buds are cut (disconnected), and the like may be considered, on the basis of the kind of the vascular plant, the method of the cultivation, the width of a farm and the like. Typically, strong pruning and topping are carried out in the beginning of the cultivation, however, because the life of the vascular plants will be shortened when the strong pruning and topping are carried out in the latter half of the cultivation, soft pruning and topping are carried out in the latter half of the cultivation.

Or, the axis may be cut by using a work of "trimming" for cutting the crowded branches and the excessive branches. A work of "update (cutback) trimming" for cutting the branches in order to extend the young buds protruding from the bases of the main branches and collaterals (side branches) such as an eggplant is the trimming action for rejuvenating the branch, in a sense.

Second Embodiment

As described in the evaluation method of degree of botanical-integrity in vascular plant and the irrigating system according to the first embodiment, the film electret sensor exemplified in FIGS. 5 and 6 can efficiently receive the elastic wave (AE) emitted from the medium of the low acoustic impedance, such as the vascular tissue, because the acoustic impedances of the pressure reception surface (silicon resin surface) and the gap portion are low. In the film electret sensor, because the contact rigidity of the micro gap portion is low, the acoustic impedance is further low, and the reception efficiency from the vascular plant is high. Also, the film electret sensor can receive all of the waves in the frequencies 1 kHz to 1 MHz of the elastic wave (AE) in the present invention, at the flat reception sensibility. Thus, the frequency can be easily changed on the basis of the vascular plant.

Figure 14:
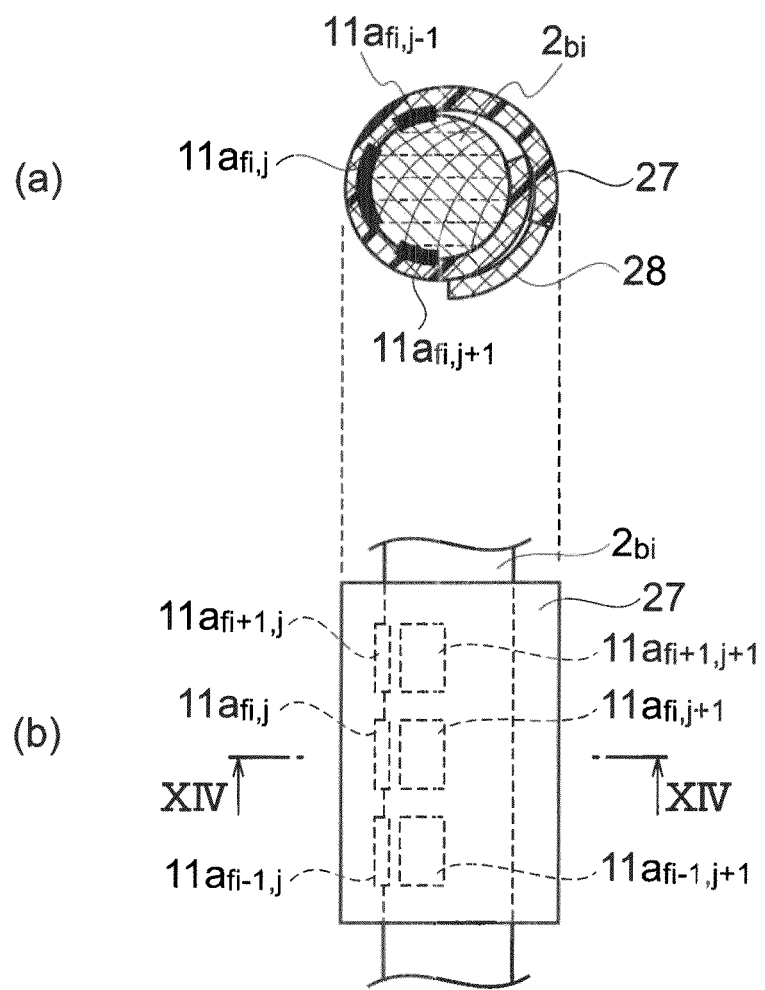
FIG. 14 are views describing a method of attaching a film ECM array as an elastic wave reception sensor (AE sensor) to the axis, in the evaluation system of the botanical-integrity in vascular plant and the irrigating system, according to a second embodiment of the present invention.
Figure 15:
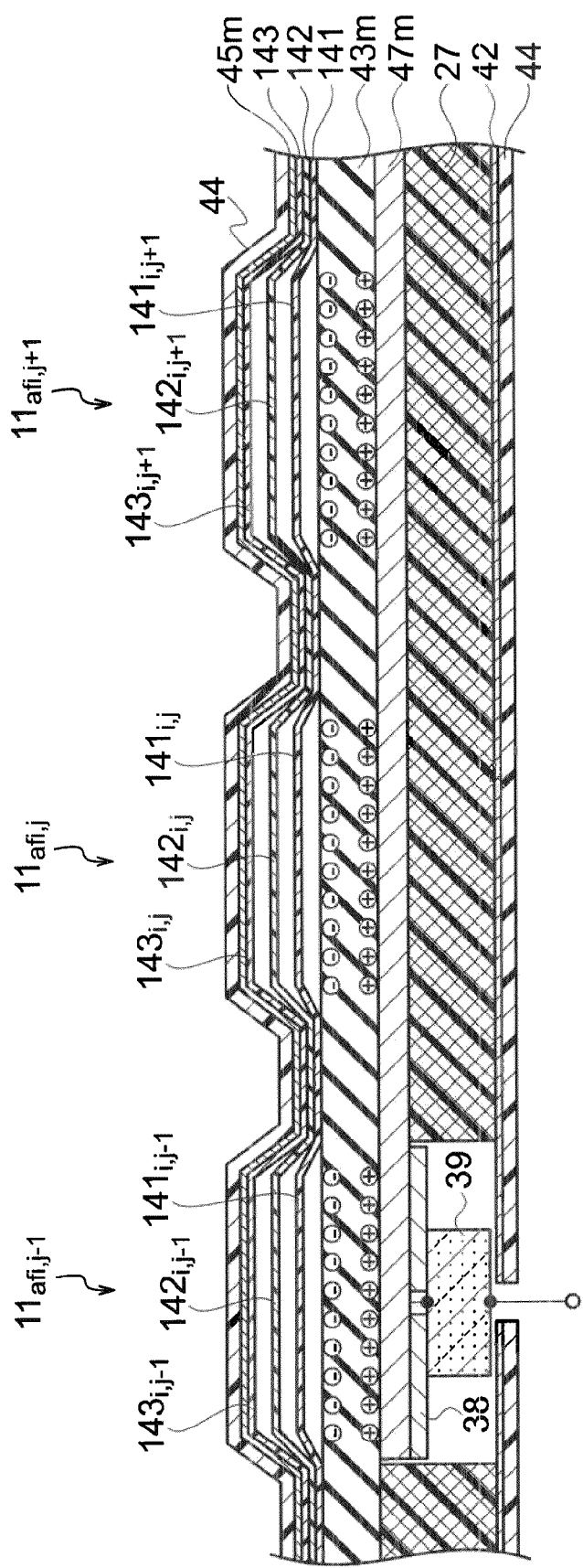
FIG. 15 is a schematic cross-sectional view describing a detailed structure of the film ECM array illustrated in FIG. 14.

In particular, because the generation source of the elastic wave (AE) is the minute xylem element, if the film electret sensor is designed as the film ECM array illustrated in FIG. 15, the reception sensibility can be further improved. Although the film ECM array may be also attached to the axis by the method illustrated in FIGS. 2 and 3, the film ECM array is desired to be wound around the axis of the side axis $2_{b1}$ or the like as illustrated in FIG. 14. In FIG. 14, the film ECM arrays ($11_{afij-1}$, $11_{afij}$, $11_{afij+1}$, - - -, 27, 28) are wound around the side axis $2_{b1}$, and the film ECM array are fixed with adhesion tape 28 connected to the tip side of the flexible base 27. On the respective surfaces of the flexible base 27 and adhesion tape 28, the loop surface and the hooked surface that are made of fibers are provided, respectively, and the loop surface and the hooked surface are scheduled to be engaged and fixed. Actually, the shape of the axis of the side axis $2_{b1}$ or the like is not smooth cylinder as schematically illustrated in FIG. 14, and there are the ups and the downs on the actual axis, the flexibility of the ECM film can be utilized to improve adhesion degree to the actual axis.

As the film ECM array according to the second embodiment illustrated in FIG. 15, when the sensing unit of the film ECM array is divided into the many elements $11_{afij-1}$, $11_{afij}$, $11_{afij+1}$, - - - (i=1 to m; j=1 to n: m and n are positive integers of two or more, respectively) and the inter-element portions between elements $11_{afij-1}$, $11_{afij}$, $11_{afij+1}$, - - - are adhered such that the film is not dislocated and when an area of the pressure reception surface of one of the elements $11_{afij-1}$, $11_{afij}$, $11_{afij+1}$, - - - belongs in a specified range, the upper limit of the entire area of the film ECM array is not limited to the above value.

As illustrated in FIG. 15, the film ECM array according to the second embodiment of the present invention includes a vibration electrode film 45m having a flat vibration surface under no-load condition, a polymer film 43m defined by a first main surface, which is flat and opposite to the vibration surface of the vibration electrode film 45m through a gap portion whose thickness is defined by a stacked structure implemented by a gap insulation film 141 of a first layer, a gap insulation film 142 of a second layer and a gap insulation film 143 of a third layer, and a second main surface being parallel and opposite to the first main surface, polarization directions are aligned in the polymer film 43m, and a back electrode film 47m in contact with the second main surface of the polymer film 43m. A vibration film protection film 44 for protecting the vibration electrode film 45m is formed on the vibration electrode film 45m. The thickness of the gap insulation film 141 of the first layer, the gap insulation film 142 of the second layer, the gap insulation film 143 of the third layer and the polymer film 43m may be set between about 1 and 50 μm, preferably between about 1 and 25 μm and further preferably between about 5 and 12 μm.

Focusing to the central element $11af_{ij}$ in FIG. 15, in the element $11af_{ij}$ implementing the film ECM array according to the second embodiment of the present invention, between the gap insulation film $141_{ij}$ of the first layer and the polymer film 43m, a first spacer (whose illustration is omitted) formed of particles of insulators, each having a particle diameter between 10 nm and 40 μm, is inserted, and between the gap insulation film $141_{ij}$ of the first layer and the gap insulation film $142_{ij}$ of the second layer, a second spacer (whose illustration is omitted) formed of particles of insulator, each having the particle diameter between 10 nm and 40 μm, is inserted, and between the gap insulation film $142_{ij}$ of the second layer and the gap insulation film $143_{ij}$ of the third layer, a third spacer (whose illustration is omitted) formed of particles of insulator, each having the particle diameter between 10 nm and 40 μm, is inserted. Consequently, the interval of the gap defined between the vibration electrode film 45m and the polymer film 43m is controlled. The gap insulation film $143_{ij}$ of the third layer and the vibration electrode film 45m are closely adhered, and the gap insulation film $143_{ij}$ of the third layer exhibits a function equivalent to the vibration electrode insulation film of the film ECM array. In this way, between the vibration electrode film 45m and the polymer film 43m, the plurality of gap insulation films $141_{ij}$, $142_{ij}$, $143_{ij}$, - - - are stacked and inserted through the spacers (whose illustrations are omitted) formed of particles of insulator, each having the particle diameter between 10 nm and 40 μm. Consequently, between the gap insulation film $143_{ij}$ of the third layer and the gap insulation film $142_{ij}$ of the second layer, between the gap insulation film $142_{ij}$ of the second layer and the gap insulation film $141_{ij}$ of the first layer, and between the gap insulation film $141_{ij}$ of the first layer and the polymer film 43m, the micro gaps are defined, respectively, which control the respective intervals in the elements $11af_{ij}$.

When the particle diameter of each of the particles serving as the first to third spacers is set to 100 μm or less, the effective surface roughness $Ra_{eff}$ of each of the surfaces of the respective micro gaps can be less than or equal to $1/10$ of the gap width in the element space defined for each element, between the bottom surface of the gap insulation film $143_{ij}$ of the third layer and the top surface of the polymer film 43m (the effective surface roughness $Ra_{eff}$ includes the bending under loading condition). However, in order to achieve the film ECM array that is flexible and high in shape free degree, the particle diameter of each of the particles serving as the first to third spacers is set between 10 nm and 10 μm, which is preferable because the entire thickness is further thin. Moreover, as a matter of course, in the range between 10 nm and 5 μm, the particle diameter closer to 10 nm is desirable. The back electrode film 47m and the polymer film 43m may be metallurgically joined, or may be adhered with the adhesive agent and the like, or may be merely brought into contact with each other by the mechanical pressure.

On the bottom surface of the back electrode film 47m, the flexible base 27 made of insulation material is stuck, and on the bottom surface of the flexible base 27, a conductive (metallic) shield conductor film 42 is formed, and on the bottom surface of the shield conductor film 42, a shield conductor protection film 44 is formed. The shield conductor protection film 44 and the shield conductor film 42 implement a shield plate. Each of the thicknesses of the flexible base 27 and the shield conductor protection film 44 can be set to a value between about 5 and 150 μm and preferably set to a value between about 50 and 100 μm. As indicated near the left end below the back electrode film 47m in FIG. 15, a semiconductor chip 39 is stored in a hollow portion formed in a part of the flexible base 27. The semiconductor chip 39 is placed (mounted) on the circuit substrate 38, in the vicinity of the left end of the back electrode film 47m. The through holes (vias) are made in the circuit substrate 38. Then, through the through holes (vias), the semiconductor chip 39 is electrically connected to the back electrode film 47m, through the solder fused in the vicinity of the left end of the back electrode film 47m. Although the illustration is omitted, the ground wiring departed from the semiconductor chip 39 is connected to the shield conductor film 42 with soldering. The semiconductor chip 39 amplifies and measures the charges that are induced in association with the displacement of the vibration electrode film 45m, between the vibration electrode film 45m and the back electrode film 47m. The vibration electrode film 45m is vibrated by receiving the acoustic wave from the exterior.

For example, in FIG. 15, a silicon resin film having a thickness of 100 μm can be used as the vibration film protection film 44, an Al film having a thickness of 10 μm can be used as the vibration electrode film 45m, the back electrode film 47m and the shield conductor film 42, the PTFE film having a thickness of 50 μm can be used as the flexible base 27, the PFA film having a thickness of 10 μm can be used as the polymer film 43m, and the three PFA films each having a thickness of 5 μm can be used as the gap insulation film 141 of the first layer, the gap insulation film 142 of the second layer and the gap insulation film 143 of the third layer, respectively. Since the vibration film protection film 44 serves as the matching layer for increasing the adhesive property to the vascular plant and the matching property of the acoustic impedance, the vibration film protection film 44 is desired to be the flexible resin layer. For the vibration electrode film 45m, by depositing an Al film on the gap insulation film 143 of the third layer, the vibration electrode film 45m and the gap insulation film 143 of the third layer are closely adhered. Similarly, for the back electrode film 47m by depositing another Al film on the polymer film 43m, the polymer film 43m and the back electrode film 47m are closely adhered, and for the shield conductor film 42 by depositing still another Al film on the flexible base 27, the flexible base 27 and the shield conductor film 42 are closely adhered.

In the film ECM array according to the second embodiment illustrated in FIG. 15, the inter-element portion between the element $11af_{ij-1}$ and the element $11af_{ij}$ and the portion between the element $11af_{ij}$ and the element $11af_{ij+1}$ are adhered by thermal compression bonding and the like. Thus, the thicknesses of the inter-element portions are thinner than the portions of the elements $11_{afij-1}, 11_{afij}, 11_{afij+1}, ----$. In the polymer film 43m, the corona discharge is generated by needle electrodes, above the regions corresponding to the elements $11_{afij-1}, 11_{afij}, 11_{afij+1}, ----$, and the polymer film 43m is film-electrified, and the electret region is generated in each of the elements $11_{afij-1}, 11_{afij}, 11_{afij+1}, ----$.

Also, as materials for the film ECM array according to the second embodiment, the ferroelectric material such as PZT and $LiNbO_3$ can be used as the polymer films 43m of the elements $11_{afij-1}, 11_{afij}, 11_{afij+1}, ----$. However, because the flexibility is reduced in the film ECM array with ferroelectric material such as PZT and $LiNbO_3$, the deformation can be achieved only between the element $11af_{ij-1}$ and the element $11af_{ij}$ and between the element $11af_{ij}$ and the element $11af_{ij+1}$ and the like.

Figure 16:
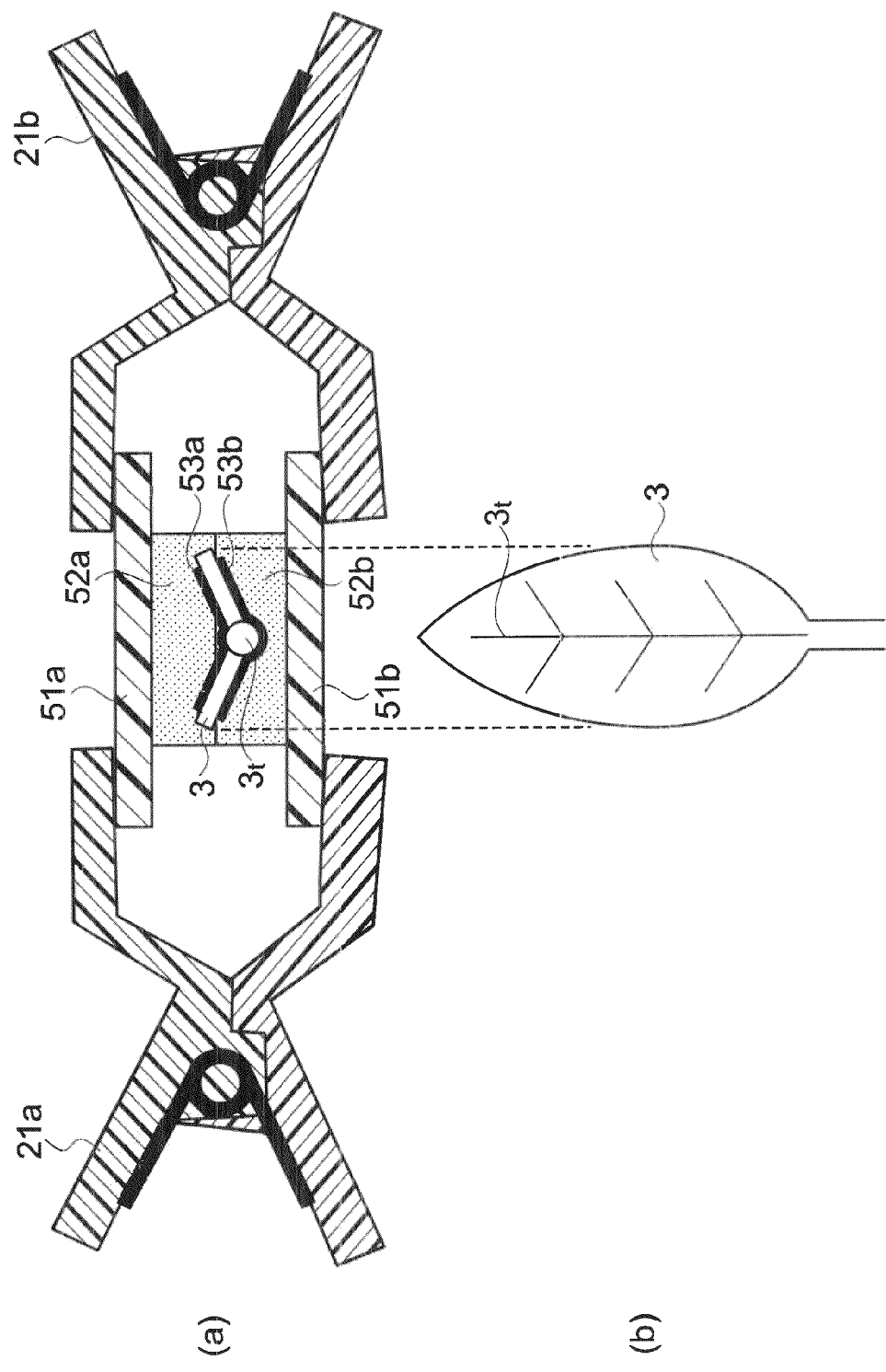
FIG. 16 is a schematic view describing a situation in which the film ECM array is not still pushed down, when the film ECM array is sandwiched between both sides of a leaf and then the elastic wave (AE) emitted from a vein of the leaf is detected, in the evaluation system of the botanical-integrity in vascular plant and the irrigating system according to the second embodiment.
Figure 17:
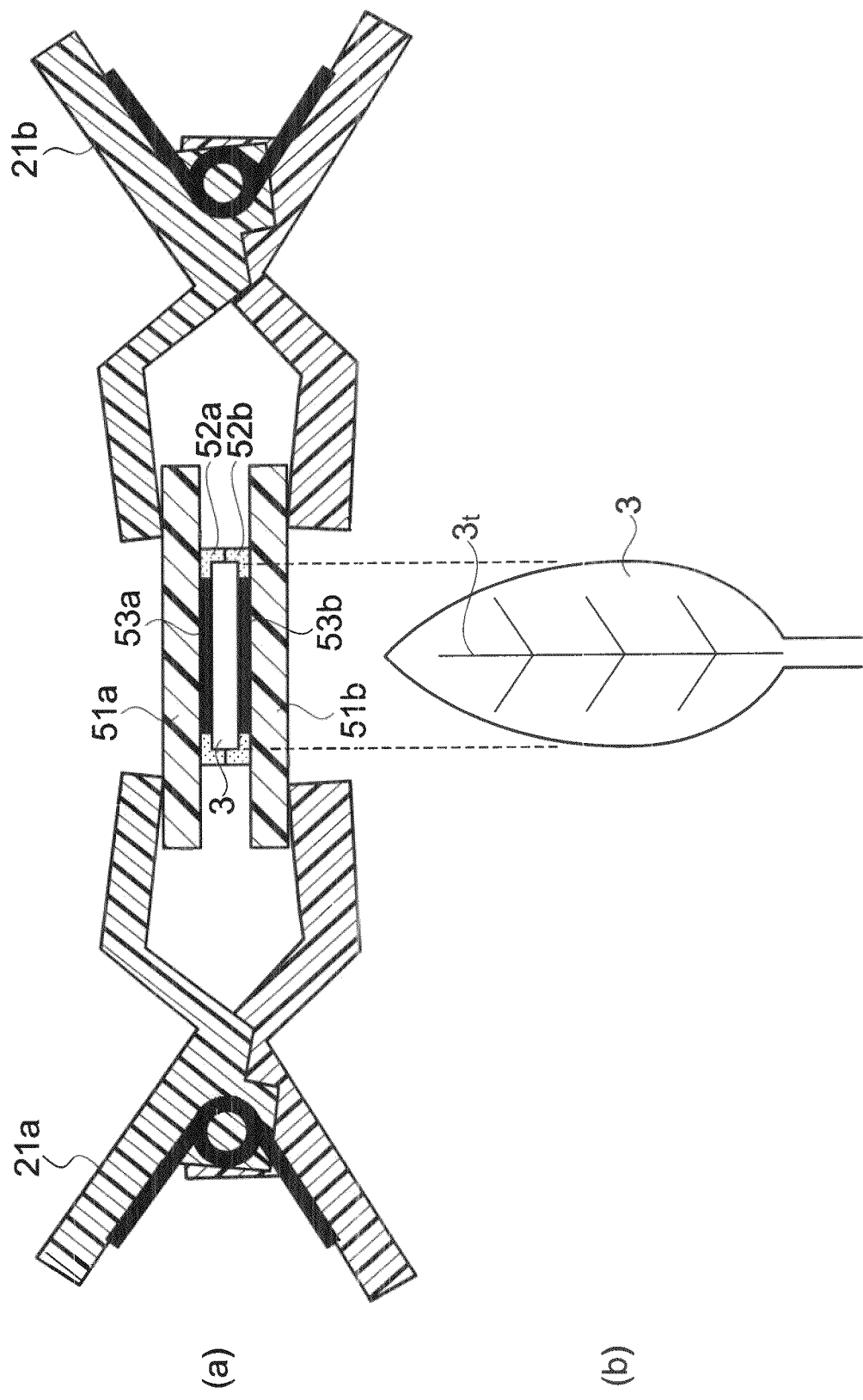
FIG. 17 is a schematic view describing a situation in which with a left clip and a right clip, the film ECM array is pushed against the vein of the leaf from both of the sides.

In the present Specification, in addition to the main axis $2_t$ and the side axes $2_{b1}, 2_{b2}, 2_{b3}, 2_{b4}, ---$, the components including a vein $3_t$ illustrated in FIGS. 16(b) and 17(b) and the like are defined as the "axes". Therefore, in view of the flexibilities and the high reception sensibility of film ECM arrays 53a and 53b, by sandwiching a leaf 3 through sponges 52a, 52b as illustrated in FIGS. 16 and 17, it is possible to detect the elastic wave (AE) emitted from the vein $3_t$ of the leaf 3.

In FIG. 16, the film ECM array 53a is arranged on the leaf 3, and the film ECM array 53b is arranged under the leaf 3. Then, the sponge 52a is placed on the film ECM array 53a, and a pushing plate 51a is placed on the sponge 52a. Moreover, the sponge 52b is placed under the film ECM array 53b, and a pushing plate 51b is placed under the sponge 52b. Then, with a left clip 21a and a right clip 21b, the pushing plate 51a and the pushing plate 51b are pushed down, which can compress the sponges 52a, 52b as illustrated in FIG. 17 and can detect the elastic wave (AE) emitted from the vein $3_t$ of the leaf 3.

Third Embodiment

In the first embodiment, the reason why the axis is cut at the positions $C_1, C_2, C_3$ and $C_4$ illustrated in FIG. 1 is to rapidly apply water stress. As another methodology, there is a scheme of sticking a needle into the axis and open a hole or polish an epidermis and send water, which flows through the xylem, to the surface outside the axis and then applies water stress.

Figure 18:
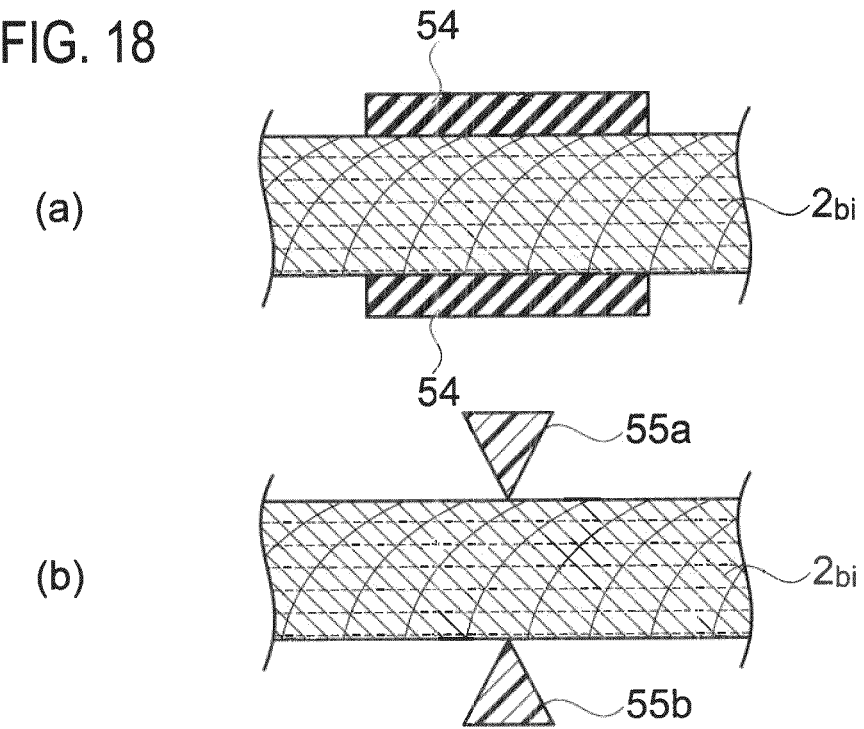
FIG. 18(a) is a schematic cross-sectional view describing a method that, in the evaluation system of the botanical-integrity in vascular plant and the irrigating system according to a third embodiment, pushing plates are arranged on both sides of the axis, and the axis is fastened with surface contact, and water stress is applied.
FIG. 18(b) is a schematic cross-sectional view describing a method, which arranges wedges on both of the sides, and fastens the axis with point contact, and then gives water stress.
Figure 19:
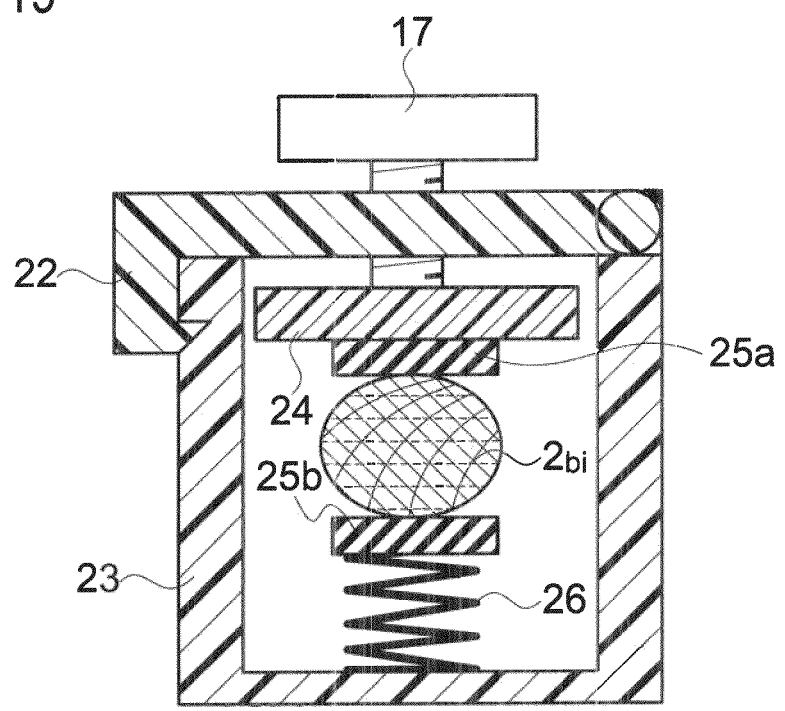
FIG. 19 is a schematic cross-sectional view describing a scheme in which in the evaluation system of the botanical-integrity in vascular plant and the irrigating system according to the third embodiment, a fastening tool is used, and the pushing plate is fastened from both sides by the rotation of a screw, and water stress is given to the axis.

Also, there is a still another methodology, which as illustrated in FIG. 18(a), arranges a pushing plate 54 on both of the sides of the axis of the side axis $2_{b1}$ or the like, and fastens and pressures the axis with the surface contact and increases water flow resistance of the xylem and then gives water stress, and a yet still another methodology, which as illustrated in FIG. 18(b), arranges wedges 55a, 55b on both of the sides of the axis, such as the side axis $2_{b1}$ or the like, and fastens and pressures the axis with the point contact and increases water flow resistance of the xylem and then gives water stress. Specifically, as illustrated in FIG. 19, the screw 17 may be pushed down to fasten (pressure) the side axis $2_{b1}$ with the point contact or surface contact. The configuration illustrated in FIG. 19 encompasses a main body 23 having U-shaped cross-section, a spring 26 provided at the bottom of the main body 23, a cover 22 being attached to the top of the main body 23 in a rotatable configuration, the cover 22 has a hook engaged with a groove near the other top of the main body 23, a fixing tool having a screw 17 provided through the cover 22, and a rotation buffer 24 placed at a tip of the screw 17, the screw 17 can push down the rotation buffer 24 by rotating the screw 17 with respect to the cover 22. The rotation buffer 24 is so attached at the tip of the screw 17 that the rotation buffer 24 becomes free against the rotation of the screw 17, because the rotation buffer 24 has a rectangular flat pattern that can suppress the rotation of rotation buffer 24, by bringing the rotation buffer 24 into contact with the inner wall of the main body 23, thereby serving as a buffer for the rotation of the screw 17. A first pushing plate 25b is arranged on the spring 26, the side axis $2_{b1}$ is arranged on the first pushing plate 25b, a second pushing plate 25a is arranged on the side axis $2_{b1}$, and the hook of the cover 22 is engaged with the groove of the main body 23. After that, the screw 17 is rotated with respect to the cover 22, and the rotation buffer 24 is pushed down. Consequently, the second pushing plate 25a can be pushed against the side axis $2_{b1}$, and the first pushing plate 25b can be pushed against the side axis $2_{b1}$, and water flow resistance of the side axis $2_{b1}$ is increased, and water stress can be applied.

Figure 20:
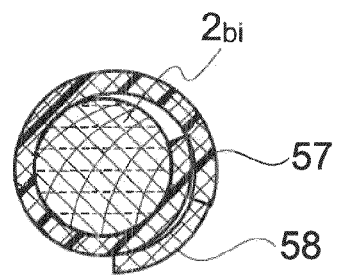
FIG. 20 is a schematic cross-sectional view describing a scheme in which in the evaluation system of the botanical-integrity in vascular plant and the irrigating system according to the third embodiment, a pressuring bag is used to fasten the axis so that water stress is given to the axis.

Or, as illustrated in FIG. 20, a pressuring bag 57 similar to a case of a blood pressure measurement may be used to fasten (pressure) the axis such as the side axis $2_{b1}$ or the like. In FIG. 20, the pressuring bag 57 is fixed with an adhesive tape (surface fastener) 58 placed around the pressuring bag 57. The loop surface and the hooked surface that are made of fibers are provided on the surfaces of the pressuring bag 57 and the adhesive tape 58, respectively. Then, the loop surface and the hooked surface may be engaged and fixed. Or, a band such as a bundling band may be used to fasten (pressure) the axis such as the side axis $2_{b1}$ or the like.

In the scheme of fastening (pressuring) the axis, a contraction rate of the diameter of the fastening direction of the axis (the diameter of the axis when the axis is fastened from all directions) is preferred to be in a range between 10% and 50%.

In the scheme of fastening the axis, when FIG. 1 is referred as an example, in a side axis $2_{b1}$, by fastening (pressuring) the side axis $2_{b1}$ at the position $C_1$ allocated at closer portion to the root than the position of the elastic wave reception sensor 11a, water stress is rapidly varied, in a side axis $2_{b2}$, by fastening the side axis $2_{b2}$ at the position $C_2$ allocated at closer portion to the root than the position of the elastic wave reception sensor 11b, water stress is rapidly varied, in a side axis $2_{b3}$, by fastening the side axis $2_{b3}$ at the position $C_3$ allocated at closer portion to the root than the position of the elastic wave reception sensor 11c, water stress is rapidly varied, and in a side axis $2_{b4}$, by fastening the side axis $2_{b4}$ at the position $C_4$ allocated at closer portion to the root than the position of the elastic wave reception sensor 11$d$, water stress is rapidly varied. Then, ratio of the AE occurrence frequencies between before and after the variations of those water stresses are examined, respectively. Then, with the $AE_{low}$ defined as the AE occurrence frequency of the vascular plant when water stress is low, and the $AE_{high}$ defined as the AE occurrence frequency of the vascular plant when water stress is high, the change rate of the occurrence frequency of the elastic wave (rate of change of AE occurrence frequency $R_{AE}$) can be defined by Eq. (2).

Thus, an evaluation method of degree of botanical-integrity in vascular plant according to the third embodiment of the present invention and an irrigating method based upon the evaluation method may be carried out in accordance with the following procedure.

(a) As illustrated in FIG. 1, one or more of the elastic wave reception sensors 11$a$, 11$b$, 11$c$ and 11$d$ are fixed to the side axes $2_{b1}$, $2_{b2}$, $2_{b3}$ and $2_{b4}$ of the vascular plant, and in a period between one minute and one hour (a period between 10 minutes and 30 minutes is desirable), the detection of the elastic wave (AE) generated by the cavitation is carried out by the elastic wave reception sensors 11$a$, 11$b$, 11$c$ and 11$d$. The detection number measured at this state is defined as $AE_{low}$.

(b) As illustrated in FIG. 1, the portions $C_1$, $C_2$, $C_3$ and $C_4$ allocated closer to the root than the elastic wave reception sensors 11$a$, 11$b$, 11$c$ and 11$d$ of the side axes $2_{b1}$, $2_{b2}$, $2_{b3}$ and $2_{b4}$ to which the elastic wave reception sensors 11$a$, 11$b$, 11$c$ and 11$d$ are attached are fastened, and in the period between one minute and one hour (the period between 10 minutes and minutes is desirable), the detections of the elastic waves (AE) generated by the cavitation are carried out by the elastic wave reception sensors 11$a$, 11$b$, 11$c$ and 11$d$, respectively. The detection number measured at this state is defined as $AE_{high}$.

(c) The rate of change of AE occurrence frequency $R_{AE}$ is calculated from Eq. (2).

(d) Whether or not the calculated rate of change of AE occurrence frequency $R_{AE}$ is 0 or less is judged and determined. If the rate of change of AE occurrence frequency $R_{AE}$ is 0 or less, it is determined that the growth-condition has arrived at the critical embolism density at which the embolism cannot be recovered, and then, the botanical-integrity is evaluated. With the rate of change of AE occurrence frequency $R_{AE}$ as the index, the irrigating timing and irrigating quantity to the vascular plant are determined. For example, when water is tried to be saved to the minimum, the measurement is carried out in the nighttime. Then, when the rate of change of AE occurrence frequency $R_{AE}$ becomes 0 or less, the irrigating operation is carried out. When water-saving is carried out while the growth of the vascular plant is kept, the measurement is carried out in the time band in which water stress is the greatest in the daytime. Then, when the rate of change of AE occurrence frequency $R_{AE}$ becomes 0 or less, the irrigating operation is carried out. Also, when specified measuring methods such as the fastening of axis and the like are always same and the values of the rate of change of AE occurrence frequencies $R_{AE}$ are same, the embolism densities at the time of the specified measurement are same, and therefore, when the result of the specified measurement is used to irrigate the vascular plant with the value of the rate of change of AE occurrence frequency $R_{AE}$ as the criterion, the irrigating operation can be carried out such that the embolism density does not become a specified value or less.

In this way, by the irrigating method according to the third embodiment of the present invention, the rate of change of AE occurrence frequency $R_{AE}$ before and after the fastening of the axis of the vascular plant is measured, and we can determine the risk level of the embolism of the axis of the vascular plant. On the basis of the rate of change of AE occurrence frequency $R_{AE}$, the minimum irrigation quantity required to grow the vascular plant can be determined, which leads to save the irrigation quantity of the vascular plant and improve the quality of the fruit.

The required measurement time for the elastic wave reception sensors 11$a$, 11$b$, 11$c$ and 11$d$, which are used in the evaluation method of degree of botanical-integrity in vascular plant according to the third embodiment of the present invention and the irrigating method based upon the evaluation method, depend on the sensibilities of the elastic wave reception sensors 11$a$, 11$b$, 11$c$ and 11$d$ and the transpiration quantity of the plant. The measurement time is required to be a period longer than the enough period such that a total vale of the sum of $AE_{low}$ and $AE_{high}$ can reach at lease one or more is always assured. Under a condition that the water stress is constant, as the measurement time is longer, the measurement precision of the rate of change of AE occurrence frequency $R_{AE}$ is improved. However, when the measurement is carried out for the excessively long time, with the change in the transpiration quantity, the solar radiation quantity, the temperature or the like, water stress is changed, which has influence on the precision. In the case of fastening, the measurement time depends on the fastening force. Typically, the measurement time is required to be long, as compared with the case of the cutting described in the first embodiment.

According to the evaluation method of degree of botanical-integrity in vascular plant pertaining to the third embodiment of the present invention and the irrigating method based upon the evaluation method, differently from the evaluation method of degree of botanical-integrity in vascular plant according to the first embodiment illustrated in FIG. 1 and the irrigating method based upon the evaluation method, because the axis is not cut, the damage to the vascular plant is small.

Fourth Embodiment

Figure 21:
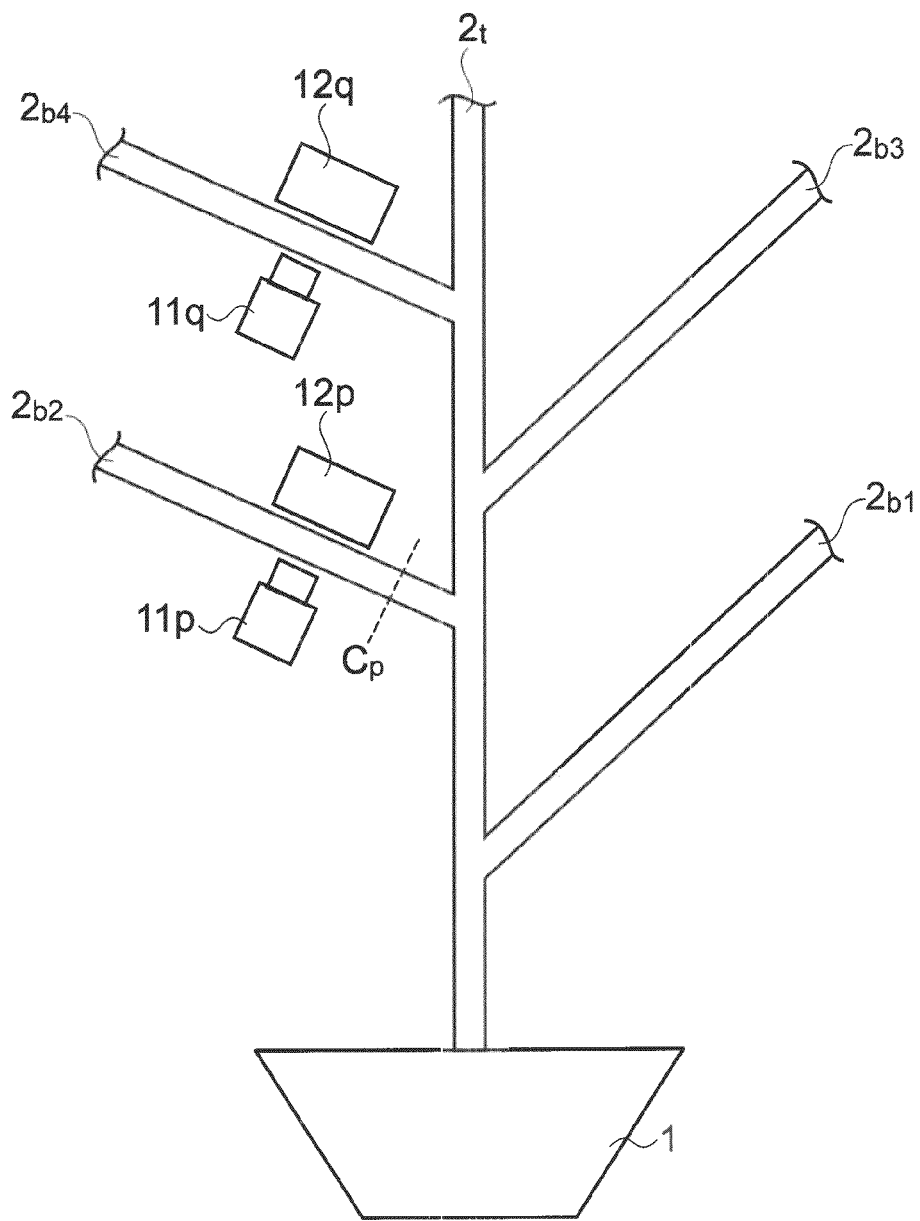
FIG. 21 is a schematic view describing a rough configuration of the evaluation system of the botanical-integrity in vascular plant and the irrigating system according to a fourth embodiment of the present invention, in which a plurality of elastic wave reception sensors (AE sensors) are placed in a plurality of axes, and then, only a single axis is cut off.

As illustrated in FIG. 21, similarly to the first embodiment, an evaluation method of degree of botanical-integrity in vascular plant and the irrigating system, according to the fourth embodiment of the present invention, targets the vascular plant of the single axis branch, which has the main axis (stalk) $2_t$ uprightly standing on the ground from the soil stored in the flower pot 1 and the plurality of side axes (branches) $2_{b1}$, $2_{b2}$, $2_{b3}$, $2_{b4}$, - - - branched from the main axis $2_t$. However, an elastic wave reception sensor 11$p$ is attached through a rubber sheet 12$p$ to the side axis $2_{b2}$, and an elastic wave reception sensor 11$q$ is attached through a rubber sheet 12$q$ to the side axis $2_{b4}$. FIG. 21 exemplifies the two elastic wave reception sensors 11$p$, 11$q$. However, the elastic wave reception sensor (AE sensor) may be further placed in the side axes $2_{b1}$, $2_{b3}$, - - - .

The evaluation method of degree of botanical-integrity in vascular plant according to the fourth embodiment of the present invention and the irrigating method based upon the evaluation method may be carried out in accordance with the following procedure.

(a) As illustrated in FIG. 21, two or more of the elastic wave reception sensors 11$p$, 11$q$, - - - are placed. Then, only the side axis $2_{b2}$ is cut (disconnected), but the other side axes such as the side axis $2_{b4}$ and the like are not cut. That is, in the side axis $2_{b2}$, at a position $C_p$ allocated at closer portion to the root than the position of the elastic wave reception sensor 11$p$ so that water stress is rapidly varied. Then, in the period between one minute and one hour, the elastic wave (AE) generated by the cavitation is detected by the elastic wave reception sensor $11p$. Here, the detection number of the elastic waves (AE) of the elastic wave reception sensor $11p$ attached to the side axis $2_{b2}$ that is cut (disconnected) is defined as $AE_{high}$, and the detection number of the elastic waves (AE) of the elastic wave reception sensor $11q$ attached to the other side axis $2_{b4}$ that is not cut is defined as $AE_{low}$.

(b) The change rate of the occurrence frequency of the elastic wave (rate of change of AE occurrence frequency $R_{AE}$) is calculated from Eq. (2).

(c) Whether or not the calculated rate of change of AE occurrence frequency $R_{AE}$ is 0 or less is judged and determined. If the rate of change of AE occurrence frequency $R_{AE}$ is 0 or less, it is determined that the growth-condition has arrived at the critical embolism density, and then, the botanical-integrity is evaluated. With the rate of change of AE occurrence frequency $R_{AE}$ as the index, the irrigating timing and irrigating quantity to the vascular plant are determined. For example, when water is tried to be saved to the minimum, the measurement is carried out in the nighttime. Then, when the rate of change of AE occurrence frequency $R_{AE}$ becomes 0 or less, the irrigating operation is carried out. When water-saving is carried out while the growth of the vascular plant is kept, the measurement is carried out in the time band in which water stress is the greatest in the daytime. Then, when the rate of change of AE occurrence frequency $R_{AE}$ becomes 0 or less, the irrigating operation is carried out. Also, when specified measuring methods such as the cutting of axis and the like are always same and the values of the rate of change of AE occurrence frequencies $R_{AE}$ are same, the embolism densities at the time of the specified measurement are same, and therefore, when the result of the specified measurement is used to irrigate the vascular plant with the value of the rate of change of AE occurrence frequency $R_{AE}$ as the criterion, the irrigating operation can be carried out such that the embolism density does not become a specified value or less.

In this way, by the irrigating method according to the fourth embodiment of the present invention, the rate of change of AE occurrence frequency $R_{AE}$ before and after the cutting of the axis of the vascular plant is measured, and we can determine the risk level of the embolism of the axis of the vascular plant. On the basis of the rate of change of AE occurrence frequency $R_{AE}$, the minimum irrigation quantity required to grow the vascular plant can be determined, which leads to save the irrigation quantity of the vascular plant and improve the quality of the fruit.

The required measurement time for the elastic wave reception sensors $11a$, $11b$, $11c$ and $11d$, which are used in the evaluation method of degree of botanical-integrity in vascular plant according to the fourth embodiment of the present invention and the irrigating method based upon the evaluation method, depend on the sensibilities of the elastic wave reception sensors $11a$, $11b$, $11c$ and $11d$ and the transpiration quantity of the plant. The measurement time is required to be a period longer than the enough period such that a total value of the sum of $AE_{low}$ and $AE_{high}$ can reach at lease one or more is always assured. Under a condition that the water stress is constant, as the measurement time is longer, the measurement precision of the rate of change of AE occurrence frequency $R_{AE}$ is improved. However, when the measurement is carried out for the excessively long time, with the change in the transpiration quantity, the solar radiation quantity, the temperature or the like, water stress is changed, which has influence on the precision. For example, when the axis of the tomato, as one example of the vascular plant, is measured, for the methodology of cutting the axis, the axes in the states before and after the cutting shall be measured, respectively, in a period between about 10 and 30 minutes.

As illustrated in FIG. 21, the plurality of elastic wave reception sensors $11p$, $11q$ are placed, and only one position $C_p$ is cut (disconnected). Thus, the damage to the vascular plant is suppressed as compared with the evaluation method of degree of botanical-integrity in vascular plant according to the first embodiment and the irrigating method based upon the evaluation method. However, even in cutting only one position, there is still damage to the vascular plant. Thus, the axis may be cut by using the work of pruning, topping or trimming.

In the present Specification, in addition to the main axis $2_t$ and the side axes $2_{b1}$, $2_{b2}$, $2_{b3}$, $2_{b4}$, - - - , the components including the petiole (leaf stalk), the vein and the like are defined as the "axes". Thus, the attachment positions of the two elastic wave reception sensors $11p$, $11q$ may be not only the side axes $2_{b1}$, $2_{b2}$, $2_{b3}$ and $2_{b4}$, but also the main axis $2_t$ and the petiole (leaf stalk). However, the axis or petiole (leaf stalk) in the similar state is desired to be selected.

Also, the two sensors may be attached to one axis or petiole (leaf stalk), and the portion between the sensors may be cut. When the portion between the sensors is cut (disconnected), the detection number of the elastic waves (AE) of the sensor placed at the portion allocated closer to the root than the cut (disconnected) location becomes $AE_{low}$.

Fifth Embodiment

In the evaluation method of degree of botanical-integrity in vascular plant according to the first to fourth embodiments of the present invention and the irrigating method based upon these evaluation methods, the axis of the vascular plant is cut (disconnected) or fastened (pressured) to apply water stress. An evaluation method of degree of botanical-integrity in vascular plant according to a fifth embodiment of the present invention and an irrigating method that uses the irrigating method are directed to a method in which there is no necessity of giving the damage, such as the cut and the like, to the axis of the vascular plant. That is, the evaluation method of degree of botanical-integrity in vascular plant according to the fifth embodiment of the present invention and the irrigating method based upon the evaluation method may be carried out in accordance with the following procedure.

(a) One or more elastic wave reception sensors (AE sensors) are placed on the axes of the vascular plant, and the elastic wave (AE) is measured for a long period. The transpiration is stopped in the nighttime, and water stress is decreased, and then, the detection number of the elastic waves (AE) is assumed to $AE_{low}$. Also, when the transpiration is carried out in the daytime, water stress is increased, therefore, the detection number of the elastic waves (AE) is defined as $AE_{high}$.

(b) The change rate of the occurrence frequency of the elastic wave (rate of change of AE occurrence frequency $R_{AE}$) is calculated from Eq. (2).

(c) Whether or not the calculated rate of change of AE occurrence frequency $R_{AE}$ is 0 or less is judged and determined. If the rate of change of AE occurrence frequency $R_{AE}$ is 0 or less, it is determined that the growth-condition has arrived at the critical embolism density, and then, the botanical-integrity is evaluated. With the rate of change of AE occurrence frequency $R_{AE}$ as the index, the irrigating timing and irrigating quantity to the vascular plant are determined.

In the evaluation method of degree of botanical-integrity in vascular plant according to the fifth embodiment and the irrigating method based upon the evaluation method, the measurement times of the AE occurrence frequency $AE_{low}$ when water stress in the nighttime is decreased and the AE occurrence frequency $AE_{high}$ when water stress in the daytime is increased are required to be always constant. Desirably, the measurement time of the AE occurrence frequency $AE_{low}$ of the nighttime is between one and six hours until just before the daybreak, and the measurement time of the AE occurrence frequency $AE_{high}$ of the daytime is between one and six hours until just before the sunset. Also, the irrigating operation must not be carried out in the measurement time band between the AE occurrence frequency $AE_{low}$ of the nighttime and the AE occurrence frequency $AE_{high}$ of the daytime.

The evaluation method of degree of botanical-integrity in vascular plant according to the fifth embodiment and the irrigating method based upon the evaluation method are the methods that evaluate the botanical-integrity by judging whether or not the embolism density of the nighttime arrives at the critical embolism density, when the soil is gradually cried. However, the difference between water stresses of the nighttime and the daytime is changed depending on the solar radiation quantity of the daytime, the soil water and the like. However, because the criterion such that the rate of change of AE occurrence frequency $R_{AE}=0$ means the state when the embolism density has arrived up to the critical embolism density is not changed, the irrigating operation can be carried out with the rate of change of AE occurrence frequency $R_{AE}=0$ as the criterion.

The evaluation method of degree of botanical-integrity in vascular plant according to the fifth embodiment and the irrigating method based upon the evaluation method can evaluate the botanical-integrity only with regard to the arrival at the critical embolism density. Thus, even if the measuring method is same, and the rate of change of AE occurrence frequency $R_{AE}$ is same, the embolism density is not always same except for the state in which the rate of change of AE occurrence frequency $R_{AE}=0$. However, according to the evaluation method of degree of botanical-integrity in vascular plant pertaining to the fifth embodiment and the irrigating method based upon the evaluation method, there is no necessity of giving the damage, such as the cut and the like, to the vascular plant. Also, since the measurement is executed consecutively for a long period, the irrigating method according to the fifth embodiment can be incorporated to the system for automatically controlling the irrigating operation.

Sixth Embodiment

An evaluation method of degree of botanical-integrity in vascular plant according to the sixth embodiment of the present invention and an irrigating method based upon the evaluation method provide another methodology in which there is no necessity of giving the damage, such as the cut and the like, to the axis of the vascular plant, similarly to the evaluation method of degree of botanical-integrity in vascular plant according to the fifth embodiment and the irrigating method based upon the evaluation method. That is, the evaluation method of degree of botanical-integrity in vascular plant according to the sixth embodiment of the present invention and the irrigating method based upon the evaluation method may be carried out in accordance with the following procedure.

(a) One or more elastic wave reception sensors (AE sensors) are placed on the axes of the vascular plant, and the elastic wave (AE) is measured before and after the irrigating operation. When water stress is great before the irrigating operation, the detection number of the elastic waves (AE) is assumed to $AE_{high}$. When water stress is small after the irrigating operation, the detection number of the elastic waves (AE) is defined as $AE_{low}$.

(b) The change rate of the occurrence frequency of the elastic wave (rate of change of AE occurrence frequency $R_{AE}$) is calculated from Eq. (2).

(c) Whether or not the calculated rate of change of AE occurrence frequency $R_{AE}$ is 0 or less is judged and determined. If the rate of change of AE occurrence frequency $R_{AE}$ is 0 or less, it is determined that the growth-condition has arrived at the critical embolism density, and then, the botanical-integrity is evaluated. With the rate of change of AE occurrence frequency $R_{AE}$ as the index, the irrigating timing and irrigating quantity to the vascular plant are determined.

In the evaluation method of degree of botanical-integrity in vascular plant according to the sixth embodiment and the irrigating method based upon the evaluation method, the measurement times of the AE occurrence frequency $AE_{low}$ when water stress is decreased after the irrigating operation and the AE occurrence frequency $AE_{high}$ when water stress is increased before the irrigating operation are required to be always constant. Also, when the rate of change of AE occurrence frequency $R_{AE}$ is evaluated, the respective measurement times of each of the repeated measurements is also desired to be constant. The measurement time of the AE occurrence frequency $AE_{high}$ before the irrigating operation is between one minute and one hour until before the irrigating operation, and the measurement time of the AE occurrence frequency $AE_{low}$ after the irrigating operation is between one minute and one hour from after the finish of the irrigating operation.

According to the evaluation method of degree of botanical-integrity in vascular plant pertaining to the sixth embodiment and the irrigating method based upon the evaluation method, when the irrigation quantity is constant in the irrigating operation on each time, it is possible to evaluate the rate of change of AE occurrence frequency $R_{AE}$. Even if the irrigation quantity is varied, it is possible to detect the critical embolism. Moreover, there is no necessity of giving the damage such as the cut and the like. Also, elastic wave reception sensors (AE sensors) can be attached only at the time of the irrigating operation, and the measurement can be carried out in a short time. Since the measurement can be executed consecutively for the long period, the irrigating method pertaining to the sixth embodiment can be incorporated in the system for automatically controlling the irrigating operation.

When the plant is cultivated on a dry land, the salt damage against plant becomes severe problem. The salt damage is generated because the salt component in the soil is accumulated by the irrigating operation. The salt damage is generated by the segregation of the salt, which will be described below. Since water of the quantity greater than the quantity that is absorbed from the roots by the plant is given at the time of the irrigating operation, water permeates into the deep portion of the soil, and as a result, the salt dissolves from the soil into water, and when water is vaporized and pulled up by capillarity, the salt is segregated, which results in the foregoing salt damage. Thus, the action for decreasing the irrigation quantity as much as possible leads to the protection of the salt damage. However, the minimal required irrigation quantity is changed with the growth of the plant. Also, the development state of the roots cannot be known only by the observation on the ground. Thus, it is impossible to determine the minimal required irrigation quantity. According to the evaluation method of degree of botanical-integrity in vascular plant pertaining to the sixth embodiment and the irrigating method based upon the evaluation method, the irrigating operation is carried out under the condition close to the critical embolism density. Hence, the minimal required irrigation quantity can be carried out independently of the growth state of the plant.

Seventh Embodiment

FIG. 22(a) illustrates a cross-section of the axis of the miniature tomato as one example of the vascular plant. However, a vascular tissue $2_{ti}$ of a thickness t is annually formed on the inner side of an annual epidermis $2_{th}$ serving as the outermost layer of the axis $2_t$. Then, a marrow $2_{tc}$ is formed on the center of the axis serving as the inner side of the vascular tissue $2_{ti}$. Although the detailed illustration is omitted, the annual vascular tissue $2_{ti}$ of the thickness t has the triple-layer structure in which an annual vascular formation layer exists in the outermost layer, and an annual phloem exists in the inner side of the vascular formation layer, and an annual xylem exists in the further inner side of the phloem.

The vascular tissue $2_{ti}$ of the vascular plant in herbaceous plants is the densest in the tissue of the axis and has the rigidity. In the vascular plant in woody plants, the vascular tissue $2_{ti}$ in the vein is the densest in the tissue of the axis and has the rigidity. For example, as illustrated in FIG. 22(b), when the vascular tissue $2_{ti}$ is annually formed on the main axis $2_t$ and when an acoustic wave of a wavelength sufficiently larger than the thickness t of the vascular tissue $2_{ti}$ is entered from the surface of the main axis $2_t$, an acoustic wave $\phi$ referred to as a "guide wave" is generated in the inside of the vascular tissue $2_{ti}$ and propagated through the vascular tissue $2_{ti}$.

The "guide wave" implies the ultrasonic wave transmitted in a longitudinal direction on a boundary, in a flat plate, a circular tube, a cylinder and the like. In the guide wave, many modes exist in the same frequency band. However, in any mode, its sound velocity is changed depending on the product of the thickness of the plate (a cylinder diameter D in the case of the cylinder) and a frequency f. Such a phenomenon is referred to as a frequency dispersion. In the case of the axis of the vascular plant illustrated in FIG. 22, when the ultrasonic wave is transmitted only through the vasculature, the ultrasonic wave becomes the guide wave propagated through the circular tube, and when the ultrasonic wave is propagated through the entire axis, the ultrasonic wave becomes the guide wave propagated through the cylinder. In both of the guide waves, when a wavelength λ of the guide wave is sufficiently longer than the thickness t of the vascular tissue or a diameter D of the main axis, the frequency dispersion is generated. For example, when the guide waves of a longitudinal wave mode in an aluminum circular tube and cylinder are listed as the examples (refer to (J. L. Rose), "ultrasonic waves in solid media", (Cambridge university press), 1999, p 143-168), in order to generate the frequency dispersion in the circular tube wave of the longitudinal wave mode, the wavelength λ may be three times or more of the plate thickness t, and in order to generate the frequency dispersion in the cylinder wave of the longitudinal wave mode, the wavelength λ may be ⅔ or more of the cylinder diameter D. The value the wavelength λ is determined by the material of the medium through which the ultrasonic wave is transmitted (an elastic modulus and a Poisson's ratio). However, in the case of the vascular plant, the wavelength λ is roughly required to be longer than the thickness t of the vascular tissue or the half of the diameter D of the main axis, and desired to be longer than the thickness t of the vascular tissue or two times or more of the diameter D of the main axis.

As for the acoustic wave (guide wave) $\phi$ propagated through the vascular tissue, when the frequency is not changed, as the thickness t of the vascular tissue $2_{ti}$ through which the acoustic wave is transmitted is thicker, a sound velocity v is increased, and an attenuation rate α is decreased. Also, when the embolism density is increased, the attenuation rate α is increased because of the increase in the dispersion source of the acoustic wave (guide wave) $\phi$ and the decrease in the elastic modulus of the vascular tissue $2_{ti}$.

Figure 23:
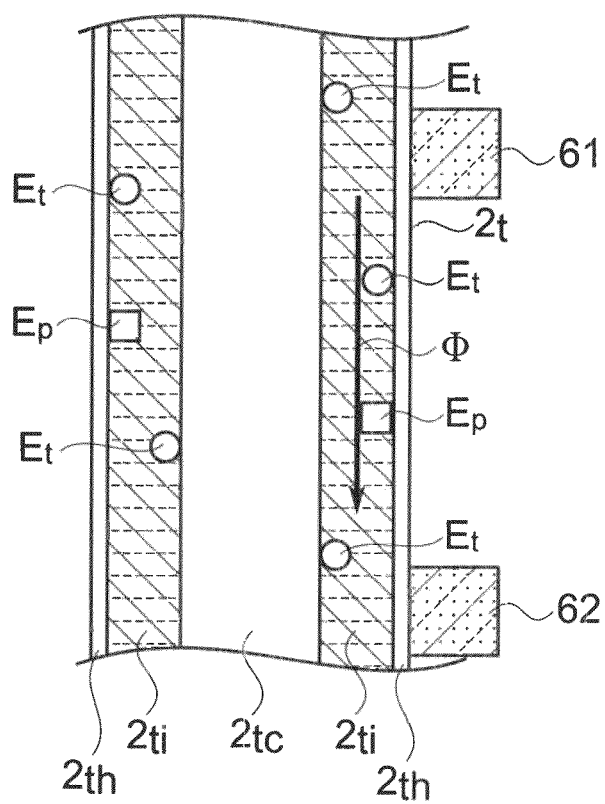
FIG. 23 is a schematic cross-sectional view illustrating a manner in which in the evaluation system of the botanical-integrity in vascular plant and the irrigating system according to the seventh embodiment, when the acoustic wave of the wavelength sufficiently longer than the thickness of the vascular tissue is entered from the surface of the main axis, the guide wave is generated in the vascular tissue and laterally propagated through the vascular tissue.

In the seventh embodiment of the present invention, as illustrated in FIG. 22(b) or FIG. 23, an acoustic vibrator 61 that generates the acoustic wave (guide wave) $\phi$ between 1 kHz and 1 MHz and an acoustic receiver 62 are attached to the main axis $2_t$, and the acoustic wave (guide wave) $\phi$ is entered from the acoustic vibrator 61 to the main axis $2_t$, and the acoustic wave (guide wave) $\phi$ propagated through the vascular tissue $2_{ti}$ is detected by the acoustic receiver 62. In addition, the seventh embodiment will be described below by focusing to the main axis $2_t$. However, the acoustic vibrator 61 and the acoustic receiver 62 are attached to at least any of the side axes $2_{b1}$, $2_{b2}$, $2_{b3}$, $2_{b4}$, - - - exemplified in FIG. 1, and the acoustic wave (guide wave) $\phi$ is entered from the acoustic vibrator 61 to at least any of the corresponding side axes $2_{b1}$, $2_{b2}$, $2_{b3}$, $2_{b4}$, - - - , and the acoustic wave (guide wave) $\phi$ propagated through the vascular tissue $2_{ti}$ from at least any of the corresponding side axes $2_{b1}$, $2_{b2}$, $2_{b3}$, $2_{b4}$, - - - may be detected by the acoustic receiver 62. As mentioned already, in the present Specification, in addition to the main axis $2_t$ and the side axes $2_{b1}$, $2_{b2}$, $2_{b3}$, $2_{b4}$, - - - , the components including the petiole (leaf stalk), the vein and the like are defined as the "axes". Thus, typically, the acoustic vibrator 61 and the acoustic receiver 62 are attached to the axis, and the acoustic wave (guide wave) $\phi$ is entered from the acoustic vibrator 61 to the axis. Then, the acoustic wave (guide wave) $\phi$ propagated through the vascular tissue $2_{ti}$ of the axis may be detected by the acoustic receiver 62.

Then, the sound velocity v is calculated from the arrival time of the acoustic wave $\phi$, which is transmitted to the acoustic receiver 62 from the acoustic vibrator 61, and the attenuation rate α is calculated from the magnitude of the acoustic wave $\phi$ at the position at which the acoustic receiver 62 is arranged. Then, the thickness t of the vascular tissue $2_{ti}$ is calculated from the sound velocity v, and from the thickness t of the vascular tissue $2_{ti}$, a corresponding reference attenuation rate $α_{ref}$ is calculated (the attenuation rate α when the embolism is not generated). The calculated reference attenuation rate $α_{ref}$ is compared with the attenuation rate a measured when water stress is received. Consequently, the relative embolism density is calculated.

Actually, in the case of the miniature tomato, as illustrated in FIG. 22(b), the acoustic vibrator (piezoelectric sounding body) 61 and the acoustic receiver (AE sensor) 62 are attached to the main axis $2_t$ (typically, the axis), and the sound velocity v and the attenuation rate α (the calculation from a ratio of an output voltage of the sensor to an input voltage of the sounding body) are measured, and after the measurement, the main axis $2_t$ is cut (disconnected) to observe the cross-section. Consequently, the thickness t of the vascular tissue $2_{ti}$ is calculated. The result is illustrated in FIG. 24. As illustrated in FIG. 24(a), in association with the increase in the thickness t of the vascular tissue $2_{ti}$, the sound velocity v is increased, and as illustrated in FIG. 24(b), in association with the increase in the thickness t of the vascular tissue $2_{ti}$, the attenuation rate α is decreased.

Next, FIG. 25 illustrates a comparison with the result of the miniature tomato that begins to be wilted by water stress. As illustrated in FIG. 25(a), in the manner of the change in the sound velocity v associated with the increase in the thickness t of the vascular tissue $2_{ti}$, a significant difference is not observed between the case without water stress indicated by open square (□) marks and the case with water stress indicated by x marks. On the other hand, as illustrated in FIG. 25(b), in the manner of the change in the attenuation rate α associated with the increase in the thickness t of the vascular tissue $2_{ti}$, the attenuation rates a measured with water stress indicated by the x marks are plotted high as compared with the attenuation rates a measured without water stress indicated by the open square (□) marks. In particular, in the thin region of the thickness t of the vascular tissue $2_{ti}$, the attenuation rate α is known to be increased by water stress. The increase of the attenuation rate α is ascribable to the increase of the embolism density of the vascular tissue $2_{ti}$ as mentioned above.

Figure 26:
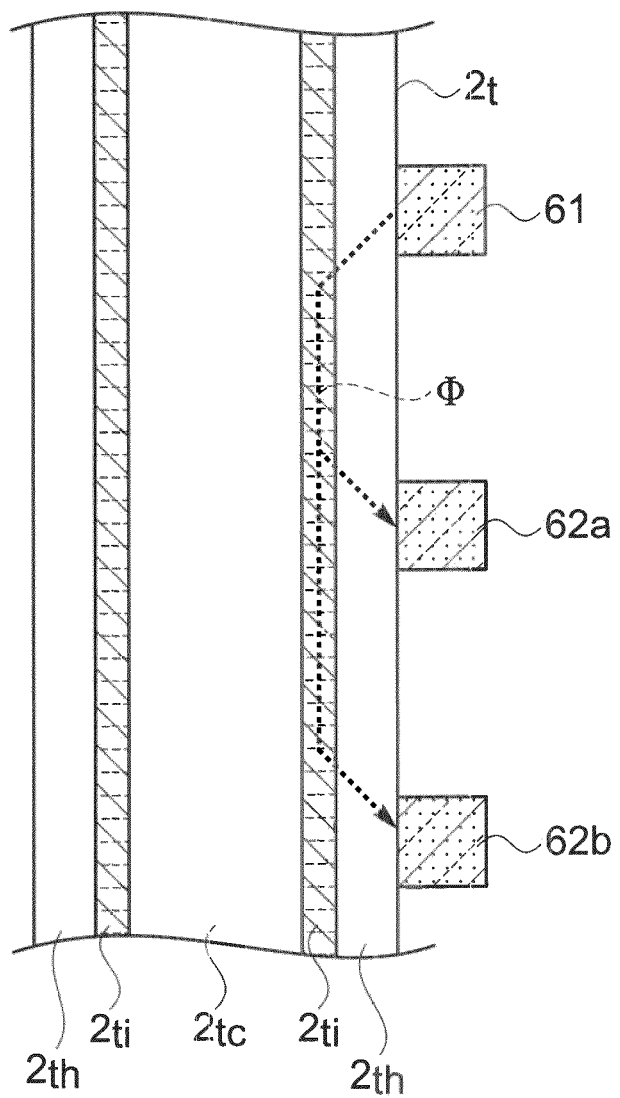
FIG. 26 is a schematic cross-sectional view describing a specific configuration for measuring the sound velocity and attenuation rate of the guide wave propagated through the vascular tissue, in the evaluation system of the botanical-integrity in vascular plant and the irrigating system according to the seventh embodiment.

In order to measure the sound velocity v and the attenuation rate α of the guide wave φ propagated through the vascular tissue $2_{ti}$, specifically, as illustrated in FIG. 26, a plurality of acoustic receivers, or two acoustic receivers (more generically, two or more acoustic receivers) of first acoustic receivers 62a and second acoustic receivers 62b are placed on the main axis $2_t$, and one acoustic vibrator 61 is placed on the main axis $2_t$ to which the first acoustic receiver 62a and the second acoustic receiver 62b are attached. The fixing methodology is equal to the case of the first acoustic receiver 62a and the second acoustic receiver 62b. The first acoustic receiver 62a, the second acoustic receiver 62b and the acoustic vibrator 61 are all placed on the same axis.

A burst acoustic wave of a frequency between 1 kHz and 1 MHz is entered from the acoustic vibrator 61 to the main axis $2_t$. The acoustic wave is transmitted as the guide wave φ through the vascular tissue $2_{ti}$ of the main axis $2_t$. The guide wave φ is detected at two points by the first acoustic receiver 62a and the second acoustic receiver 62b. A frequency of the acoustic vibrator 61 is defined such that a wavelength calculated from the sound velocity v of the guide wave φ is longer than the thickness t of the vascular tissue $2_{ti}$ and shorter than the diameter R of the main axis, because the guide wave φ is not generated when the wavelength of the burst acoustic wave is excessively short. Reversely, when the wavelength of the burst acoustic wave is excessively long, the burst acoustic wave arrives at the first acoustic receiver 62a and the second acoustic receiver 62b, prior to the formation of the guide wave φ. Thus, the wavelength is required to be shorter than a distance between a transmission and a reception (a distance between the acoustic vibrator 61 and the acoustic receiver 62a closer to the acoustic vibrator 61). In the light of above discussion, the wavelength of the burst acoustic wave is set to be between 0.1 and 100 mm, and the wavelength of the burst acoustic wave is desired to be between 1 and 20 mm. Also, the frequency in a wide band is used, and for the frequency received by the first acoustic receiver 62a and the second acoustic receiver 62b, only the frequency satisfying a specific condition may be filtered by a band pass filter.

A magnitude $I_0$ of the guide wave φ at the measurement point of the first acoustic receiver 62a allocated at the side closer to the acoustic vibrator 61 in FIG. 26, a magnitude $I_1$ of the guide wave φ at the measurement point of the second acoustic receiver 62b allocated at the side farther from the acoustic vibrator 61, a distance Δd between the measurement points of the first acoustic receiver 62a and the second acoustic receiver 62b, and an arrival time difference Δt of the guide wave φ between the measurement points of the first acoustic receiver 62a and the second acoustic receiver 62b are used to calculate the sound velocity v and the attenuation rate α of the guide wave φ propagated through the vascular tissue $2_{ti}$.

$$v = \Delta d / \Delta t \quad (4)$$

$$\alpha = \ln(R)/\Delta d \quad (5)$$

$$R = I_0/I_1 \quad (6)$$

The arrival time difference Δt of the guide wave φ is calculated from a startup time of the guide wave φ and a particular peak position. The magnitude $I_0$ of the guide wave φ at the measurement point of the first acoustic receiver 62a and the magnitude $I_1$ of the guide wave φ at the measurement point of the second acoustic receiver 62b use the particular peak magnitude.

Figure 27:
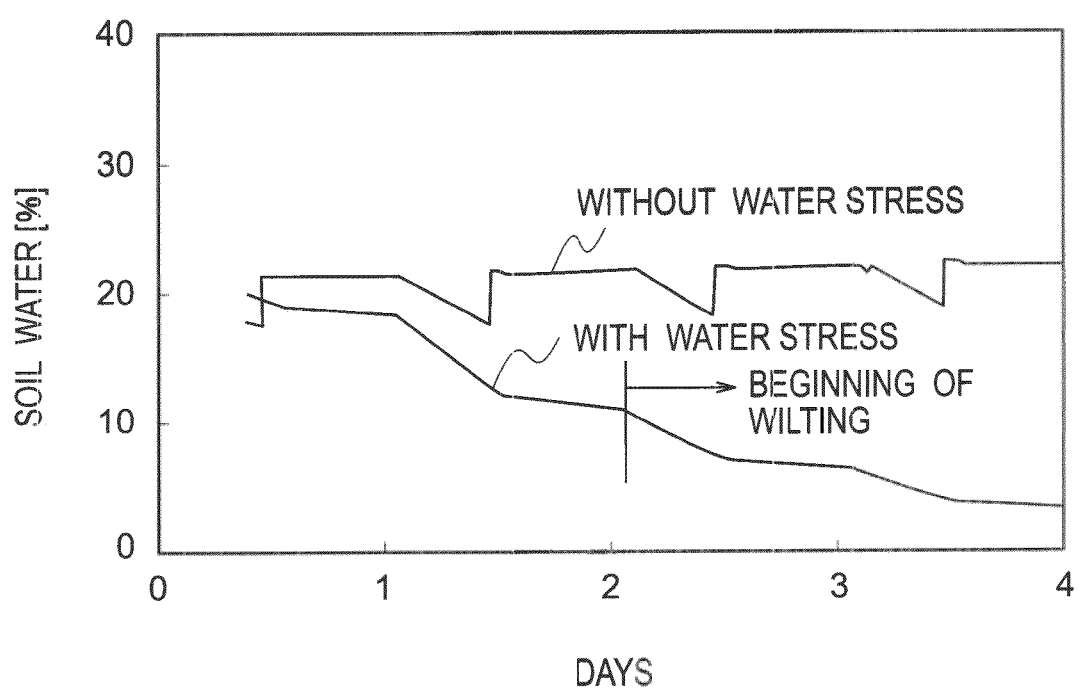
FIG. 27 is a view illustrating the variation per day of the soil water, while it is compared between the case without water stress and the case with water stress, when the vascular plant is assigned as the miniature tomato, in the evaluation system of the botanical-integrity in vascular plant and the irrigating system according to the seventh embodiment.

FIG. 27 illustrates a comparison between a case that the irrigation is sufficiently executed and the soil water is about 20% and constant (the absence of water stress) and a case that, since the irrigation is stopped and the soil water is reduced, the miniature tomato begins to be wilted (the presence of water stress), when the vascular plant of the measurement target is assumed to be the miniature tomato. In the comparison in FIG. 27, the other factors such as the temperature, the humidity, the solar irradiation, the fertilization, the soil component and the like are set to be equal between both of the cases, respectively. Thus, in the case with water stress, the decrease in the soil water results in the inevitable increase in the embolism density.

With regard to the miniature tomato compared in FIG. 27, as illustrated in FIG. 26, a plurality of acoustic receivers, or two acoustic receivers (more generically, two or more acoustic receivers) of first acoustic receiver (acceleration sensor) 62a and second acoustic receiver (acceleration sensor) 62b are placed on the main axis $2_t$, and one acoustic vibrator (piezoelectric sounding body) 61 is placed on the axis $2_t$ to which the first acoustic receiver 62a and the second acoustic receiver 62b are attached, and the acoustic wave (guide wave) φ generated by the acoustic vibrator 61 is received by the first acoustic receiver (acceleration sensor) 62a and the second acoustic receiver (acceleration sensor) 62b, and the acoustic waves (guide waves) φ whose transmission distances are different are received. Then, FIGS. 28 and 29 illustrate the results in which the sound velocity v and the attenuation rate α are calculated from the time difference and magnitude ratio of the first peak (or, as illustrated in FIG. 30, the acoustic vibrator (piezoelectric sounding body) 61 and the acoustic receiver (acceleration sensor) 62 are placed on the longitudinal direction of the axis, respectively, and the acoustic wave (guide wave) φ generated by the acoustic vibrator 61 is received by the acoustic receiver 62, and the position of the acoustic receiver 62 is shifted to receive the acoustic wave (guide wave) φ that is different in transmission distance. Then, the sound velocity v and the attenuation rate α may be calculated from the time difference and magnitude ratio of the first peak.)

Although FIG. 28 illustrates the case without water stress, the sound velocity v and the attenuation rate α are not substantially changed. On the other hand, FIG. 29 illustrates the case with water stress. When the decrease in the soil water involves the increase in the embolism density, it is known that, although the sound velocity v is not changed as illustrated in FIG. 29(a), the attenuation rate α is increased as illustrated in FIG. 29(b). The attenuation rate α in FIG. 29(b) is normalized under assumption that the attenuation rate α is one in a state in which water stress is absent at the time of the measurement start, and the increase rate of the attenuation rate α after the time of the measurement start indicates the relative embolism.

As illustrated in FIGS. 24 and 25, the sound velocity v of the guide wave φ propagated through the vascular tissue $2_{ti}$ and the attenuation rate a of the guide wave φ have the relation with the thickness t of the vascular tissue $2_{ti}$. Therefore, when the guide wave φ propagates through the vascular tissue $2_{ti}$ having a thickness t, and in the case that the irrigation is sufficiently carried out, a relationship between the sound velocity v of the guide wave φ and the thickness t of the vascular tissue $2_{ti}$ and a relationship between the attenuation rate α of the guide wave φ and the thickness t of the vascular tissue $2_{ti}$ are both examined in advance.

At first, the thickness t of the vascular tissue $2_{ti}$ is calculated from the sound velocity v determined from the detected guide wave φ. Next, from the thickness t of the vascular tissue $2_{ti}$ calculated from the sound velocity v, the attenuation rate α when the irrigation is sufficient is determined, and the determined attenuation rate α is defined as a reference attenuation rate $α_{ref}$. An attenuation rate ratio Ra of the subject attenuation rate α determined from the detected guide wave φ is defined against the reference attenuation rate $α_{ref}$ as calculated from Eq. (7).

$$R_a = α/α_{ref} \quad (7)$$

When the embolism density in the vascular tissue $2_{ti}$ increases, the dispersion of the guide wave φ propagated through the vascular tissue $2_{ti}$ is made greater, which increases the attenuation rate α of the guide wave φ and the attenuation rate ration $R_a$ increases. When the relationship between the increase in the attenuation rate ration $R_a$ and the embolism density is examined in advance, the embolism density can be determined from the attenuation rate ratio $R_a$.

When the embolism density in the vascular tissue $2_{ti}$ increases, water quantity of the xylem decreases, which leads to the drop in a density ρ. On the other hand, as water stress (the negative pressure of water in the xylem) also increases, elastic modulus E also decreases. Usually, because the sound velocity v of the longitudinal wave of the guide wave φ is proportional to $(E/ρ)^{1/2}$, and the density ρ and the elastic modulus E decrease together, while the sound velocity v is not varied, only the attenuation rate α increases.

The evaluation of the botanical-integrity of the vascular plant cannot determine the critical embolism density (because when the environmental factors vary, even under the same embolism density, there are a case that embolism density arrives to the critical state and a case that embolism density cannot arrive to the critical state). However, the measurement of the guide wave φ propagated through the vascular tissue $2_{ti}$ is completed in a short time (between one second and one minute). Thus, the damage is never given to the axis. For this reason, the combination with at least one of the methods explained in the first to sixth embodiments enables the effective utilization. For example, when there is no great variation in the environment, one of the methods of the first to sixth embodiments is used to measure the embolism density. Then, when the embolism density is greatly increased, or when the great variation is generated in the environment, one of the methods of the first to sixth embodiments is used to carry out the measurement. Then, whether or not the measured embolism density arrives at the critical embolism density is checked to evaluate the botanical-integrity in vascular plant.

Figure 34:
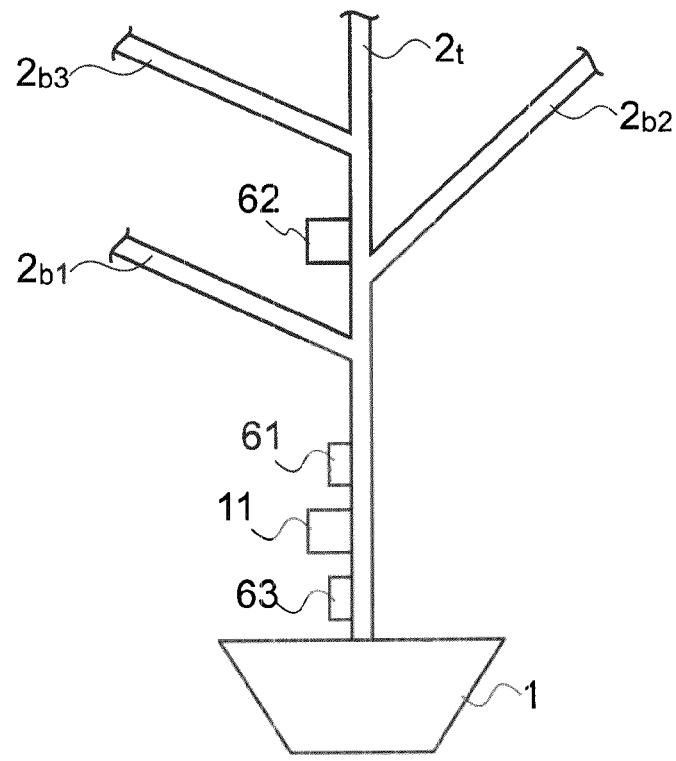
FIG. 34 is a schematic view describing the rough configuration of the evaluation system of the botanical-integrity in vascular plant and the irrigating system according to the seventh and ninth embodiments of the present invention.

When herbaceous plants are exposed to the severe water stress, the same behavior as woody plants, which will be described later, is manifested, and the sound velocity begins to be made high in the herbaceous plants with the water stress. As illustrated in FIG. 34, the AE sensor 11 is attached to the main axis (stalk) $2_t$ of the miniature tomato, which is cultivated by extremely reducing the irrigation quantity, by using the method of the sixth embodiment, as illustrated in FIG. 34. Then, the rate of change of AE occurrence frequency $R_{AE}$ is calculated from the AE measurements before and after the irrigating operation. Moreover, as illustrated in FIG. 34, the sounding body (acoustic vibrator) 61 is also attached to the main axis (stalk) $2_t$, and the burst acoustic wave is periodically generated, and the acoustic wave is received by the AE sensor 11.

Figure 35:
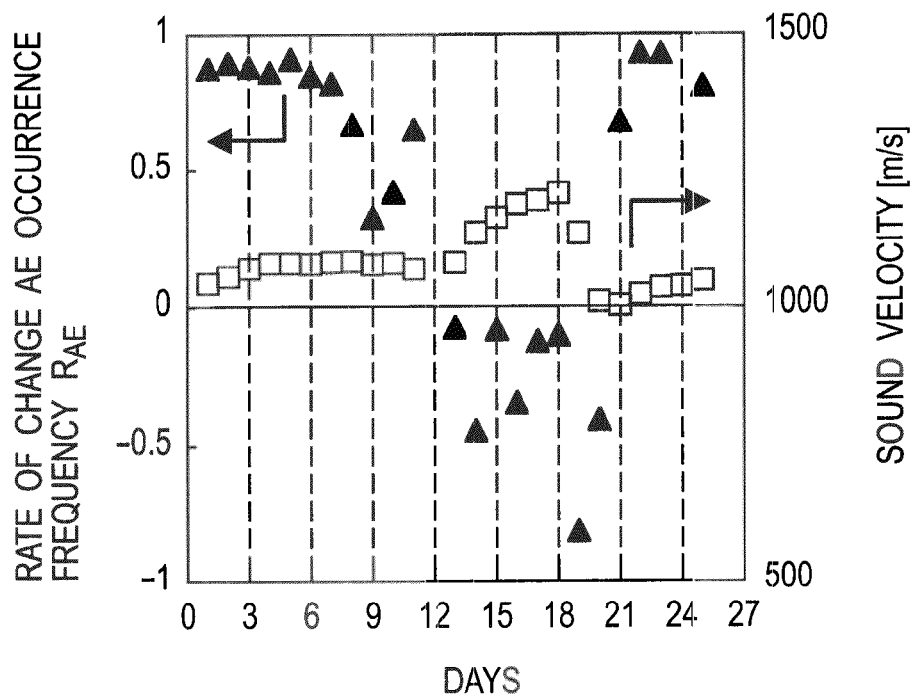
FIG. 35 is a view illustrating a result in which in the evaluation system of the botanical-integrity in vascular plant and the irrigating system according to the seventh embodiment of the present invention, the guide wave propagated through a vascular bundle at a frequency of 130 kH is extracted from the acoustic wave received by the AE sensor through the use of a wavelet analysis, and the variation per day of the sound velocity and the AE occurrence frequency change rate are measured.

FIG. 35 illustrates the result in which the guide wave propagated through the vascular bundle at frequency of 130 kHz (and the wavelength between 7.7 and 9.5 mm) is extracted from the acoustic wave received by the AE sensor 11 through the use of the wavelet analysis and then the variation per day of the sound velocity and the rate of change of AE occurrence frequency $R_{AE}$ are measured. The irrigation quantity is limited until the eighteenth day, and the sufficient irrigation is carried out from the nineteenth day. From the behavior of the rate of change of AE occurrence frequency $R_{AE}$ indicated by solid triangles (▲), the embolism density exceeds the critical embolism density from the thirteenth day, and the wilting can be visually observed all day from the fourteenth day. As indicated by open squares (□) in FIG. 35, when the severe water stress is occurred on the thirteenth day, the sound velocity of the guide wave propagated through the vascular bundle is made high, and when the irrigation is sufficiently carried out on the nineteenth day, the sound velocity again returns to the original value. Although the usual crops are never cultivated under such severe water stress, when the minimal required irrigation that enables the life support is desired to be carried out in the cultivation in arid region and the like, monitoring the sound velocity of the guide wave propagated through vascular bundle can evaluate the botanical-integrity in vascular plant and carry out the irrigating operation at a level at which the plant is not blighted.

In the case of the woody plants (lignified stems and stalks), the behaviors of the embolism density, the sound velocity and the attenuation rate greatly differ from those of the herbaceous plants. At first, the main axis (stalk) $2_t$ of the lignified woody plants is divided into a sapwood having the vascular tissue and a heartwood almost implemented by dead cells, and the embolism is generated in the sapwoods, the dead cells in the heartwoods and the vessel tissues. Then, it is known that the increase in the embolism density implies the drop in a moisture content, and that with the drop in the moisture content, the sound velocity of the wood increases and the attenuation rate decreases. The difference in the behavior from the herbaceous plant lies in the fact that, although in the herbaceous plant, the turgor pressure of the cell has influence on the rigidity of the plant body, in the case of the woody plant, the rigidity of the plant body is controlled by the rigidity of the xylem fiber. However, differently from the dry of the wood, because the embolism is locally generated and grown, when the embolism density increases, the attenuation rate increases by the dispersion effect of the acoustic wave, and the increase of the attenuation rate is greater than the effect caused by the drop in the moisture content. Hence, when the embolism density increases, the attenuation rate increases.

As illustrated in FIG. 34, the sounding body (acoustic vibrator) 61 and the acoustic receiver (acceleration sensor) 62 are attached to the main axis (stalk) $2_t$ of the strawberry tree, and every six minutes, the burst acoustic wave is generated from the sounding body (acoustic vibrator) 62, and the guide wave propagated through the main axis (stalk) $2_t$ is measured by the acoustic receiver (acceleration sensor) 62. FIG. 36(a) illustrates the result in which the variation per day in the sound velocity is measured in the process for recovering water stress from the state where the severe water stress is given, when the guide wave propagated through the main axis (stalk) $2_t$ is measured as illustrated in FIG. 34. FIG. 36(b)

illustrates the result when the time-dependent change of the corresponding attenuation rate is measured. In the experiment illustrated in FIG. 36, an illumination is turned on at a cycle of twelve hours, and everyday, the irrigating operation is carried out one hour before the illumination is turned off (after eleven hours, after 35 hours and after 59 hours). The measured waveforms are averaged for each 30 minutes, and the guide wave of 100 kHz is extracted by the wavelet analysis, and the sound velocity and the attenuation rate are measured. The wavelength (between 6.5 and 7 mm) of the guide wave is sufficiently longer than the thickness (between 2 and 4 mm) of the sapwood having the vascular tissue and sufficiently shorter than the diameter (12 mm) of the main axis (stalk) $2_t$. Thus, the guide wave is propagated through the vascular tissue. At the beginning of the experiment, the strawberry tree is not irrigated. Hence the great embolism is generated. However, by the irrigating operation after eleven hours, the embolism density is greatly decreased, which involves the decreases in the sound velocity and the attenuation rate, as illustrated in FIG. 36. The decrease in the sound velocity in FIG. 36($a$) is caused by the decrease in the moisture content. Consequently, it is possible to evaluate the relative embolism density.

On the other hand, the attenuation rate also decreases by the decrease in the dispersion effect of the acoustic wave caused by the embolism. After that, even if the irrigating operation is carried out after 35 hours and after 59 hours, since the embolism does not substantially exist around the vascular tissue, the sound velocity is not changed as illustrated in FIG. 36($a$). However, as illustrated in FIG. 36($b$), the attenuation rate is slightly increased after 35 hours and after 59 hours. This is because as the result of the decrease in the embolism of the heartwood, the difference of the acoustic impedance between the sapwood and the heartwood becomes small, which transmits the acoustic wave into the heartwood. For this reason, although the attenuation rate indicates the minimum value, the minimum value can be also defined as "the critical embolism density of the sapwood".

For the sake of the occurrence of the guide wave φ propagated through the vascular bundle, the vascular plant having the annularly-grown vascular tissue $2_{ti}$ is required, the annularly-grown vascular tissue $2_{ti}$ largely differs from the adjacent tissue with regard to the acoustic impedance (the product of the density ρ and the sound velocity v). Also, the frequency of the transmitted/received guide wave φ must be designed such that the wavelength is longer than the thickness t of the vascular tissue $2_{ti}$.

For example, in the experiment results illustrated in FIGS. 28 and 29, the guide wave φ of the frequency 80 kHz is extracted from the measured transmission/reception waveform through the use of the wavelet analysis. Their wavelengths are between 13 mm and 15 mm. The thickness t of the vascular tissue $2_{ti}$ of the miniature tomato used in the experiment is 1 mm or less, and the thickness t of the vascular tissue $2_{ti}$ sufficiently satisfies the condition that enables the occurrence of the guide wave φ.

In a measurement without water stress, the attenuation rate a may be measured to define "a standard embolism". However, when the measurement target grows, the thickness t of the vascular tissue $2_{ti}$ is changed, thereby changing the reference attenuation rate $α_{ref}$ is also changed. Therefore, when the thickness t of the vascular tissue $2_{ti}$ changes with the growth of target plant, for the measurement without water stress, the relationship between the sound velocity v and the thickness t of the vascular tissue $2_{ti}$ and the relationship between the attenuation rate α and the thickness t of the vascular tissue $2_{ti}$ are examined in advance. Then, the reference attenuation rate may be calculated from the sound velocity.

Figure 31:
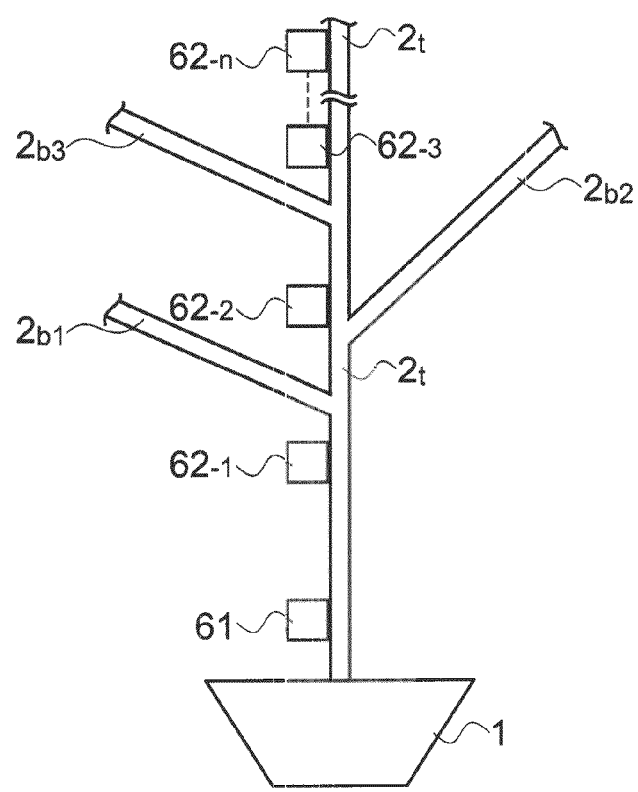
FIG. 31 is a schematic view describing a fact in which in the seventh embodiment of the present invention, in order to measure the sound velocity and attenuation rate of the guide wave propagated through the vascular tissue, a plurality of acoustic receivers are placed at the same time, and the respective guide waves are detected.

In the seventh embodiment of the present invention, in order to measure the sound velocity v and the attenuation rate α of the wave propagated through the vascular tissue $2_{ti}$, as illustrated in FIG. 30, a single acoustic receiver 62 may be used to detect the guide wave φ at the plurality of points by changing the placement position. Or, as illustrated in FIG. 31, a plurality of acoustic receivers $62_{-1}$, $62_{-2}$, $62_{-3}$, - - -, $62_{-n}$ (n is an integer of two or more) may be simultaneously placed to detect the guide waves φ and measure the sound velocities v and the attenuation rates α, respectively. In FIGS. 30 and 31, as illustrated in FIGS. 5 and 6, when the film electret microphones are used as the acoustic receivers 62, $62_{-1}$, $62_{-2}$, $62_{-3}$, - - -, $62_{-n}$ and the acoustic vibrator 61, the acoustic wave can be efficiently transmitted to and received from the medium of the low acoustic impedance such as the vascular plant, because the acoustic impedances of the pressure reception surface (silicon resin surface) and the gap portion are low. The film electret sensor has the lower acoustic impedance, because the contact rigidity of the micro gap portion is low, and the transmission/reception efficiency to/from the vascular plant is high. Hence, the transmission/reception sensibility of the guide wave φ propagated through the axis $2_t$ can be largely improved.

Figure 32:
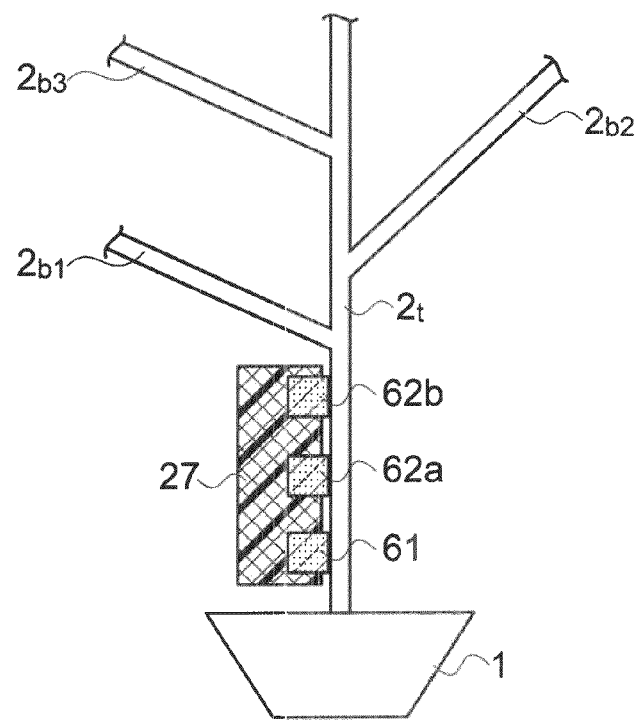
FIG. 32 is a schematic view describing a fact in which in the seventh embodiment of the present invention, in order to measure the sound velocity and attenuation rate of the guide wave propagated through the vascular tissue, an acoustic vibrator and the plurality of acoustic receivers are all integrated inside one measurement device, and the guide wave is detected.
Figure 33:
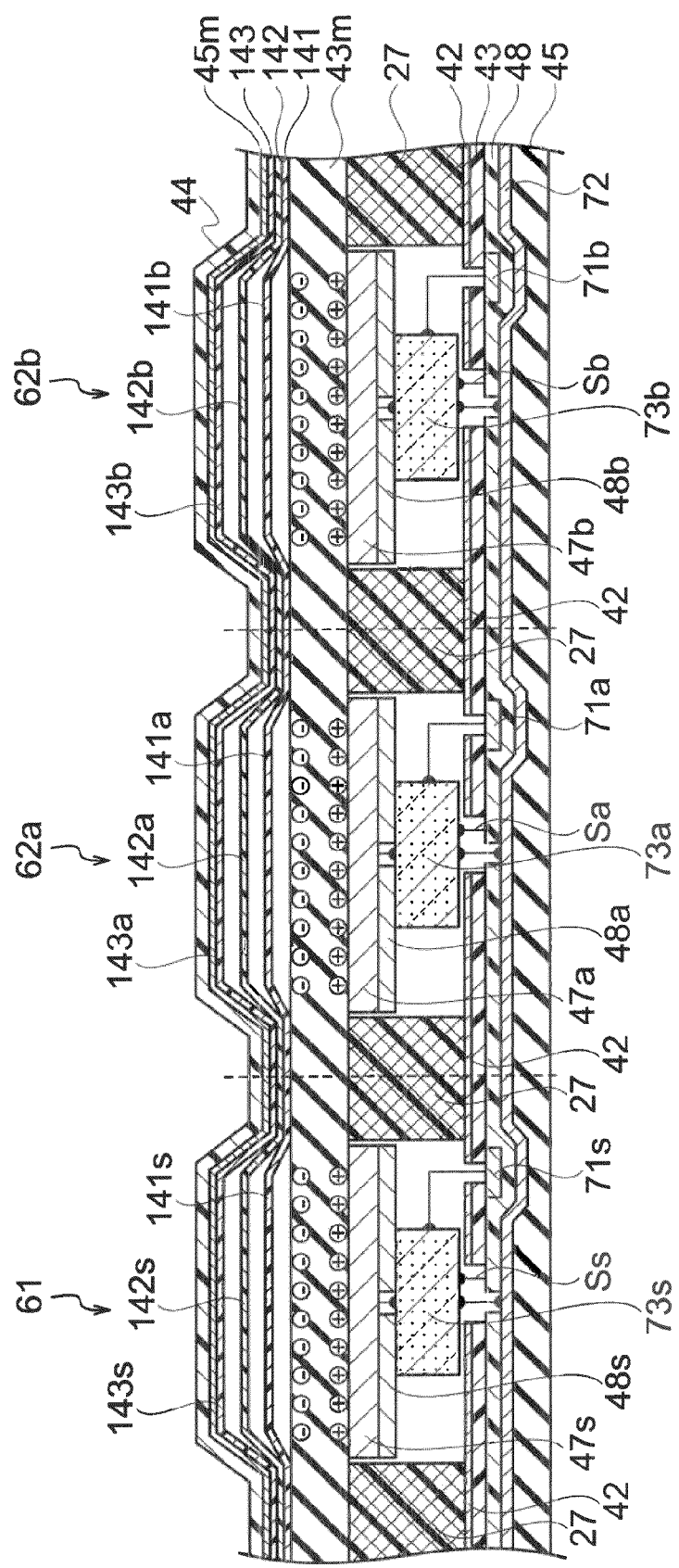
FIG. 33 is a schematic cross-sectional view describing the detailed structure of the film ECM array, which is preferable for the detecting method of the guide wave illustrated in FIG. 32.

Or, as illustrated in FIG. 32, the first acoustic receiver 62$a$, the second acoustic receiver 62$b$ and the acoustic vibrator 61 may be all integrated in one measurement device (27, 61, 62$a$ and 62$b$), and the measurement may be carried out. In order to integrate all of the first acoustic receiver 62$a$, the second acoustic receiver 62$b$ and the acoustic vibrator 61 into one measurement unit, the structure of the film ECM array illustrated in FIG. 33 is preferable. When focusing to the first acoustic receiver 62$a$ on the center in FIG. 33, and the cross-sectional structure is described, in the first acoustic receiver 62$a$ implementing a part of the film ECM array according to the seventh embodiment of the present invention, between a gap insulation film 141$a$ of a first layer and the polymer film 43$m$, the first spacer (whose illustration is omitted) formed of particles of insulator, each having the particle diameter between 10 nm and 40 μm, is inserted, and between the gap insulation film 141$a$ of the first layer and a gap insulation film 142$a$ of a second layer, the second spacer (whose illustration is omitted) formed of particles of insulator, each having the particle diameter between 10 nm and 40 μm, is inserted, and between the gap insulation film 142$a$ of the second layer and a gap insulation film 143$a$ of the third layer, the third spacer (whose illustration is omitted) formed of particles of insulator, each having the particle diameter between 10 nm and 40 μm, is inserted. Consequently, the interval of the gap defined between the vibration electrode film 45$m$ and the polymer film 43$m$ is controlled. The gap insulation film 143$a$ of the third layer and the vibration electrode film 45$m$ are closely adhered, and the gap insulation film 143$a$ of the third layer exhibits the function equivalent to the vibration electrode insulation film of the film ECM array. In this way, between the vibration electrode film 45$m$ and the polymer film 43$m$, the plurality of gap insulation films 141$a$, 142$a$, 143$a$, - - - are stacked and inserted through the spacers (whose illustrations are omitted) formed of particles of insulator, each having the particle diameter between 10 nm and 40 μm. Consequently, between the gap insulation film 143$a$ of the third layer and the gap insulation film 142$a$ of the second layer, between the gap insulation film 142$a$ of the second layer and the gap insulation film 141$a$ of the first layer, and between the gap insulation film 141$a$ of the first layer and the polymer film 43$m$, the micro gaps are defined, respectively, which control the respective intervals in the first acoustic receiver 62.

When the particle diameter is set to 100 µm or less, each of the particles serving as the first to third spacers, each of the effective surface a roughness $Ra_{eff}$ of the surfaces of the respective micro gaps can be less than or equal to ¹/₁₀ of the gap width provided in the element space, which is defined for each element, between the bottom surface of the gap insulation film 143a of the third layer and the top surface of the polymer film 43m (the effective surface roughness $Ra_{eff}$ includes the bending under loading condition). However, in order to achieve the film ECM array that is flexible and high in shape free degree, the particle diameter of between 10 nm and 10 µm is preferable, each of the particles serving as the first to third spacers, because the entire thickness is further thin. Moreover, as a matter of course, in the range between 10 nm and 5 µm, the particle diameter closer to 10 nm is desirable. Each of the back electrode films 47s, 47a, 47b, - - - and the polymer film 43m may be metallurgically joined, or may be adhered with the adhesive agent and the like, or may be merely brought into contact with each other by the mechanical pressure.

The vibration film protection film 44 for protecting the vibration electrode film 45m is formed on the vibration electrode film 45m. Since the vibration film protection film 44 serves as the matching layer for increasing the adhesive property to the vascular plant and the matching property of the acoustic impedance, the vibration film protection film 44 is desired to be the flexible resin layer. Its thickness may be changed and employed on the basis of the property, in the range between about 10 and 100 µm. In FIG. 33, for example, it is possible to use a silicon resin film having the thickness between 50 µm and 100 µm. The flexible base 27 made of insulation material is stuck on the bottom surface of the polymer film 43m. Correspondingly to the array of the acoustic vibrator 61, the first acoustic receiver 62a and the second acoustic receiver 62b, hollow portions are sequentially made in the flexible base 27, and amplifiers (buffer amplifiers for reading the charges) 73s, 73a and 73b are stored in the hollow portions, respectively. The amplifiers 73s, 73a and 73b are placed (mounted) on circuit substrates 48s, 48a and 48b joined (placed) on the bottom surfaces of the back electrode films 47s, 47a, 47b - - - of the acoustic vibrator 61, the first acoustic receiver 62a and the second acoustic receiver 62b, respectively. The through holes (vias) are made in each of the circuit substrates 48s, 48a and 48b. Then, through the respective through holes (vias), the amplifiers 73s, 73a and 73b are electrically connected through the connecting means such as solder balls fused on the back electrode films 47s, 47a, 47b - - - and the like, to the back electrode films 47s, 47a, 47b - - - , independently of each other.

The conductive (metallic) shield conductor film 42 is formed on the bottom surface of the flexible base 27, and a shield conductor protection film 43 is formed on the bottom surface of the shield conductor film 42. Through the shield conductor protection film 43, signal lines 71s, 71a and 71b run in a direction vertical to a paper surface, and the signal lines 71s, 71a and 71b are connected to the amplifiers 73s, 73a and 73b, respectively. So as to cover the signal lines 71s, 71a and 71b, an inter-layer insulation film 48 is formed on the bottom surface of the shield conductor protection film 43. Through the inter-layer insulation film 48, a reset signal wiring 72 is laid orthogonally to the amplifiers 73s, 73a and 73b. On the cross-sectional view in FIG. 33, although the illustration is omitted, a vertical selection signal wiring runs orthogonally to the amplifiers 73s, 73a and 73b, on the interior of the paper surface. So as to cover the reset signal wiring 72 and the vertical selection signal wiring whose illustration is omitted, a passivation film 45 is formed on the bottom surface of the inter-layer insulation film 48.

With the use of the film ECM array illustrated in FIG. 33, in the transmission/reception of the guide wave φ propagated through the axis $2_r$, the guide wave φ can be generated from the acoustic vibrator 61, and the guide wave φ propagated through the first acoustic receiver 62a and the second acoustic receiver 62b can be detected. To do so, by arraying the first acoustic receiver 62a, the second acoustic receiver 62b and the acoustic vibrator 61 at a micro interval, it is possible to measure the attenuation rate α of the guide wave φ in the short time. Then, the use of the average value between them leads to the improvement of the measurement precision of the attenuation rate α.

The film ECM array illustrated in FIG. 33 can be attached to the axis $2_t$ by using the method illustrated in FIGS. 2 and 3. However, similarly to the configuration illustrated in FIG. 14, it is desired to employ the configuration in which the flexible base 27 is wound around the axis $2_t$. Actually, because the shape of the axis is not smooth cylinder as illustrated in FIGS. 2 and 3, and there are the ups and the downs, the flexibility of the film ECM array can be utilized to improve adhesion degree to the axis having the ups and the downs.

Also, by using the flexibility of the film ECM array and the high reception sensibility, the film ECM array can be used in the manner in which the leaf 3 is sandwiched as illustrated in FIGS. 16 and 17. In the case of the film ECM array, the film ECM array can be closely adhered to the leaf 3, because the film ECM array is flexibly deformed. Thus, the guide wave j propagated through the vein $3_r$ can be efficiently transmitted and received.

Eighth Embodiment

Figure 37:
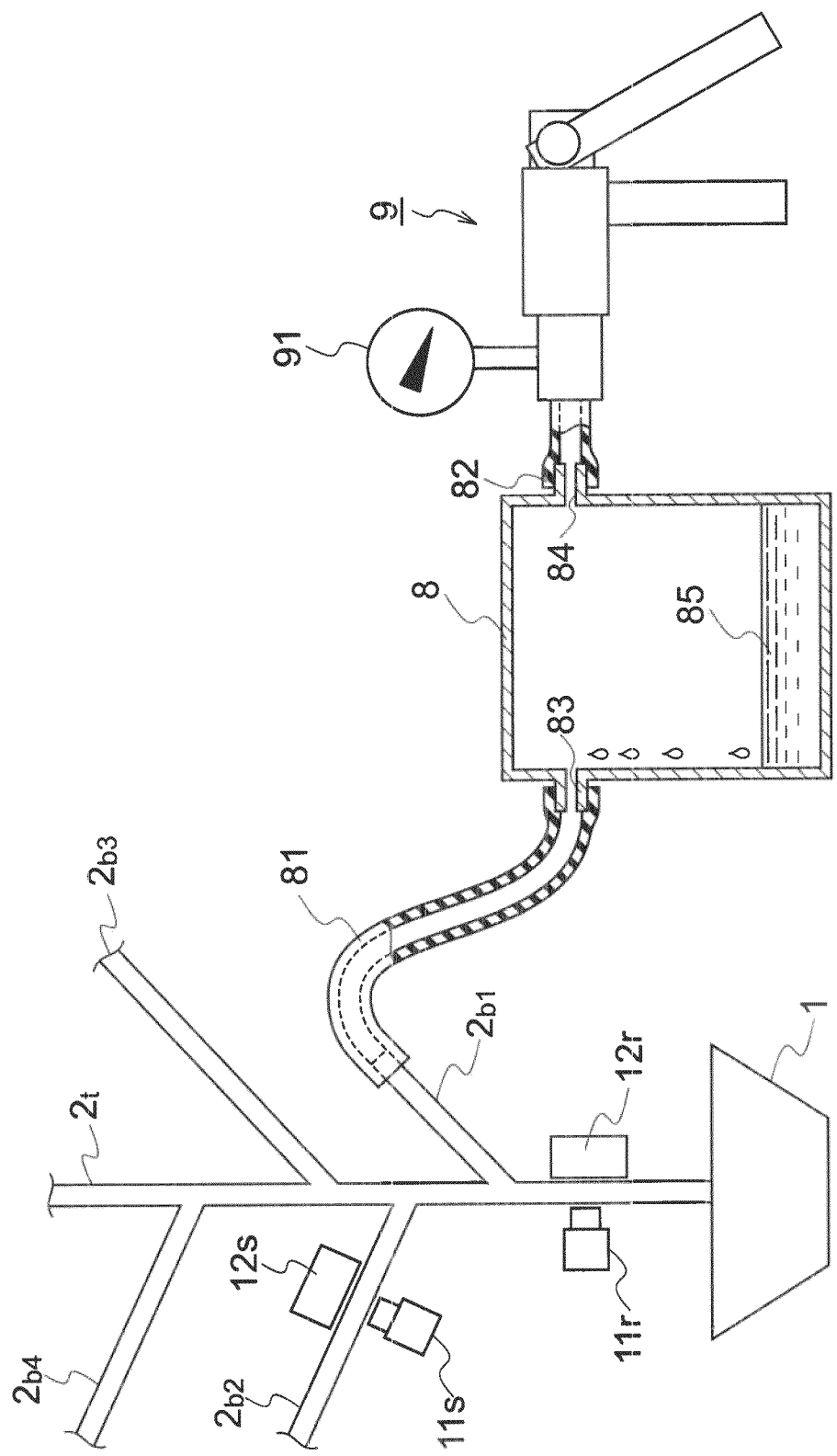
FIG. 37 is a schematic view describing the rough configuration of the evaluation system of the botanical-integrity in vascular plant and the irrigating system, according to an eighth embodiment of the present invention.

As illustrated in FIG. 37, in an evaluation method of degree of botanical-integrity in vascular plant and an irrigating system according to the eighth embodiment, the side axis $2_{b2}$ of the vascular plant is cut (disconnected) and disconnected, and a vacuum pump 9 is connected to the end of the disconnected side axis $2_{b2}$, and a water 85 is forcibly exhausted from the vascular plant, by a pressure difference, and the negative pressure of the xylem increases. The vacuum pump 9 may be a simple apparatus of a manual type. The vacuum pump 9 and the vascular plant can be connected by using a vacuum system, which includes a first vacuum tube 81, a vacuum box 8 and a second vacuum tube 82, in the irrigating system according to the eighth embodiment, as exemplified in FIG. 37. The first vacuum tube 81 connects the end of the side axis $2_{b2}$ of the disconnected vascular plant and a sucking pipe 83 in the vacuum box 8, and the second vacuum tube 82 connects an exhausting pipe 84 of the vacuum box 8 and a vacuum pump 93. The connection between the first vacuum tube 81 and the end of the side axis $2_{b2}$ of the disconnected vascular plant may be fixed by inserting the first vacuum tube 81 to the end of the side axis $2_{b2}$ of the disconnected vascular plant and using a fixing means such as a hose clamp (whose illustration is omitted) and the like. Or, it is carried out such that the tip of the first vacuum tube 81 is shaped as a pipe or injection needle having an acute section and stuck to the end of the side axis $2_{b2}$ of the vascular plant.

As the evaluation method of degree of botanical-integrity in vascular plant according to the eighth embodiment, at first, one or more elastic wave reception sensors are attached to the axis of the vascular plant. For example, in the irrigating system according to the eighth embodiment illustrated in FIG. 37, an elastic wave reception sensor 11r is attached through a rubber sheet 12r to the main axis $2_t$ of the vascular plant, and an elastic wave reception sensor 11s is attached through a rubber sheet 12s to the side axis $2_{b2}$ of the vascular plant. The elastic wave reception sensors 11r, 11s are used to measure the occurrence frequency $AE_{low}$ of the elastic wave emitted from the vascular plant, for a period between one minute and one hour. After that, while it is monitored by a pressure gauge 91, the vacuum pump 9 is used to reduce the pressure in the inside of the vacuum box 8 to 90 kPa or less. After that, the elastic wave reception sensors 11r, 11s are used to measure the occurrence frequency $AE_{high}$ of the elastic wave emitted from the vascular plant, for a period between one minute and one hour. Then, the rate of change of AE occurrence frequency $R_{AE}$ is calculated by using Eq. (2). After the calculation of the rate of change of AE occurrence frequency $R_{AE}$, the calculated rate of change of AE occurrence frequency $R_{AE}$ is used as the index, and the botanical-integrity of the vascular plant may be evaluated to determine the irrigation timing and irrigation quantity to the vascular plant.

In the irrigating system according to the eighth embodiment illustrated in FIG. 37, when leakage is generated from a sealing portion between the first vacuum tube 81 and the end of the side axis $2_{b2}$ of the vascular plant or a sealing portion between the needle and the end of the side axis $2_{b2}$ of the vascular plant, the occurrence frequency $AE_{high}$ of the elastic wave emitted from the vascular plant is measured while the vacuum pump 9 is operated in order to keep a compressed state. In this case, the acoustic wave is generated from the leakage portion. Thus, the elastic wave reception sensors 11r, 11s are desired to carry out the measurement while avoiding the frequencies of the acoustic noises from the leakage. The frequencies of the acoustic noises from the leakage depend on the pressure. However, most of the acoustic noises is 40 kHz or less.

The irrigating system according to the eighth embodiment illustrated in FIG. 37 increases water stress of the entire vascular plant. Thus, the placement positions of the elastic wave reception sensors 11r, 11s may be arbitrary on the axis. However, when the elastic wave reception sensors 11r, 11s are placed at the positions closer to the connection portion to the first vacuum tube 81, the variation in water stress becomes faster. Thus, the measurement can be carried out in the shorter time. In that case, in order to avoid the noise caused by the leakage, the measurement is desired to be carried out at the high frequency of 40 kHz or more.

Ninth Embodiment

When the acoustic wave (guide wave) $\phi$ is propagated through the entire axis, such as the plurality of side axes $2_{b1}$, $2_{b2}$, $2_{b3}$, - - - branched from the main axis $2_t$, the sound velocity v and attenuation rate $\alpha$ of the acoustic wave (guide wave) $\phi$ exhibit the great correlation to a water potential $\phi$w. Thus, by measuring the sound velocity v and attenuation rate $\alpha$ of the acoustic wave when the acoustic wave (guide wave) $\phi$ is propagated through the entire axis, it is possible to measure water potential $\phi$w and consequently evaluate water state of the plant and evaluate the botanical-integrity in vascular plant.

(Evaluating Method of Water State of Herbaceous Plant)

When water potential $\phi$w of the herbaceous plant is measured, the turgor pressure of the cell has influence on the rigidity of the entire axis. Thus, the decrease in the turgor pressure leads to the decrease in the rigidity of the entire axis. As a result, the sound velocity v of the acoustic wave (guide wave) $\phi$ propagated through the entire axis decreases, and the attenuation rate $\alpha$ increases. For example, as illustrated in FIG. 34, by sufficiently irrigating the miniature tomato as the example of the vascular plant and acoustically measuring the acoustic wave (guide wave) $\phi$ propagated through the entire stem (axis) of the miniature tomato, it is possible to measure water potential $\phi$w of the miniature tomato.

That is, in the evaluation method of degree of botanical-integrity in vascular plant according to the ninth embodiment of the present invention, the main axis $2_t$ uprightly standing on the ground from the soil stored in the flower pot 1 and the vascular plant of the single axis branch having the plurality of side axes $2_{b1}$, $2_{b2}$, $2_{b3}$ - - - which are branched from the main axis $2_t$ are made symmetric, and the acoustic vibrator 61 placed on the root side of the main axis $2_t$ generates the burst acoustic wave for each six minutes, and the acoustic wave (guide wave) $\phi$ propagated through the entire main axis is measured by the acoustic receiver (acceleration sensor) 62 placed above the acoustic vibrator of the main axis $2_t$. Consequently, the acoustic wave (guide wave) $\phi$ propagated through the vascular tissue is measured, and water potential $\phi$w is measured from the relationship between the sound velocity v and attenuation rate $\alpha$ of the guide wave $\phi$ in each of the entire main axis and vascular tissue of the plant targeted for the measurement, which are examined in advance, and water potential $\phi$w. Also, a diameter gauge 63 placed on the root side of the main axis $2_t$ can be used to measure the diameter change in the stem (axis). The diameter gauge 63 can be implemented by a distortion gauge and the like.

Figure 38:
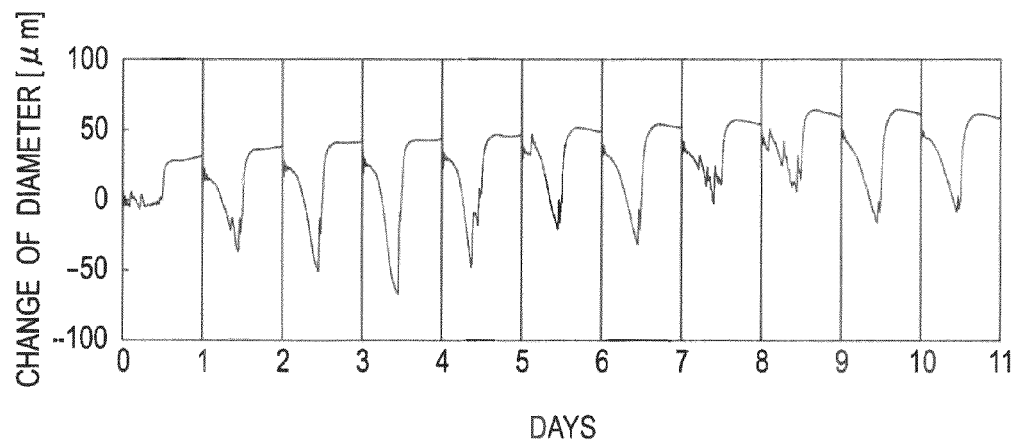
FIG. 38 is a view illustrating the variation per day in the axis diameter of the miniature tomato, in order to describe the evaluating method of water state of the plant, according to the ninth embodiment of the present invention.
Figure 39:
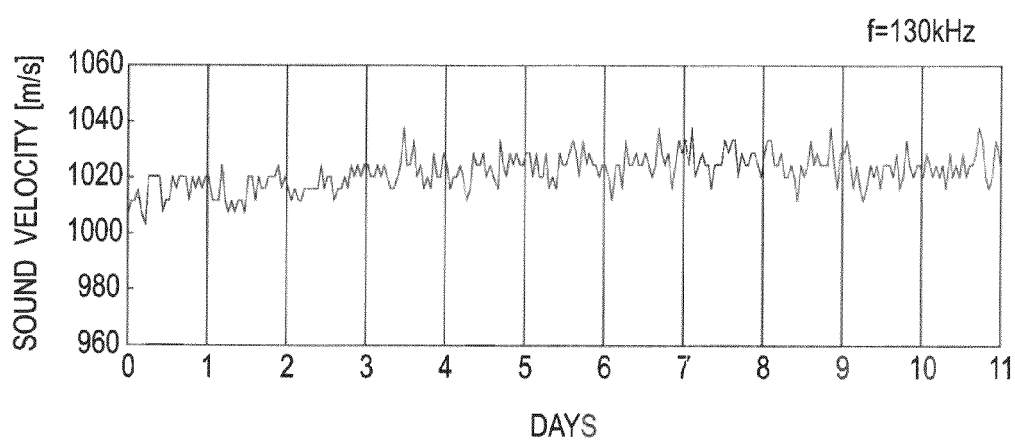
FIG. 39 is a view illustrating the variation per day in the sound velocity of the acoustic wave (guide wave) propagated through the whole of the axis of the miniature tomato, in order to describe the evaluating method of water state of the plant, according to the ninth embodiment of the present invention.

Although FIG. 38 illustrates the time-dependent change, the diameters (hereafter, referred to as "axis diameters") of the main axis $2_t$ and the side axes $2_{b1}$, $2_{b2}$, $2_{b3}$, - - - of the miniature tomato are contracted in the daytime everyday by the transpiration and recovered in the nighttime. The diameter change is proportional to the change in water potential. When the guide wave $\phi$ of 130 kHz is extracted from the measured transmission/reception waveform by the wavelet analysis, FIG. 39 illustrates the time-dependent change in the sound velocity v of the guide wave $\phi$. The wavelength of the extracted guide wave $\phi$ is between about 7.5 and 8 mm and sufficiently longer than the vascular bundle thickness (between 0.1 and 0.3 mm) and shorter than the axis diameter (14 mm). Thus, the guide wave $\phi$ is propagated through the vascular bundle. In this way, in the case of the guide wave $\phi$ propagated through the vascular bundle, as illustrated in FIG. 39, the sound velocity v does not receive the influence of the variation in water potential.

On the other hand, when the guide wave $\phi$ of 8 kHz is extracted from the measured waveform by the wavelet analysis, the time-dependent change in the sound velocity v is illustrated in FIG. 40(a), and the time-dependent change in the signal magnitude is illustrated in FIG. 40(b). From the illustrations, the sound velocity v and the signal magnitude are estimated to receive the influence of the change in water potential. The wavelength of the extracted guide wave $\phi$ is between about 42 and 47 mm and sufficiently longer than the vascular bundle thickness (between 0.1 and 0.3 mm) and the axis diameter (14 mm). Thus, the guide wave $\phi$ is propagated through the entire stem (axis). In the case of the guide wave $\phi$ of 8 kHz, as illustrated in FIG. 41(a), in association with the decrease in the axis diameter (water potential $\phi$w), the sound velocity v decreases. Then, as illustrated in FIG. 41(b), in association with the decrease in the axis diameter (water potential $\phi$w), the signal magnitude also decreases (the attenuation rate $\alpha$ increases). In this way, when the embolism does not exist substantially, FIG. 41(a) and FIG. 41(b) indicate that the sound velocity v and signal magnitude (attenuation rate) of the guide wave $\phi$ of 8 kHz has the correlation with the axis diameter change. FIG. 41(a) and FIG. 41(b)

indicate the result that the variation in water potential ϕw has influence on the turgor pressure of the cell. Consequently, the sound velocity v and peak magnitude (attenuation rate) of the guide wave ϕ propagated through the entire stem (axis) are known to have the great correlation with water potential ϕw and the turgor pressure of the cell.

When the result illustrated in FIG. 41(a) and FIG. 41(b) is used to examine the relationship between the sound velocity v, attenuation rate α and water potential ϕw of the plant of the targeted species in advance, by measuring the sound velocity v and attenuation rate α of the guide wave ϕ propagated through the entire stem (axis), it is possible to measure water potential ϕw and consequently evaluate water state of the herbaceous plant.

<Evaluating Method of Water State of Woody Plant>

When water potential ϕw of the woody plant is measured, the turgor pressure of the cell has no substantial influence on the entire rigidity of the side axes (branches) $2_{b1}$, $2_{b2}$, $2_{b3}$, - - - and the main axis (stalk) $2_t$. However, in the side axes (branches) $2_{b1}$, $2_{b2}$, $2_{b3}$, - - - and the main axis (stalk) $2_t$ of the woody plant, even if water stress is small, the embolism is generated in the heartwood. The embolism density is changed correspondingly to water potential ϕw. That is, when water potential ϕw decreases, because the embolism density of the heartwood decreases, and the moisture content increases, in association with the decrease of water potential ϕw, the sound velocity v and the attenuation rate α increases. The relationship between the decrease of water potential ϕw and the increase of the sound velocity v and the attenuation rate α is equal to the principle of the calculation of the relative embolism density, which is based on the measurement of the sound velocity and attenuation rate of the guide wave propagated through the sapwood.

Similarly to FIG. 34, the acoustic vibrator 61 and the acoustic receiver 62 are attached to the main axis (stalk) $2_t$ of the strawberry tree. Then, the burst acoustic wave is generated from the sounding body for each six minutes, and the guide wave ϕ propagated through the main axis (stalk) $2_t$ is measured by the acoustic receiver 62. In the experiment, the illumination is turned on at a cycle of twelve hours, and everyday, the irrigating operation is carried out one hour before the illumination is turned off (after eleven hours, after 35 hours and after 59 hours).

Figure 42:
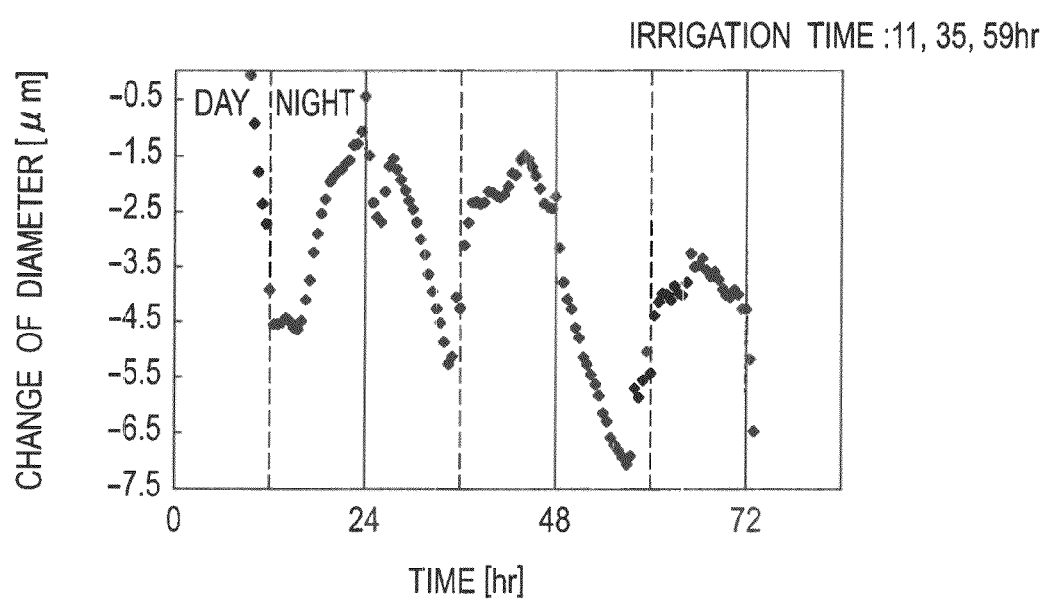
FIG. 42 is a view illustrating the variation per day in the axis diameter of the strawberry tree, in order to describe the evaluating method of water state of the plant according to the ninth embodiment.

FIG. 43(a) illustrates the result when the time-dependent change in the sound velocity v is measured in the process for recovering water stress from the state in which the severe water stress is given. FIG. 43(b) illustrates the result when the time-dependent change in the attenuation rate α is measured. When the waveforms measured by the acoustic receiver 62 are averaged for each 30 minutes, and the guide wave of 12.5 kHz is extracted by the wavelet analysis, FIG. 43 illustrates the time-dependent changes of the sound velocity v and attenuation rate α of the guide wave. Moreover, similarly to FIG. 34, when the diameter gauge 63 is placed in the main axis (stalk) $2_t$, FIG. 42 illustrates the change in the diameter of the measured main axis (stalk) $2_t$. The diameter change in the main axis (stalk) $2_t$ corresponds to the change in water potential.

The wavelength (between 35 and 42 mm) of the guide wave of 12.5 kHz is sufficiently longer than the diameter (12 mm) of the main axis (stalk) $2_t$. Thus, the guide wave is propagated through the whole of the main axis (stalk) $2_t$. Since the irrigating operation is not carried out until eleven hours, at the beginning of the experiment, the great embolism is generated in the strawberry tree. However, the sound velocity v and the attenuation rate α are decreased by the irrigating operation after the eleven hours. Here, since the sound velocity v and the attenuation rate α receive the influence of the embolism of the sapwood, the correlation with water potential is weak. However, the embolism of the sapwood is almost removed by the irrigating operation after the 35 hours. So, when the embolism density of the heartwood begins to be decreased, the behaviors of the sound velocity v and the attenuation rate α become coincident with the behavior of the diameter change. However, with regard to the attenuation rate α, it is necessary to consider the influence of the decrease in the attenuation rate α that is associated with the increase in the moisture content. FIG. 44(a) illustrates the relationship between the diameter change in the main axis (stalk) $2_t$ and the change in the sound velocity v, on and after the 36 hours. FIG. 44(b) illustrates the relationship between the diameter change in the main axis (stalk) $2_t$ and the change in the attenuation rate ratio $R_a$ on and after the 36 hours. The attenuation rate ratio $R_a$ is the ratio between the attenuation rate α of the guide wave of 12.5 kHz and the attenuation rate α of the guide wave of 100 kHz, and the value of the moisture content of the sapwood is estimated from the attenuation rate of the guide wave of 100 kHz, and the influence of the decrease in the attenuation rate α ascribable to the increase in the moisture content is considered to correct the value of the attenuation rate α. Both of the sound velocity v and the attenuation rate ratio $R_a$ have the correlation with the diameter change. Thus, when the correlation is used to examine the relationship between the sound velocity v, attenuation rate α and water potential c w of the plant of the targeted species in advance, by measuring the sound velocity v and attenuation rate α of the guide wave propagated through the whole of the side axes (branches) $2_{b1}$, $2_{b2}$, $2_{b3}$, - - - and main axis (stalk) $2_t$, it is possible to measure water potential ϕw and consequently evaluate water state of the woody plant.

Water potentials of the herbaceous plant and the woody plant are more generically measured by using the pressure chamber method. However, since the measurement of the pressure chamber method is carried out by cutting (disconnecting) leafs, the consecutive measurement is impossible. However, according to the evaluation method of degree of botanical-integrity in vascular plant pertaining to the ninth embodiment, for a long period, water potentials of the herbaceous plant and the woody plant can be consecutively measured, which is useful for monitoring water state of the crops.

Tenth Embodiment

In green vegetables, chewiness and sweetness are said to be the index of freshness. However, the chewiness and the sweetness have the close relation to the turgor pressure of the cell in the inside of a leaf. The turgor pressure of the cell has influence on the rigidity of leafs. Thus, when the turgor pressure decreases, the chewiness is lost. Also, the turgor pressure is generated by the decrease in a spread potential ϕs in the inside of the cell. Then, when a solute concentration in the inside of the cell decreases, the spread potential ϕs increases, and the turgor pressure decreases. Also, the decrease in the solute concentration leads to the decrease in the sweetness. In this way, with regard to the freshness of the green vegetable, the solute concentration in the inside of the cell is important to be kept high. Then, when water is sufficiently given and water potential ϕw is sufficiently high, as shown in Eq. (1), the value of the solute concentration (spread potential) coincides with the value of the turgor pressure of the cell. On the other hand, the guide wave propagated through the entire vein exhibits the behavior, which is described about the herbaceous plants in the ninth embodiment. Then, its sound velocity v and attenuation rate α have the relation to the turgor pressure of the cell in the inside of the vein. So, by using an osmotic meter (osmotic pressure meter) and the like and examining the solute concentration in the leafs of the plant of the targeted species in advance and then determining the relationship between the sound velocity v and attenuation rate α of the guide wave propagated through the entire vein at that time, it is possible to calculate the solute concentration from the sound velocity v and attenuation rate α of the guide wave propagated through the entire vein, and to determine the turgor pressure of the cell and consequently to evaluate the botanical-integrity in vascular plant.

Although the illustration is omitted, the tenth embodiment of the present invention implies the evaluation method of degree of botanical-integrity in vascular plant, which attaches the acoustic vibrator and the acoustic receiver to the vein in the green vegetable or the like, and measures the sound velocity v and attenuation rate α of the guide wave ϕ propagated through the entire vein and consequently measures the turgor pressure of the cell between the plants in which the solute concentrations are different.

For example, water is sufficiently given to green vegetables sold in the market, and the green vegetables are displayed. So, by attaching the acoustic vibrator and the acoustic receiver to the vein of the green vegetables and then examining the sound velocity and attenuation rate of the guide wave propagated through the entire vein, it is possible to evaluate the freshness of the green vegetable from the turgor pressure of the cell. In this case, the sound velocity v and attenuation rate α of the guide wave propagated through the entire vein just after the harvest of the good green vegetable are assumed to be 100%, and when the solute concentration is reduced to a particular value, the sound velocity v and attenuation rate α of the guide wave propagated through the entire vein are assumed to 0%. So, the freshness evaluation (evaluation of the botanical-integrity) may be carried out.

The evaluation method of degree of botanical-integrity in vascular plant according to the tenth embodiment is desired to use the film electret sensor, which is described in the first embodiment and illustrated in FIGS. 5 and 6, as the acoustic vibrator and the acoustic receiver. Also, the film ECM array according to the seventh embodiment in which the acoustic vibrator and the acoustic receiver are integrated as illustrated in FIGS. 32 and 33 can be used to further simply carry out the measurement.

In the measurements of the sound velocity v and the attenuation rate α, when the leaves such as cabbage and lettuce are closely adhered to each other, the leaves are desirably measured such that one leafs is separated or the vein portion between the acoustic vibrator and the acoustic receiver is held so as not to be brought into contact with the other material. In particular, in the measurement of the attenuation rate α, the contact with the other material whose acoustic impedance is closer to that of the vein disables the accurate measurement because the guide wave is propagated through the contact portion with the other material. In the measurement of the sound velocity, unless the mode of the guide wave propagated through the vein portion between the acoustic vibrator and the acoustic receiver is changed, the contact with the other material is allowable. Even in the case that the leaves such as the cabbage and the lettuce are closely adhered to each other, in their original states, the sound velocity can be measured for the vein of the outmost leafs. Or, when the state of the outmost leafs is the worst, the film electret sensor is inserted between the outmost leafs and the next outmost leafs. Then, by pushing against the vein of the next leafs, the sound velocity v of the vein of the next leafs may be measured. Also, even when green vegetables are packed with a vinyl bag, the acoustic vibrator and the acoustic receiver are placed to be pushed through the vinyl bag against the vein, and the guide wave can be measured.

As the freshness evaluation of the green vegetable, there is a method of using chlorophyll fluorescence. However, the method using chlorophyll fluorescence is intended to examine the activation level of the photosynthesis. Thus, the method is the indirect evaluation method.

According to the evaluation method of degree of botanical-integrity in vascular plant pertaining to the tenth embodiment of the present invention, it is possible to simply measure the solute concentration (the turgor pressure of the cell) directly related to the freshness of the green vegetable and easily insure the quality of the green vegetable for consumers.

Eleventh Embodiment

Such as the bacterial canker and the like, the disease damage of the plant breaks leafs and stems in many cases. At this time, the vascular tissue is preferentially infected and blighted. When the vascular plant is infected with the foregoing disease damage, the embolism cannot be recovered even under the good irrigation condition, and the embolism density increases. At this time, by periodically measuring the sound velocity v and attenuation rate α of the guide wave propagated through the vascular bundle of the stem (axis) and the guide wave propagated through the entire step (axis), it is possible to evaluate the botanical-integrity of the vascular bundle. The evaluation method of degree of botanical-integrity in vascular plant according to the eleventh embodiment of the present invention is the method that evaluates the degree of botanical-integrity for the plant against the disease damage, by measuring the embolism density and water potential ϕw.

In the evaluation method of degree of botanical-integrity in vascular plant according to the eleventh embodiment, for example, in the case that the plant targeted for the evaluation is the tomato, as illustrated in FIGS. 30, 31 and 32 described in the seventh embodiment, the acoustic vibrator 61 and the acoustic receiver 62 are attached to the axis, and the acoustic wave is periodically transmitted/received, and the guide wave propagated through the entire stem (axis) and the guide wave propagated through the vascular tissue are extracted from the transmission/reception waveform, and the respective sound velocities v and attenuation rates α are calculated. The above measurement and calculation are periodically repeated, which monitors water potential ϕw and the relative embolism density. At that time, even if the decrease in water potential ϕw is small, when there is a tendency that the embolism density increases, the botanical-integrity of the vascular bundle shall be carefully considered. When there is a tendency that the embolism density increases, as the states of the tomato, the following four possibilities can be assumed:

(a) the state in which the embolism generated by the severe water stress is recovered;

(b) the state in which, since the growth is remarkable, the growth causes the occurrence of the embolism;

(c) the state in which the disease damage causes the drop in the embolism recovery performance of the vascular bundle; and (d) the state in which the aging causes the drop in the embolism recovery performance of the vascular bundle.

The possibility (a) can be speculated from the irrigation condition until that time, and the possibility (b) can be speculated from the growth velocity at a level that can be visually judged. Then, when the exposure to the severe water stress is not conjectured and it is inferred that the growth velocity is not so high, the state of possibility (c) or possibility (d) is doubted. In this case, the botanical-integrity of the plant decreases at any rate. Then, by examining even the botanical-integrity of the nearby tomato through the use of the acoustic measurement of the present invention, it is necessary to exchange the seedling, improve the soil and reconsider the irrigation condition and the temperature condition.

As mentioned above, according to the evaluation method of degree of botanical-integrity in vascular plant pertaining to the eleventh embodiment of the present invention, the decrease in the botanical-integrity of the plant can be detected at the early stage, as compared with the visual evaluation. Thus, it is possible to evaluate the botanical-integrity in vascular plants such as the tomato and the like and efficiently carry out the cultivation.

Other Embodiments

As mentioned above, the present invention has been described by using the first to eleventh embodiments. However, the discussions and the drawings that implement a part of the disclosure should not be construed to limit the present invention. From this disclosure, various implementations, variations, embodiments and operational techniques would be evident for one skilled in the art.

For example, as described in the seventh embodiment, the relative embolism density can be determined from the measurement of the sound velocity v and attenuation rate α of the vascular plant. However, the risk level of the embolism of the vascular plant actually receives the influences of the various factors, such as temperature, humidity, solar radiation, fertilization, disease damage and the like, as well as the soil water. For this reason, the measurement of the elastic wave (AE) is essential in order to surely know the risk level of the embolism. However, the measurement of the elastic wave (AE) involves the damages such as the fastening of the axis and the cut of the branch. Thus, the frequent measurement is not preferable. For this reason, by combining one of the techniques described in the first to sixth embodiments with the technique described in the seventh embodiment, it is desired to efficiently diagnose the embolism. For example, everyday, the sound velocity v and the attenuation rate α are measured to examine the relative embolism density. Then, at a rate of one time between three days and one week, or when the great change is generated in the environment such as the fertilization, the elastic wave (AE) is measured to check the risk level. Consequently, it is possible to suppress the damage to the plants to a slight degree and monitor the embolism risk in the particular environment. For the film ECM array illustrated in FIG. 33, the measurement of the elastic wave (AE) of the vascular plants and the measurement of the attenuation rate α of the guide wave φ can be carried out at the same time, which leads to even the improvement of the measurement precision of the relative embolism density.

In this way, naturally, the present invention includes the various implementations, embodiments and the like, which are not described herein. Thus, the technical scope of the present invention can be determined only the reasonable inventive particular features stated in Claims.

INDUSTRIAL APPLICABILITY

The present invention can be applied to: a field of an agriculture, a landscape gardening, a green plant, and a forestry that cultivate and grow the vascular plants such as crops, garden plants and the like; a distribution field that carries and distributes the vascular plants such as the crops, the garden plants and the like; a commercial field of a vegetable shop, a supermarket, a flower shop and the like that sell the vascular plants such as the crops, the garden plants and the like; and a food-processing and cooking field that process the vascular plants such as the crops, the garden plants and the like. In particular, the present invention can be effectively used in the fields of the agriculture and the forestry that include the cultivation of the plants in the severe growing environments such as arid region of desert and the like.

| [REFERNCE SIGN LIST] | |
| --- | --- |
| 1 | Flower Pot |
| $2_{b1}, 2_{b2}, 2_{b3}, 2_{b4}$, - - - | Side Axes (Axis) |
| $2_{tc}$ | Marrow |
| $2_{th}$ | Epidermis |
| $2_{ti}$ | Vascular Tissue |
| $2_t$ | Main Axis |
| $3_t$ | Vein (Axis) |
| 3 | Leaf |
| 8 | Vacuum Box |
| 9 | Vacuum Pump |
| $11_{afij}$ | Element |
| 11af | Sensor Unit |
| 11a, 11b, 11c, 11d, 11p, 11q, 11r, 11s | Elastic Wave Reception Device (AE Sensor) |
| 12a, 12b, 12c, 12d, 12p, 12q, 12, 12s | Rubber Sheet |
| 13 | Soil Water Sensor |
| 17 | Screw |
| 21, 21a, 21b | Clip |
| 22 | Cover |
| 23 | Main Body |
| 24 | Rotation Buffer |
| 25 | Rubber Pad |
| 25a, 25b | Pushing Plate |
| 26 | Spring |
| 27 | Flexible Base |
| 28 | Adhesive Tape |
| 31 | Shield Plate |
| 31a | Shield Conductor Protection Film |
| 31b | Shield Conductor Film |
| 32a | Spacer Film |
| 32b | Side Wall Film |
| 33 | Electret Film |
| 34a, 34b, 34c | Gap Insulation Film |
| 35 | Vibration Film |
| 35a | Vibration Electrode Insulation Film |
| 35b | Vibration Electrode Film |
| 36 | Vibration Film Protection Film |
| 37 | Back Electrode Film |
| 38 | Circuit Substrate |
| 39 | Semiconductor Chip |
| 41a, 41b, 41c, 41d | Spacer |
| 42 | Shield Conductor Film |
| 43, 44 | Shield Conductor Protection Film |
| 43m | Polymer Film |
| 44 | Shield Conductor Protection Film |
| 45 | Passivation Film |
| 45m | Vibration Electrode Film |
| 47m, 47s, 47a, 47b | Back Electrode Film |
| 48 | Inter-Layer Insulation Film |
| 48s, 48a, 48b | Circuit Substrate |
| 51a, 51b | Pushing Plate |
| 52a, 52b | Sponge |
| 53a, 53b | Film ECM Array |
| 54 | Pushing Plate |
| 55a, 55b | Wedge |
| 57 | Pressuring Bag |
| 58 | Adhesive Tape |
| 61 | Acoustic Vibrator |
| 62 | Acoustic Receiver |
| 62a | First Acoustic Receiver |
| 62b | Second Acoustic Receiver |
| 71s, 71a, 71b | Signal Line |
| 73s, 73a, 73b | Amplifier |
| 81 | first Vacuum Hose |
| 82 | Second Vacuum Hose |
| 83 | Sucking Pipe |
| 82 | Exhausting Pipe |

| [REFERNCE SIGN LIST] | |
|---|---|
| 91 | Pressure Gauge |
| 141$_{ij}$, 142$_{ij}$, 143$_{ij}$, 141a, 142a, 143a | Gap Insulation Film |
| 201 | Vessel |
| 202j | Cell Wall |

The invention claimed is:

1. A method for evaluating degree of botanical-integrity in vascular plant, comprising:
measuring an occurrence frequency of elastic waves generated by cavitations in vascular tissues in vascular plant, before and after a change in water stress to the vascular plant, respectively by an elastic wave reception sensor fixed to an axis of the vascular plant;
calculating a change rate of the occurrence frequency, from the occurrence frequency of the elastic wave measured before and after the change, respectively; and
determining whether or not an embolism in the vascular tissue arrives at an unrecoverable level of the embolism, from the calculated change rate,
wherein botanical-integrity of the vascular plant is evaluated, on the basis of the level of the embolism.

2. The method of claim 1, wherein the change rate is defined by a value, in which a value of the occurrence frequency measured when the water stress is high being subtracted by the occurrence frequency measured when the water stress is low is divided by a value of the occurrence frequency measured when the water stress is high being added by the occurrence frequency measured when the water stress is low.

3. The method of claim 2, wherein a case, in which the value of the calculated change rate is 0 or less, is determined to a state that the embolism has arrived at the unrecoverable level.

4. The method of claim 2, wherein the occurrence frequency measured when the water stress is high is given by the occurrence frequency of the elastic wave that is measured in the daytime, and
the occurrence frequency measured when the water stress is low is given by the occurrence frequency of the elastic wave that is measured in the nighttime.

5. The method of claim 2, wherein the occurrence frequency measured when the water stress is high is given by the occurrence frequency of the elastic wave before the vascular plant is irrigated, and
the occurrence frequency measured when the water stress is low is given by the occurrence frequency of the elastic wave that is measured after the irrigation.

6. The method according to of claim 1, wherein the change in the water stress is given by one of:
cutting the axis in a portion closer to a root than the elastic wave reception sensor,
opening an aperture in a part of the portion, and
shaving a part of the portion,
with regard to the axis to which the elastic wave reception sensor is fixed.

7. The method according to claim 1, wherein the change in the water stress is given by pressuring the axis in the portion allocated closer to the root than the elastic wave reception sensor, with regard to the axis to which the elastic wave reception sensor is fixed.

8. The method of claim 1, wherein the change in the water stress is given by one of:
cutting the axis in a portion closer to a root than the elastic wave reception sensor,
opening an aperture in a part of the portion, and
shaving a part of the portion,
with regard to the axis to which the elastic wave reception sensor is fixed.

9. The method of claim 1, wherein the change in the water stress is given by pressuring the axis in the portion allocated closer to the root than the elastic wave reception sensor, with regard to the axis to which the elastic wave reception sensor is fixed.

10. The method according to claim 1, wherein the vascular plant has an annular vascular tissue, the irrigating method further includes:
attaching an acoustic vibrator and an acoustic receiver to another axis of the vascular plant,
measuring an attenuation rate of an acoustic wave propagated through the vascular tissue and determining an evaluated attenuation rate, and
dividing the measured attenuation rate by a value of a reference attenuation rate so as to obtain an attenuation rate ratio, the reference attenuation rate has been determined by an attenuation rate of an acoustic wave propagated through the vascular tissue measured in a state that a sufficient irrigation is carried out to the vascular plant in advance, and
wherein the calculated attenuation rate ratio is added as a new index to the index based on the determined result, and the irrigation timing and the irrigation quantity are determined.

11. A method for evaluating degree of botanical-integrity in vascular plant, comprising:
generating a burst acoustic wave of a wavelength longer than a diameter of an axis of vascular plant assigned as a measuring target, by an acoustic vibrator fixed to the axis;
measuring a guide wave generated by the burst acoustic wave and propagated through a whole of the axis, by an elastic wave reception sensor fixed to the axis;
determining a measured sound velocity and a measured sound velocity attenuation rate of the guide wave, from the measurement; and
comparing a reference sound velocity and a reference attenuation rate of a guide wave propagated through an entire axis of a reference vascular plant in a healthy botanical state with the measured sound velocity and the measured attenuation rate, respectively, the reference vascular plant is equal in species to the measuring target, the reference sound velocity and the reference attenuation rate is pre-examined with the reference vascular plant,
wherein a water state of the measuring target is evaluated.

12. The method of claim 11, wherein the axis is a vein of a green vegetable.

13. A method for irrigating vascular plant, comprising:
measuring an occurrence frequency of elastic waves generated by cavitations in vascular tissues in vascular plant, before and after a change in water stress to the vascular plant, respectively, by an elastic wave reception sensor fixed to an axis of the vascular plant;
calculating a change rate of the occurrence frequency, from the occurrence frequency of the elastic wave measured before and after the change, respectively;
determining whether or not an embolism of the vascular tissue arrives at an unrecoverable level, from the calculated change rate; and determining an irrigation timing and an irrigation quantity to the vascular plant, using the determined result as an index.

14. The method of claim 13, wherein the change rate is defined by a value, in which a value of the occurrence frequency measured when the water stress is high being subtracted by the occurrence frequency measured when the water stress is low is divided by a value of the occurrence frequency measured when the water stress is high being added by the occurrence frequency measured when the water stress is low.

15. The method of claim 14, wherein the occurrence frequency measured when the water stress is high is given by the occurrence frequency of the elastic wave that is measured in the daytime, and the occurrence frequency measured when the water stress is low is given by the occurrence frequency of the elastic wave that is measured in the nighttime.

16. The method of claim 14, wherein the occurrence frequency measured when the water stress is high is given by the occurrence frequency of the elastic wave before the vascular plant is irrigated, and the occurrence frequency measured when the water stress is low is given by the occurrence frequency of the elastic wave that is measured after the irrigation.

17. The method of claim 13, further including:

measuring a sound velocity of the acoustic wave, simultaneously with the attenuation rate of the acoustic wave; and determining a thickness of the vascular tissue from the sound velocity.

18. A method for irrigating vascular plant, including:

attaching an acoustic vibrator and an acoustic receiver to an axis of vascular plant having an annular vascular tissue, and measuring an attenuation rate of an acoustic wave propagated through the vascular tissue and then determining an measured attenuation rate;

dividing the measured attenuation rate by a value of a reference attenuation rate so as to calculate an attenuation rate ratio, the reference attenuation rate is determined by an attenuation rate of the acoustic wave propagated through the vascular tissue measured in a case that a sufficient irrigation is carried out to the vascular plant in advance; and determining an irrigation timing and an irrigation quantity to the vascular plant, with the calculated attenuation rate ratio as an index.

19. The method of claim 18, further including:

measuring a sound velocity of the acoustic wave, simultaneously with the attenuation rate of the acoustic wave; and determining a thickness of the vascular tissue from the sound velocity.

* * * * *